(12) United States Patent
Baliga et al.

(10) Patent No.: US 11,657,895 B2
(45) Date of Patent: May 23, 2023

(54) METHODS FOR IDENTIFYING TREATMENT TARGETS BASED ON MULTIOMICS DATA

(71) Applicant: INSTITUTE FOR SYSTEMS BIOLOGY, Seattle, WA (US)

(72) Inventors: Nitin S. Baliga, Tempe, AZ (US); Christopher L. Plaisier, Tempe, AZ (US)

(73) Assignee: INSTITUTE FOR SYSTEMS BIOLOGY, Seattle, WA (US)

( * ) Notice: Subject to any disclaimer, the term of this patent is extended or adjusted under 35 U.S.C. 154(b) by 1179 days.

(21) Appl. No.: 16/097,897

(22) PCT Filed: May 3, 2017

(86) PCT No.: PCT/US2017/030750
§ 371 (c)(1),
(2) Date: Oct. 31, 2018

(87) PCT Pub. No.: WO2017/192662
PCT Pub. Date: Nov. 9, 2017

(65) Prior Publication Data
US 2020/0013480 A1    Jan. 9, 2020

Related U.S. Application Data

(60) Provisional application No. 62/331,276, filed on May 3, 2016.

(51) Int. Cl.
*G01N 33/48* (2006.01)
*G01N 33/50* (2006.01)
(Continued)

(52) U.S. Cl.
CPC ............ *G16B 15/30* (2019.02); *C12N 15/111* (2013.01); *G16B 25/10* (2019.02); *G16B 40/00* (2019.02); *G16B 45/00* (2019.02); *G16B 50/00* (2019.02); *G16C 20/50* (2019.02); *C12N 2310/141* (2013.01); *C12N 2320/11* (2013.01)

(58) Field of Classification Search
CPC ........ G16B 15/30; G16B 25/10; G16B 40/00; G16B 45/00; G16B 50/00; C12N 15/111; C12N 2310/141; C12N 2320/11
See application file for complete search history.

(56) References Cited

U.S. PATENT DOCUMENTS

2006/0185027 A1    8/2006 Bartel et al.

FOREIGN PATENT DOCUMENTS

WO    WO-2014210341 A2 * 12/2014    ........... C12Q 1/6886

OTHER PUBLICATIONS

Sun et al. Uncovering microRNA and transcription factor mediated regulatory networks in glioblastoma. PLoS Computational Biology, vol. 8, article e11002488, 14 pages. (Year: 2012).*

(Continued)

*Primary Examiner* — Russell S Negin
(74) *Attorney, Agent, or Firm* — Marshall, Gerstein & Borun LLP

(57) ABSTRACT

The invention includes methods and systems for identifying targets for therapeutic intervention for various diseases and conditions; and provides specific materials and methods for treatment of specific diseases and conditions.

13 Claims, 12 Drawing Sheets

Specification includes a Sequence Listing.

(51) Int. Cl.
　　　*G16B 15/30*　　(2019.01)
　　　*G16B 25/10*　　(2019.01)
　　　*G16B 45/00*　　(2019.01)
　　　*C12N 15/11*　　(2006.01)
　　　*G16C 20/50*　　(2019.01)
　　　*G16B 40/00*　　(2019.01)
　　　*G16B 50/00*　　(2019.01)

(56) References Cited

OTHER PUBLICATIONS

Reiss et al. cMonkey2: Automated, systemic, integrated detection of co-regulated gene modules for any organism. Nucleic Acids Research, vol. 43, Apr. 14, 2015, article e87, 13 pages.*
Yue et al. Survey of computational algorithms for microRNA target prediction. Current Genomics, vol. 10, pp. 478-492. (Year: 2009).*
International Search Report issued in PCT Patent Application No. PCT/US17/30750 dated Nov. 28, 2017.
Written Opinion issued in PCT Patent Application No. PCT/US17/30750 dated Nov. 28, 2017.

* cited by examiner

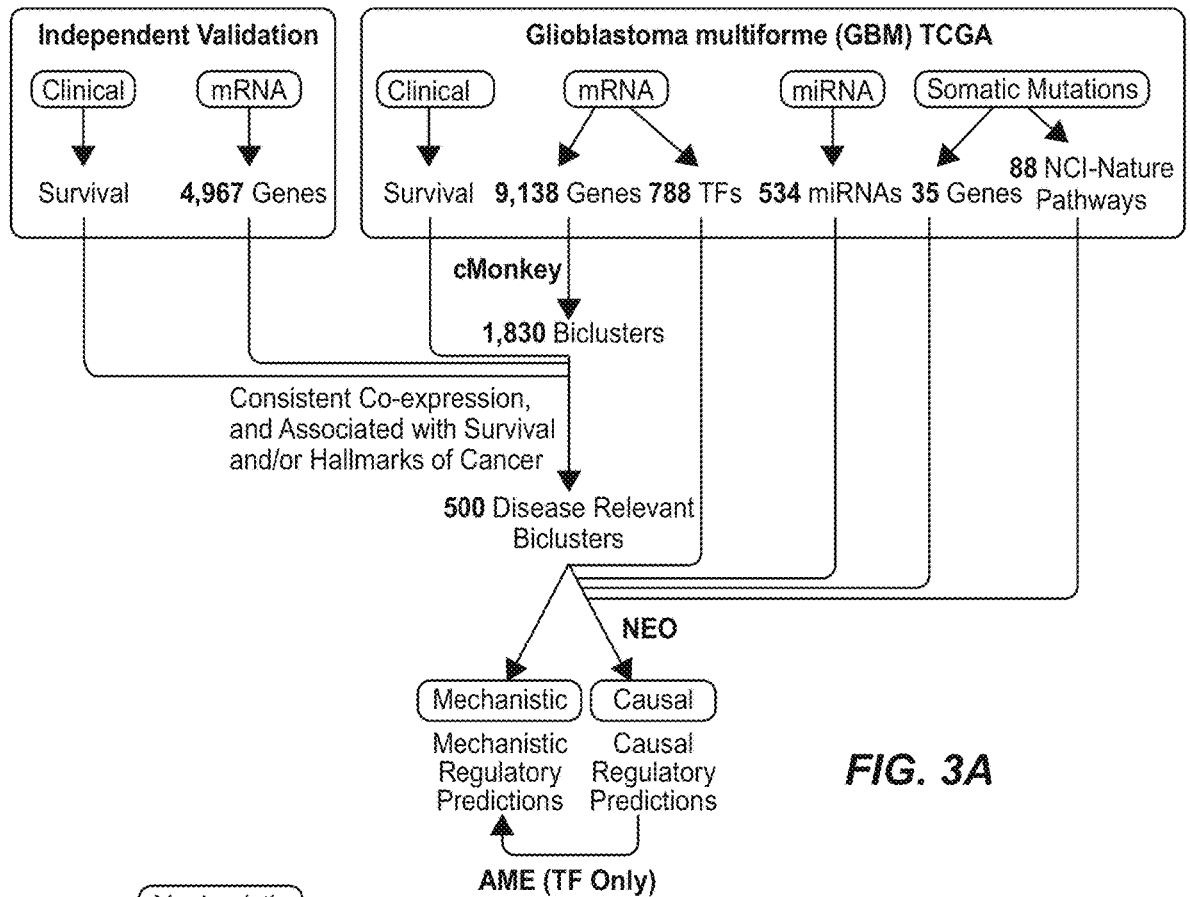
FIG. 3A
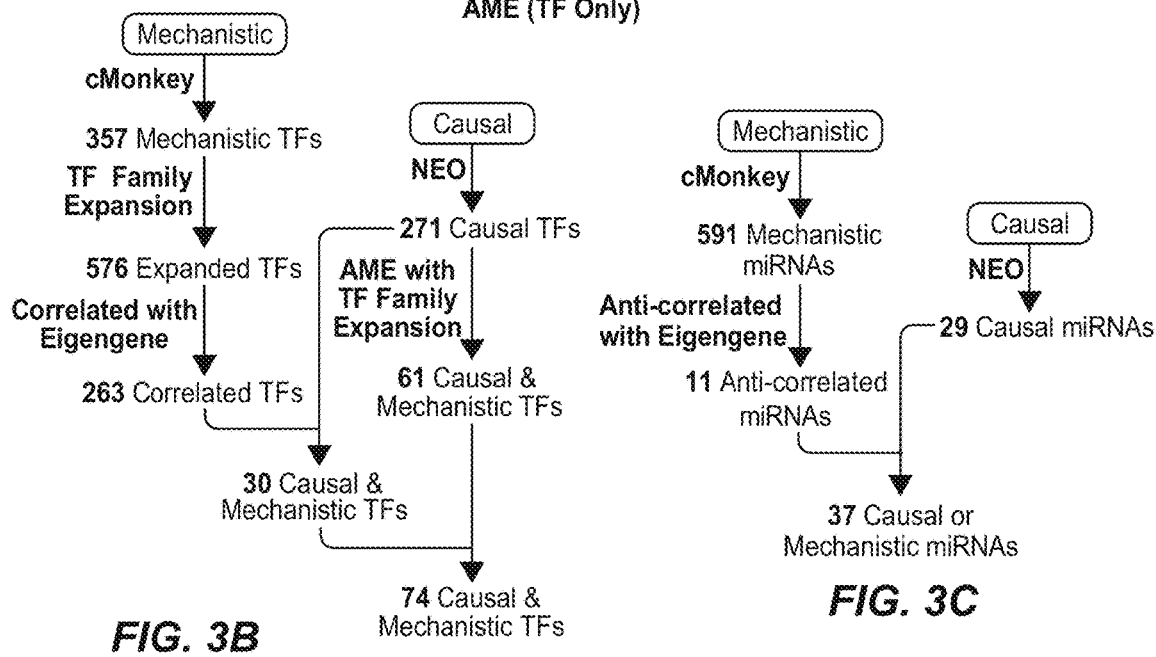
FIG. 3B
FIG. 3C

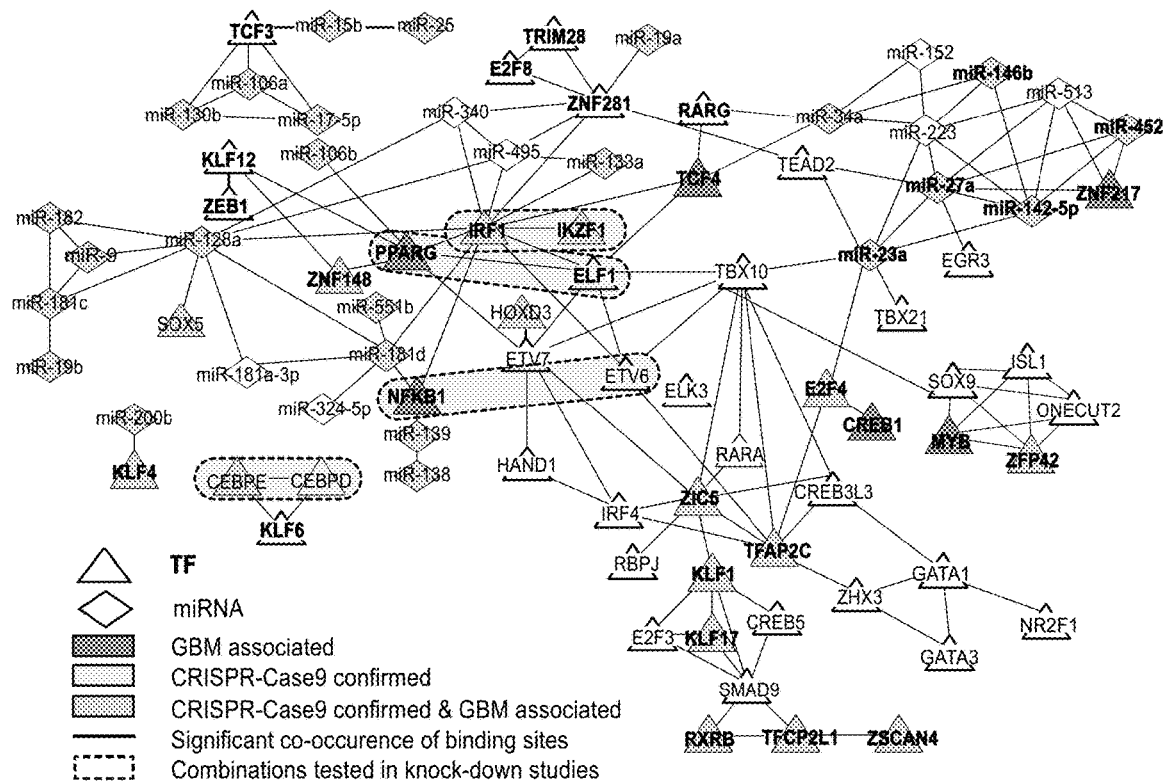
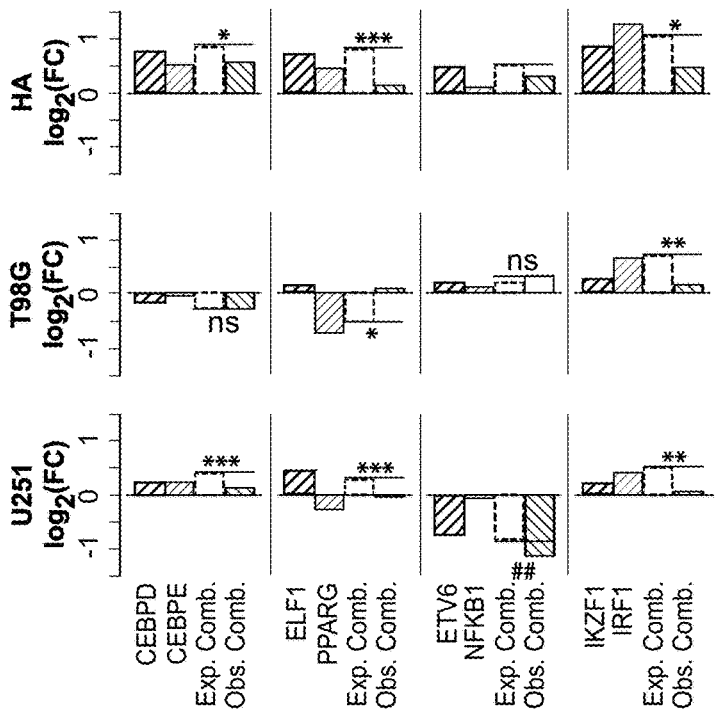
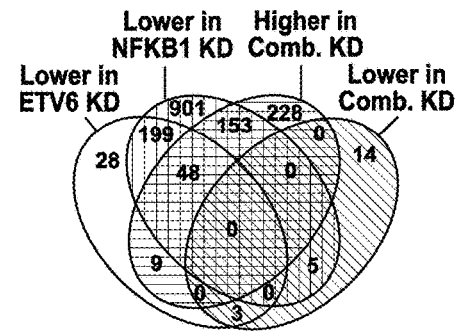
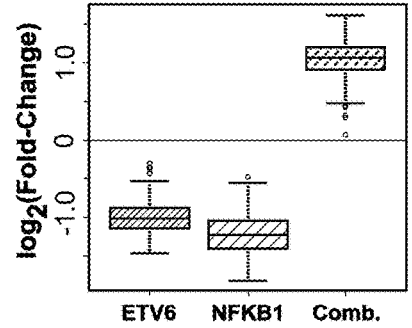
FIG. 4A
FIG. 4B
FIG. 4C
FIG. 4D

SEQUENCE LISTING

<160> NUMBER OF SEQ ID NOS: 29

<210> SEQ ID NO 1
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 1
aaaagugcuu acagugcagg uag                                              23

<210> SEQ ID NO 2
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 2
uaaagugcug acagugcaga u                                                21

<210> SEQ ID NO 3
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 3
cggggccgua gcacugucug aga                                              23

<210> SEQ ID NO 4
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 4
cggggccgua gcacugucug aga                                              23

<210> SEQ ID NO 5
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 5
acucuuuccc uguugcacua c                                                21

```
<210> SEQ ID NO 6
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 6
agcugguaaa auggaaccaa au                                                  22

<210> SEQ ID NO 7
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 7
uuuggucccc uucaaccagc ua                                                  22

<210> SEQ ID NO 8
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 8
agcugguguu gugaaucagg ccg                                                 23

<210> SEQ ID NO 9
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 9
ucuacagugc acgugucucc agu                                                 23

<210> SEQ ID NO 10
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 10
cauaaaguag aaagcacuac u                                                   21

<210> SEQ ID NO 11
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 11
ugagaacuga auuccauagg cu                                                  22

<210> SEQ ID NO 12
<211> LENGTH: 23
<212> TYPE: DNA
<213> ORGANISM: Artificial Sequence
<220> FEATURE:
<223> OTHER INFORMATION: Synthetic Polynucleotide
```

<400> SEQUENCE: 12
agguucugug auacacuccg acu                                      23

<210> SEQ ID NO 13
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 13
uagcagcaca ucaugguuua ca                                       22

<210> SEQ ID NO 14
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 14
caaagugcuu acagugcagg uag                                      23

<210> SEQ ID NO 15
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 15
accaucgacc guugauugua cc                                       22

<210> SEQ ID NO 16
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 16
aacauucaac cugucggug agu                                       22

<210> SEQ ID NO 17
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 17
aacauucauu gugucggug ggu                                       23

<210> SEQ ID NO 18
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 18
aguuuugcau aguugcacua ca                                       22

<210> SEQ ID NO 19

```
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 19
aguuuugcag guuugcaucc agc                                               23

<210> SEQ ID NO 20
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 20
uagcuuauca gacugauguu ga                                                22

<210> SEQ ID NO 21
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 21
cucaguagcc aguguagauc cu                                                22

<210> SEQ ID NO 22
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 22
cguguauuug acaagcugag uu                                                22

<210> SEQ ID NO 23
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 23
gggguuccug gggaugggau uu                                                22

<210> SEQ ID NO 24
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 24
aggcggagac uugggcaauu g                                                 21

<210> SEQ ID NO 25
<211> LENGTH: 22
<212> TYPE: DNA
<213> ORGANISM: Artificial Sequence
<220> FEATURE:
<223> OTHER INFORMATION: Synthetic Polynucleotide
```

```
<400> SEQUENCE: 25
agggcuuagc ugcuugugag ca                                            22

<210> SEQ ID NO 26
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 26
cgcauccccu agggcauugg ugu                                           23

<210> SEQ ID NO 27
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 27
uggcaguguc uuagcugguu gu                                            22

<210> SEQ ID NO 28
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 28
aacuguuugc agaggaaacu ga                                            22

<210> SEQ ID NO 29
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 29
uucacaggga ggugucau                                                 18
```

METHODS FOR IDENTIFYING TREATMENT TARGETS BASED ON MULTIOMICS DATA

STATEMENT REGARDING FEDERAL RESEARCH

This invention was made with government support under grants from the National Institutes of Health (NIH) (P50GM076547 and 1R01GM077398-01A2), National Science Foundation (NSF) (ABI NSF-1262637, DBI-0640950), and National Cancer Institute (NCI) (U24CA143835). The government has certain rights in the invention.

TECHNOLOGICAL FIELD

The present invention relates to personalized medicine, including evaluation of disease (e.g., cancer) etiology; identification of treatment targets and treatment regimens, and methods of treatment.

BACKGROUND

Glioblastoma multiforme (GBM) is the most common brain tumor and is nearly uniformly fatal. Development of new therapeutics has been slow and difficult (Alexander et al., 2013), in part because GBM is a complex and heterogeneous disease (Brennan et al., 2013).

One possible strategy to achieve complete and durable remission of GBM or other difficult-to-treat cancers is to tailor a combination of drugs that target multiple vulnerabilities in a patient's tumor. One of the obstacles to success in such endeavors is the need for a tool that navigates the large space of possible drug combinations and prioritizes specific drug combinations based on the molecular signatures of a patient's tumor.

SUMMARY

This invention provides materials and methods that help to address the problem of how to better characterize, understand, and treat diseases, including cancer, including the need for new tools that lead to or constitute cancer therapy with improved efficacy and/or greater selectivity.

A method for identifying treatment targets for a condition includes receiving a set of multiomics data. The multiomics data include transcriptomics data that in turn, includes data related to the condition. The method also includes filtering the transcriptomics data to determine a set of highly expressed genes related to the condition, and determining from the set of highly expressed genes a set of biclusters in which each bicluster represents a conditionally co-regulated module of genes. The method includes determining from the set of biclusters a set of disease-relevant biclusters.

In embodiments, determining from the set of biclusters a set of disease-relevant biclusters includes determining from the set of biclusters a first subset of biclusters, each bicluster in the first subset of biclusters having conditional up/down regulation associated with patient survival in a set of validation data. Determining the set of disease-relevant biclusters includes determining from the set of biclusters a second subset of biclusters, each bicluster in the second subset biclusters having conditional up/down regulation associated with patient survival or a disease hallmark in the set of multiomics data, and selecting, as the set of disease-relevant biclusters, biclusters that are in both the first subset of biclusters and the second set of biclusters.

In some instances the method includes receiving in the multiomics data a set of genomics data related to the condition, filtering the set of genomics data to determine a set of somatically mutated genes associated with the condition, and filtering the set of genomics data to determine a set of pathways aggregating somatically mutated genes.

In further embodiments, the method includes determining a set of bicluster eigengenes from the set of disease-relevant biclusters, and determining from at least the set of bicluster eigengenes a set of causal transcription factors and a set of causal miRNAs.

In some embodiments, determining a set of causal transcription factors and a set of causal miRNAs includes inputting into a network edge orienting algorithm the set of bicluster eigengenes, the set of somatically mutated genes associated with the condition, the set of pathways aggregating the somatically mutated genes, a set of miRNAs from the multiomics data, and a set of transcription factors from the multiomics data.

Determining a set of biclusters may also include, in embodiments determining a set of mechanistic transcription factors, and determining a set of mechanistic miRNAs. The method may also include expanding the set of mechanistic transcription factors to include other transcription factors in a same family as each of the set of mechanistic transcription factors, and finding a set of correlated transcription factors in the expanded set of mechanistic transcription factors that are correlated with bicluster eigengenes. Additionally, the method may include determining a first set of transcription factors that have both causal and mechanistic support for regulation of the same bicluster, by taking the intersection of the set of correlated transcription factors and the set of causal transcription factors, determining a second set of transcription factors that have both causal and mechanistic support for regulation of the same bicluster, by inputting the set of causal transcription factors into an analysis of motif enrichment algorithm; and taking the union of the first set of transcription factors and the second set of transcription factors to produce a set of treatment targets including causal and mechanistic transcription factors. Further, the method may include determining restricted set of mechanistic miRNAs by restricting the set of mechanistic miRNAs to include only miRNAs that exhibit anti-correlated expression with bicluster eigengenes; and taking the union of the restricted set of mechanistic miRNAs and the set of causal miRNAs to produce a set of treatment targets including causal and mechanistic miRNAs.

A system for identifying treatment targets for a condition includes a processor operable to execute machine readable instructions for configuring a processor, and a memory storing the machine readable instructions. The machine readable instructions, when executed, cause the processor to receive a set of multiomics data, the multiomics data including transcriptomics data including data related to the condition. The instructions also cause the processor to filter the transcriptomics data to determine a set of highly expressed genes related to the condition, determine from the set of highly expressed genes a set of biclusters, each bicluster representing a conditionally co-regulated module of genes, and determine from the set of biclusters a set of disease-relevant biclusters.

In embodiments, the instructions for causing the processor to determine from the set of biclusters a set of disease-relevant biclusters include instructions that cause the processor to determine from the set of biclusters a first subset of biclusters, each bicluster in the first subset of biclusters having conditional up/down regulation associated with patient survival in a set of validation data. The instructions also cause the processor to determine from the set of biclusters a second subset of biclusters, each bicluster in the second subset biclusters having conditional up/down regulation associated with patient survival or a disease hallmark in the set of multiomics data, and select, as the set of disease-relevant biclusters, biclusters that are in both the first subset of biclusters and the second set of biclusters.

In embodiments, the instructions also cause the processor to receive in the multiomics data a set of genomics data related to the condition, filter the set of genomics data to determine a set of somatically mutated genes associated with the condition, and filter the set of genomics data to determine a set of pathways aggregating somatically mutated genes.

The instructions further cause the processor, in some embodiments, to determine a set of bicluster eigengenes from the set of disease-relevant biclusters, and determine from at least the set of bicluster eigengenes a set of causal transcription factors and a set of causal miRNAs.

The instructions that cause the processor to determine from at least the set of bicluster eigengenes a set of causal transcription factors and a set of causal miRNAs include, in embodiments, instructions that, when executed, cause the processor to execute a network edge orienting algorithm using as input: the set of bicluster eigengenes, the set of somatically mutated genes associated with the condition, the set of pathways aggregating the somatically mutated genes, a set of miRNAs from the multiomics data, and a set of transcription factors from the multiomics data.

The instructions that cause the processor to determine from the set of highly expressed genes a set of biclusters further may include instructions that cause the processor to determine a set of mechanistic transcription factors, and determine a set of mechanistic miRNAs.

In some embodiments, the instructions also cause the processor to expand the set of mechanistic transcription factors to include other transcription factors in a same family as each of the set of mechanistic transcription factors, and find a set of correlated transcription factors in the expanded set of mechanistic transcription factors that are correlated with bicluster eigengenes. Further, the instructions can cause the processor to determine a first set of transcription factors that have both causal and mechanistic support for regulation of the same bicluster, by taking the intersection of the set of correlated transcription factors and the set of causal transcription factors and, still further to determine a second set of transcription factors that have both causal and mechanistic support for regulation of the same bicluster, by inputting the set of causal transcription factors into an analysis of motif enrichment algorithm. The instructions can also cause the processor to take the union of the first set of transcription factors and the second set of transcription factors to produce a set of treatment targets including causal and mechanistic transcription factors.

As described below in detail, the method for identifying treatment targets has been exemplified with respect to GBM, and the method has identified numerous targets for therapeutic intervention.

Accordingly, additional aspects of the invention includes methods of treatment that comprise administering one or more therapeutic agents to a subject in need of treatment for GBM. Related aspects include use of agents for treatment of GBM; and use of agents in the manufacture of medicaments for the treatment of GBM.

In some variations, the therapies described herein are contemplated for treatment of any GBM patient because of the evidence presented herein validating the targets or combinations of targets. In some variations of the invention, a tumor sample from the patient is analyzed as described herein; specific targets for therapeutic intervention are selected based on the results; and those targets are modulated by administering therapeutics as described herein.

Many of the targets are transcription factors and miRNAs. Where the data indicates that increased activity of the TF or miRNA will be beneficial, exemplary therapeutics include replacement therapy of the TF or miRNA. TF replacement therapy, in some embodiments, is by means of gene therapy to generate endogenous expression of the desired TF (e.g., encoded by the transgene). Where the data indicates that decreased activity will be beneficial, inhibitors are contemplated. Numerous classes of inhibitors, including inhibitory nucleic acids, are described herein in detail.

In some variations, single agent therapy is contemplated. For instance, some of the targets identified for GBM have not previously been identified as targets for intervention in GBM, and single agent therapy directed at such targets is contemplated.

Furthermore, the method for identifying targets for GBM has identified a number of combinations of targets with functional interrelations, and aspects of the invention include multi-agent therapy directed at such combinations of targets. In some variations, treatment with two or more agents has at least additive beneficial effect. In some variations, the two or more agents have synergistic effects. The benefits of combination therapy can include, for example, increased therapeutic efficacy; reduced dosing requirements; reduced toxicity; and reduced side effects.

Both the single agent/single target and multi-agent/multi-target therapeutic aspects of the invention described herein can be combined with existing cancer therapies, such as existing standard-of-care therapies for GBM. Such combinations also are aspects of the invention.

Related variations of the invention include compositions and kits comprised of GBM therapeutic agents described herein (both single agent and combinations). For instance, the agents may be formulated with a pharmaceutically acceptable carrier. In still further embodiments, the invention includes a medical device, such as a syringe or catheter, containing therapeutics described herein.

Additional embodiments and aspects of the invention are reflected in the following numbered paragraphs:

1. A method for identifying treatment targets for a condition, the method comprising: receiving a set of multiomics data, the multiomics data including transcriptomics data including data related to the condition; filtering the transcriptomics data to determine a set of highly expressed genes related to the condition; determining from the set of highly expressed genes a set of biclusters, each bicluster representing a conditionally co-regulated module of genes; and determining from the set of biclusters a set of disease-relevant biclusters.

2. A method according to paragraph 1, wherein determining a set of biclusters comprises executing a biclustering algorithm using as training data one or more received sets of miRNA targets and/or one or more sets of transcription factor targets.

3. A method according to paragraph 2, wherein executing the biclustering algorithm comprises executing the cMonkey$_2$ algorithm.

4. A method according to paragraph 3, wherein the biclustering algorithm uses as training data the PITA database.

5. A method according to either paragraph 3 or paragraph 4, wherein the biclustering algorithm uses as training data the TargetScan database.

6. A method according to any one of paragraphs 2-5, wherein the biclustering algorithm uses as training data a set of transcription factor targets.

7. A method according to paragraph 6, wherein the set of transcription factor targets is created by: extracting from a human genome sequence a set of promoter sequences; searching the set of promoter sequences for instances of DNA recognition motifs to create a set of instances of DNA recognition motifs; and identifying in the set of instances of DNA recognition motifs those instances that intersect with digital genomic footprints to create a transcription factor target gene database.

8. A method according to any one of paragraphs 2-7, wherein the biclustering algorithm uses as training data two sets of miRNA targets and one set of transcription factor targets.

9. A method according to any one of paragraphs 1-8, wherein determining from the set of biclusters a set of disease-relevant biclusters comprises: determining from the set of biclusters a first subset of biclusters, each bicluster in the first subset of biclusters having conditional up/down regulation associated with patient survival in a set of validation data; determining from the set of biclusters a second subset of biclusters, each bicluster in the second subset biclusters having conditional up/down regulation associated with patient survival or a disease hallmark in the set of multiomics data; and selecting, as the set of disease-relevant biclusters, biclusters that are in both the first subset of biclusters and the second set of biclusters.

10. A method according to paragraph 9, wherein each of the validation data and the multiomics data comprises a set of survival data and a set of transcriptomics data.

11. A method according to any one of paragraphs 1-10, further comprising: receiving in the multiomics data a set of genomics data related to the condition; filtering the set of genomics data to determine a set of somatically mutated genes associated with the condition; and filtering the set of genomics data to determine a set of pathways aggregating somatically mutated genes.

12. A method according to paragraph 11, further comprising: determining a set of bicluster eigengenes from the set of disease-relevant biclusters; and determining from at least the set of bicluster eigengenes a set of causal transcription factors and a set of causal miRNAs.

13. A method according to paragraph 12, wherein determining from at least the set of bicluster eigengenes a set of causal transcription factors and a set of causal miRNAs comprises: inputting into a network edge orienting algorithm: the set of bicluster eigengenes; the set of somatically mutated genes associated with the condition; the set of pathways aggregating the somatically mutated genes; a set of miRNAs from the multiomics data; and a set of transcription factors from the multiomics data.

14. A method according to any one of paragraphs 1-13, wherein determining from the set of highly expressed genes a set of biclusters further comprises: determining a set of mechanistic transcription factors; and determining a set of mechanistic miRNAs.

15. A method according to paragraph 14, further comprising: expanding the set of mechanistic transcription factors to include other transcription factors in a same family as each of the set of mechanistic transcription factors; finding a set of correlated transcription factors in the expanded set of mechanistic transcription factors that are correlated with bicluster eigengenes; determining a first set of transcription factors that have both causal and mechanistic support for regulation of the same bicluster, by taking the intersection of the set of correlated transcription factors and the set of causal transcription factors; determining a second set of transcription factors that have both causal and mechanistic support for regulation of the same bicluster, by inputting the set of causal transcription factors into an analysis of motif enrichment algorithm; and taking the union of the first set of transcription factors and the second set of transcription factors to produce a set of treatment targets including causal and mechanistic transcription factors.

16. A method according to either paragraph 14 or paragraph 15, further comprising: determining restricted set of mechanistic miRNAs by restricting the set of mechanistic miRNAs to include only miRNAs that exhibit anti-correlated expression with bicluster eigengenes; and taking the union of the restricted set of mechanistic miRNAs and the set of causal miRNAs to produce a set of treatment targets including causal and mechanistic miRNAs.

17. A method according to any one of paragraphs 1-16, wherein the condition is glioblastoma multiforme.

18. A method according to any one of paragraphs 15-17, further comprising:
evaluating, for treatment targets in the set of treatment targets, whether the treatment target is positively or negatively associated with survival; determining the regulator function of the treatment target; and determining whether to decrease expression or activity (knock down) or increase expression or activity of the treatment target to achieve a therapeutic effect for the condition.

19. A method of selecting a combination therapy to inhibit growth of neopolastic cells in a mammalian subject, the method comprising: identifying two or more treatment targets, wherein the two or more treatment targets are independently selected from the group consisting of transcription factors and miRNAs, and determining whether increased expression/activity or decreased expression/activity of the two or more treatment targets is expected to decrease growth of the neoplastic cells, according to paragraph 18; and selecting as a combination therapy two or more agents to modulate the treatment targets in the directions expected to decrease growth of the neoplastic cells.

20. The method according to paragraph 19, that comprises determining that a decreased expression or activity of two or more targets is expected to decrease growth of the neoplastic cells, and that comprises selecting as the combination therapy two or more interfering RNAs to decrease expression of the two or more targets.

21. A method of treatment of a mammalian subject to inhibit growth of neopolastic cells, the method comprising: identifying two or more treatment targets, wherein the two or more treatment targets are independently selected from the group consisting of transcription factors and miRNAs, and determining whether increased expression/activity or decreased expression/activity of the two or more treatment targets is expected to decrease growth of the neoplastic cells, according to paragraph 18; and administering agents to the mammalian subject in amounts effective to modulate the treatment targets in the directions expected to decrease growth of the neoplastic cells.

22. The method according to paragraph 21 that comprises determining that decreased expression/activity of two or more treatment targets is expected to decrease growth of the neoplastic cells, and the administering step comprises administering interfering RNA molecules selected for the two or more treatment targets, to decrease expression/activity of the two or more targets.

23. A system for identifying treatment targets for a condition, the system comprising: a processor operable to execute machine readable instructions for configuring a processor; and a memory storing the machine readable instructions, the machine readable instructions, when executed, causing the processor to: receive a set of multiomics data, the multiomics data including transcriptomics data including data related to the condition; filter the transcriptomics data to determine a set of highly expressed genes related to the condition; determine from the set of highly expressed genes a set of biclusters, each bicluster representing a conditionally co-regulated module of genes; and determine from the set of biclusters a set of disease-relevant biclusters.

24. A system according to paragraph 23, wherein the instructions causing the processor to determine a set of biclusters comprise instructions causing the processor to execute a biclustering algorithm using as training data one or more received sets of miRNA targets and/or one or more sets of transcription factor targets.

25. A system according to paragraph 24, wherein the biclustering algorithm is the cMonkey$_2$ algorithm.

26. A system according to paragraph 25, wherein the biclustering algorithm uses as training data the PITA database.

27. A system according to either paragraph 25 or paragraph 26, wherein the biclustering algorithm uses as training data the TargetScan database.

28. A system according to any one of paragraphs 24-27, wherein the biclustering algorithm uses as training data a set of transcription factor targets.

29. A system according to paragraph 28, wherein the set of transcription factor targets is created by: extracting from a human genome sequence a set of promoter sequences; searching the set of promoter sequences for instances of DNA recognition motifs to create a set of instances of DNA recognition motifs; and identifying in the set of instances of DNA recognition motifs those instances that intersect with digital genomic footprints to create a transcription factor target gene database.

30. A system according to any one of paragraphs 24-29, wherein the biclustering algorithm uses as training data two sets of miRNA targets and one set of transcription factor targets.

31. A system according to any one of paragraphs 23-30, wherein the instructions causing the processor to determine from the set of biclusters a set of disease-relevant biclusters comprise instructions that cause the processor to: determine from the set of biclusters a first subset of biclusters, each bicluster in the first subset of biclusters having conditional up/down regulation associated with patient survival in a set of validation data; determine from the set of biclusters a second subset of biclusters, each bicluster in the second subset biclusters having conditional up/down regulation associated with patient survival or a disease hallmark in the set of multiomics data; and select, as the set of disease-relevant biclusters, biclusters that are in both the first subset of biclusters and the second set of biclusters.

32. A system according to paragraph 31, wherein each of the validation data and the multiomics data comprises a set of survival data and a set of transcriptomics data.

33. A system according to any one of paragraphs 23-32, further comprising instructions that, when executed, cause the processor to: receive in the multiomics data a set of genomics data related to the condition; filter the set of genomics data to determine a set of somatically mutated genes associated with the condition; and filter the set of genomics data to determine a set of pathways aggregating somatically mutated genes.

34. A system according to paragraph 33, further comprising instructions that, when executed, cause the processor to: determine a set of bicluster eigengenes from the set of disease-relevant biclusters; and determine from at least the set of bicluster eigengenes a set of causal transcription factors and a set of causal miRNAs.

35. A system according to paragraph 34, wherein the instructions that cause the processor to determine from at least the set of bicluster eigengenes a set of causal transcription factors and a set of causal miRNAs comprise instructions that, when executed, cause the processor to execute a network edge orienting algorithm using as input: the set of bicluster eigengenes; the set of somatically mutated genes associated with the condition; the set of pathways aggregating the somatically mutated genes; a set of miRNAs from the multiomics data; and a set of transcription factors from the multiomics data.

36. A system according to any one of paragraphs 23-35, wherein the instructions that cause the processor to determine from the set of highly expressed genes a set of biclusters further comprise instructions that cause the processor to: determine a set of mechanistic transcription factors; and determine a set of mechanistic miRNAs.

37. A system according to paragraph 36, further comprising instructions that cause the processor to: expand the set of mechanistic transcription factors to include other transcription factors in a same family as each of the set of mechanistic transcription factors; find a set of correlated transcription factors in the expanded set of mechanistic transcription factors that are correlated with bicluster eigengenes; determine a first set of transcription factors that have both causal and mechanistic support for regulation of the same bicluster, by taking the intersection of the set of correlated transcription factors and the set of causal transcription factors; determine a second set of transcription factors that have both causal and mechanistic support for regulation of the same bicluster, by inputting the set of causal transcription factors into an analysis of motif enrichment algorithm; and take the union of the first set of transcription factors and the second set of transcription factors to produce a set of treatment targets including causal and mechanistic transcription factors.

38. A system according to any one of paragraphs 23-37, wherein the condition is glioblastoma multiforme.

39. A system according to any one of paragraphs 23-38, further comprising a network interface coupled to a network, wherein the machine readable instructions are further operable to cause the processor to: retrieve via the network a set of multiomics data; retrieve via the network an updated set of miRNA targets; retrieve via the network an updated set of transcription factor targets; retrieve via the network an updated PITA database; and/or retrieve via the network an updated TargetScan database.

40. A method of treatment of a mammalian subject who has been diagnosed with glioblastoma multiforme (GBM), the method comprising: administering to the subject a first agent that targets, comprises, or mimics a first gene regulator; and administering to the subject a second agent that targets, comprises, or mimics a second gene regulator; wherein the first and second gene regulators are independently selected from the group consisting of miRNAs and transcription factors; and wherein the agents are administered in therapeutically effective amounts.

41. Use of two or more agents to treat a mammalian subject who has been diagnosed with glioblastoma multiforme (GBM), or for the manufacture of a medicament to treat a mammalian subject who has been diagnosed with GBM, wherein a first agent targets, comprises, or mimics a first gene regulator; wherein a second agent targets, comprises, or mimics a second gene regulator; wherein the first and second gene regulators are independently selected from the group consisting of miRNAs and transcription factors; and wherein the agents are used for administration in therapeutically effective amounts.

42. The method or use according to any one of paragraphs 40-41, wherein the mammalian subject is human.

43. The method or use according to any one of paragraphs 40-42, wherein the agents are administered in synergistically effective amounts.

44. The method or use according to any one of paragraphs 40-42, wherein the agents are administered in an amount effective to kill GBM cells in the subject.

45. A composition comprising a first agent that targets, comprises, or mimics a first gene regulator; and a second agent that targets, comprises, or mimics a second gene regulator; wherein the first and second gene regulators are independently selected from the group consisting of miRNAs and transcription factors; and wherein the composition is effective to treat GBM in a mammalian subject.

46. The composition according to paragraph 45, wherein the agents are present in the composition in synergistically effective amounts.

47. The composition according to paragraph 45 or 46, further comprising a pharmaceutically acceptable carrier.

48. A kit comprising a first agent that targets, comprises, or mimics a first gene regulator; and a second agent that targets, comprises, or mimics a second gene regulator; wherein the first and second gene regulators are independently selected from the group consisting of miRNAs and transcription factors; and wherein the agents are packaged together with instructions for co-administration to treat GBM in a mammalian subject, but are not in admixture.

49. The method, use, composition, or kit according to any one of paragraphs 40-48, wherein the first agent targets NFKB1 and inhibits NFKB1 expression or activity.

50. The method, use, composition, or kit according to paragraph 49, wherein the second agent comprises at least one agent selected from the group consisting of hsa-miR-181d, hsa-miR-139, mimetics thereof, and combinations thereof.

51. The method, use, composition, or kit according to paragraph 49, wherein the second agent comprises hsa-miR-181d or a mimetic thereof; and wherein the method or use further comprises administering or use of a third agent that comprises hsa-miR-139 or a mimetic thereof.

52. The method, use, composition, or kit according to paragraph 49, wherein the second agent targets and inhibits expression or activity of a transcription factor selected from the group consisting of IRF1 and ETV6.

53. The method, use, composition, or kit according to paragraph 49, wherein the second agent targets and inhibits expression or activity of IRF1; and the method or use further comprises administering or use of a third agent that targets and inhibits expression or activity of ETV6.

54. The method, use, composition, or kit according to any one of paragraphs 52-53, that further comprises administering or use of a fourth agent selected from the group consisting of hsa-miR-181d, hsa-miR-139, mimetics thereof, and combinations thereof.

55. The method, use, composition, or kit according to any one of paragraphs 40-48, wherein the first agent targets IRF1 and inhibits IRF1 expression or activity.

56. The method, use, composition, or kit according to paragraph 55, wherein the second agent comprises at least one agent selected from the group consisting of hsa-miR-133a, hsa-miR-181d, mimetics thereof, and combinations thereof.

57. The method, use, composition, or kit according to paragraph 55, wherein the second agent comprises hsa-miR-133a or a mimetic thereof, and the method further includes administering or use of a third agent that comprises hsa-miR-181d or a mimetic thereof.

58. The method, use, composition, or kit according to paragraph 55, wherein the second agent targets and inhibits expression or activity of a transcription factor selected from the group consisting of IKZF1, ELF1, and ETV6.

59. The method, use, composition, or kit according to paragraph 58 that further comprises administering or use of a third agent that is different from the second agent and that targets and inhibits expression or activity of a transcription factor selected from the group consisting of IKZF1, ELF1, and ETV6. In some embodiments the third agent inhibits expression or activity of a different TF than the second agent.

60. The method, use, composition, or kit according to paragraph 58, wherein the second agent targets and inhibits expression or activity of ELF1, and the method or use further comprises administering or use of a third agent that targets and inhibits expression or activity of a transcription factor selected from the group consisting of IKZF1, PPARG, and ETV6.

61. The method, use, composition, or kit according to any one of paragraphs 58-60 that further comprises administering or use of a fourth agent selected from the group consisting of hsa-miR-133a, hsa-miR-181d, mimetics thereof, and combinations thereof.

62. The method, use, composition, or kit according to any one of paragraphs 40-48, wherein the first agent targets ETV7 and inhibits ETV7 expression or activity.

63. The method, use, composition, or kit according to paragraph 62, wherein the second agent comprises at least one agent selected from the group consisting of hsa-miR-181d and mimetics thereof.

64. The method, use, composition, or kit according to paragraph 62, wherein the second agent targets and inhibits expression or activity of a transcription factor selected from the group consisting of PPARG, ZIC5, ELF1.

65. The method, use, composition, or kit according to paragraph 64 that further comprises administering or use of a third agent that differs from the second agent and that targets and inhibits expression or activity of a transcription factor selected from the group consisting of PPARG, ZIC5, ELF1. In some embodiments the third agent inhibits expression or activity of a different TF than the second agent.

66. The method, use, composition, or kit according to paragraph 62, wherein the second agent targets and inhibits expression or activity of ELF1; and the method or use further comprises administering or use of a third agent that targets and inhibits expression or activity of a transcription factor selected from the group consisting of PPARG, ZIC5, ETV6.

67. The method, use, composition, or kit according to any one of paragraphs 64-66 that further comprises administering or use of a fourth agent selected from the group consisting of hsa-miR-181d and mimetics thereof.

68. The method, use, composition, or kit according to any one of paragraphs 40-48, wherein the first agent targets and inhibits expression or activity of ETV6; and the second agent targets and inhibits expression or activity of a transcription factor selected from ELF1 and ELK3.

69. The method, use, composition, or kit according to any one of paragraphs 40-48, wherein the first agent targets and inhibits expression or activity of KLF17; and the second agent targets and inhibits expression or activity of KLF1.

70. The method, use, composition, or kit according to any one of paragraphs 40-48, wherein the first agent targets PPARG and inhibits PPARG expression or activity; and wherein the second agent either (i) targets and inhibits ELF1 expression or activity; or (ii) comprises hsa-miR-106b or a mimetic thereof.

71. The method, use, composition, or kit according to any one of paragraphs 40-48, wherein the first agent comprises hsa-miR-106b or a mimetic thereof; and wherein the second agent comprises hsa-miR-17-5p or a mimetic thereof.

72. The method, use, composition, or kit according to paragraph 71, further comprising: administering or use of a third agent that comprises hsa-miR-106b or a mimetic thereof; and administering or use of a fourth agent that comprises hsa-miR-130b or a mimetic thereof.

73. The method, use, composition, or kit according to any one of paragraphs 40-48, wherein the first agent comprises hsa-miR-19a or a mimetic thereof; and wherein the second agent comprises hsa-miR-19b or a mimetic thereof.

74. The method, use, composition, or kit according to any one of paragraphs 40-48, wherein the first agent comprises hsa-miR-181d or a mimetic thereof; and wherein the second agent comprises hsa-miR-324-5p or a mimetic thereof.

75. The method, use, composition, or kit according to any one of paragraphs 40-48, wherein the first agent comprises hsa-miR-181d or a mimetic thereof; wherein the second agent comprises hsa-miR-181a-3p or a mimetic thereof; and wherein the method or use further comprises administering or use of a third agent that comprises hsa-miR-128a or a mimetic thereof.

76. The method, use, composition, or kit according to any one of paragraphs 40-48, wherein the first agent comprises hsa-miR-139 or a mimetic thereof; wherein the second agent comprises hsa-miR-138 or a mimetic thereof; wherein the method or use further comprises administering or use of a third agent that comprises hsa-miR-133a or a mimetic thereof; and administering or use of a fourth agent that comprises hsa-miR-133b or a mimetic thereof.

77. The method, use, composition, or kit according to any one of paragraphs 40-48, wherein the first agent targets and inhibits expression or activity of hsa-miR-142-5p; and wherein the second agent targets and inhibits expression or activity of hsa-miR-223.

78. The method, use, composition, or kit according to paragraph 77, further comprising administering or including a third agent that targets and inhibits expression or activity of hsa-miR-146b.

79. The method, use, composition, or kit according to paragraph 78, further comprising administering or including a fourth agent that targets and inhibits expression or activity of hsa-miR-152.

80. The method, use, composition, or kit according to paragraph 78 or 79, further comprising administering or including a fifth agent that targets and inhibits expression or activity of hsa-miR-34a.

81. The method, use, composition, or kit according to paragraph 77, further comprising administering or including a third agent that targets and inhibits expression or activity of hsa-miR-27a.

82. The method, use, composition, or kit according to paragraph 81, further comprising administering or including a fourth agent that targets and inhibits expression or activity of hsa-miR-513.

83. The method, use, composition, or kit according to paragraph 82, further comprising administering or including a fifth agent that targets and inhibits expression or activity of hsa-miR-452.

84. The method, use, composition, or kit according to paragraph 83, further comprising administering or including a sixth agent that targets and inhibits expression or activity of transcription factor ZNF217.

85. The method, use, composition, or kit according to paragraph 81, further comprising administering or including a fourth agent that targets and inhibits expression or activity of hsa-miR-23a.

86. The method, use, composition, or kit according to any one of paragraphs 40-48, wherein the first agent targets and inhibits expression or activity of hsa-miR-15b; and wherein the second agent targets and inhibits expression or activity of hsa-miR-25.

87. The method, use, composition, or kit according to any one of paragraphs 40-48, wherein the first agent targets and inhibits expression or activity of hsa-miR-15b; and wherein the second agent targets and inhibits expression or activity of transcription factor TCF3.

88. The method, use, composition, or kit according to any one of paragraphs 40-48, wherein the first agent targets and inhibits expression or activity of hsa-miR-23a; and wherein the second agent targets and inhibits expression or activity of transcription factor TBX10.

89. The method, use, composition, or kit according to any one of paragraphs 40-48, wherein the first agent targets and inhibits expression or activity of transcription factor SMAD9; and wherein the second agent targets and inhibits expression or activity of transcription factor TFCP2L1.

90. The method, use, composition, or kit according to any one of paragraphs 40-48, wherein the first agent targets and inhibits expression or activity of hsa-miR-34a; and wherein the second agent targets and inhibits expression or activity of hsa-miR-146b.

91. The method, use, composition, or kit according to any one of paragraphs 40-48, wherein the first agent targets and inhibits expression or activity of hsa-miR-27a; wherein the second agent targets and inhibits expression or activity of hsa-miR-513; and wherein the method, use, composition, or kit further comprises administering or includes a third agent that targets and inhibits expression or activity of hsa-miR-23a.

92. The method, use, composition, or kit according to any one of paragraphs 40-48, wherein the first agent targets and inhibits expression or activity of transcription factor KLF6; wherein the second agent targets and inhibits expression or activity of transcription factor CEBPE; and wherein the method, use, composition, or kit further comprises administering or includes a third agent that targets and inhibits expression or activity of transcription factor CEBPD.

93. The method, use, composition, or kit according to any one of paragraphs 40-48, wherein the first agent targets and inhibits expression or activity of transcription factor TFAP2C; wherein the second agent targets and inhibits expression or activity of hsa-miR-34a; and wherein the method, use, composition, or kit further comprises administering or includes a third agent that targets and inhibits expression or activity of transcription factor RARG.

94. A method of treatment of a mammalian subject who has been diagnosed with glioblastoma multiforme (GBM), the method comprising: administering to the subject a first agent that inhibits an oncogene or inhibits a protein encoded by the oncogene; and administering to the subject a second agent comprising a microRNA (miRNA) or miRNA mimetic that targets messenger RNA (mRNA) encoded by the oncogene; wherein the oncogene is selected from the group consisting of VEGFR1 (FLT1), HDAC5, and VEGFR2 (KDR); and wherein the agents are administered in synergistically effective amounts.

95. Use of two or more agents to treat a mammalian subject who has been diagnosed with glioblastoma multiforme (GBM), or for the manufacture of a medicament to treat a mammalian subject who has been diagnosed with GBM, wherein a first agent inhibits an oncogene or inhibits a protein encoded by the oncogene; wherein a second agent comprises a microRNA (miRNA) or miRNA mimetic that targets messenger RNA (mRNA) encoded by the oncogene; wherein the oncogene is selected from the group consisting of VEGFR1 (FLT1), HDAC5, and VEGFR2 (KDR); and wherein the agents are used in synergistically effective amounts.

96. The method or use according to any one of paragraphs 94-95, wherein the mammalian subject is human.

97. The method or use according to any one of paragraphs 94-96, wherein the oncogene is HDAC5, the first agent is selected from the group consisting of romidepsin and Vorinostat (suberanilohydroxamic acid), and combinations thereof, and the second agent is selected from the group consisting of miR-486-3p, miR-506, mimetics thereof, and combinations thereof.

98. The method or use according to any one of paragraphs 94-96, wherein the oncogene is VEGFR1 or VEGFR2, and the first agent is selected from the group consisting of receptor tyrosine kinase inhibitors and VEGF traps.

99. The method or use according to paragraph 98, wherein the first agent is a VEGF trap selected from a VEGF antibody and a soluble VEGF receptor.

100. The method or use according to paragraph 99, wherein the first agent comprises Bevacizumab or Aflibercept.

101. The method or use according to paragraph 98, wherein the first agent is a receptor tyrosine kinase inhibitor selected from the group consisting of Axitinib, cediranib, pazopanib, Pegaptanib, ponatinib, Regorafenib, Sorafenib, sunitinib, Vandetanib, Vatalanib, antibodies that bind to the extracellular domain of VEGFR1, antibodies that bind to the extracellular domain of VEGFR2, and combinations thereof.

102. The method or use according to any one of paragraphs 98-101, wherein the second agent is selected from the group consisting of miR-578, miR-892b, mimetics thereof, and combinations thereof.

Aspects of the invention that have been described herein as methods also can be described as "uses," and all such uses are contemplated as aspects of the invention. Likewise, compositions described herein as having a "use" can alternatively be described as processes or methods of using, which are contemplated as aspects of the invention.

Reference throughout this specification to "one embodiment", "some embodiments" or "an embodiment" means that a particular feature, structure or characteristic described in connection with the embodiment is included in at least one embodiment of the present disclosure. The particular features, structures, or characteristics described herein may be combined in any suitable manner, and all such combinations are contemplated as aspects of the invention.

Unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

The invention includes, as an additional aspect, all embodiments of the invention narrower in scope in any way than the variations defined by specific paragraphs above. For example, where certain aspects of the invention that are described as a genus or set, it should be understood that every member of a genus or set is, individually, an aspect of the invention. Likewise, every individual subset is intended as an aspect of the invention. By way of example, if an aspect of the invention is described as a members selected from the group consisting of 1, 2, 3, and 4, then subgroups (e.g., members selected from {1,2,3} or {1,2,4} or {2,3,4} or {1,2} or {1,3} or {1,4} or {2,3} or {2,4} or {3,4}) are contemplated and each individual species{1} or {2} or {3} or {4} is contemplated as an aspect or variation of the invention. Likewise, if an aspect of the invention is characterized as a range, such as a temperature range, then integer subranges are contemplated as aspects or variations of the invention.

The headings herein are for the convenience of the reader and not intended to be limiting. Additional aspects, embodiments, and variations of the invention will be apparent from the Detailed Description and/or Drawing and/or claims.

Although the Applicant invented the full scope of the invention described herein, the Applicant does not intend to claim subject matter described in the prior art work of others. Therefore, in the event that statutory prior art within the scope of a claim is brought to the attention of the Applicant by a Patent Office or other entity or individual, the Applicant reserves the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 1A: Promoter regions of genes (±5 Kbp of the transcriptional start site (TSS)) were searched for DNA sequences that significantly matched a TF DNA recognition motif. DNAse I hypersensitivity hotspots were used to provide information about which regions of a promoter have open chromatin. DGF footprints were used to provide a means to empirically determine the genome-wide occupancy of DNA by TFs and other factors at nucleotide resolution. The requirement that a DGF footprint overlaps with a motif instance was used to exclude a large fraction of motif instances that are unlikely to be bound by a TF. FIG. 1B: We compared our predicted TF-target gene interactions to empirically determined TF binding from ChIP-seq studies. FIG. 1C: TF or miRNA-target gene predictions were compiled into a database (TF-target gene database described in A and miRNA-target gene databases are PITA and TargetScan). Mechanistically based TF- and miRNA-mediated regulation were inferred by integrating the target gene databases into the newly developed set enrichment scoring module for cMonkey$_2$ which systematically retains and adds co-expressed target genes of an enriched regulator.

FIG. 2A: Comparisons of ROC AUCs from increasing upstream promoter lengths were made relative to the core promoter size of ±500 bp. A promoter length exceeding the red line indicates a significant reduction in ROC AUC (p-value <0.05). FIG. 2B: Comparisons of ROC AUCs from increasing downstream promoter lengths were made relative to the promoter size of −5 Kbp and +500 bp. A promoter length exceeding the red line indicates a significant reduction in ROC AUC (p-value <0.05). FIG. 2C: Filtering predicted transcription factor binding sites through DGF significantly increases sensitivity and specificity for predicting TF from ENCODE ChIP-seq studies. Each line is a ROC curve of the comparison to the ENCODE ChIP-seq studies. AUC=area under the curve.

FIGS. 3A-3C. Diagram of flow and input for SYGNAL pipeline and summary of TF and miRNA regulatory predictions for gbmSYGNAL TRN. FIG. 3A: Input data from TOGA and independent validation cohorts were integrated into the SYGNAL pipeline. cMonkey$_2$ was used to reduce dimensionality and discover mechanistic TF and miRNA regulatory predictions. Biclusters were then filtered based on: 1) significant co-expression and validation in at least one independent cohort; and 2) either significant association of bicluster eigengene with patient survival and validation in independent cohort in same direction, or enrichment of the bicluster genes with a hallmark of cancer. Then, NEO was used to infer causal flows of information from a mutation or mutated pathway to a TF or miRNA to a bicluster. The enrichment of a motif in the promoters of bicluster genes was tested using AME and used as a secondary method to discover causal and mechanistic TF regulators. FIG. 3B: Summary of transcription factor (TF) to bicluster regulatory predictions from SYGNAL pipeline and number of TFs discovered at each step. First, cMonkey$_2$ was used to discover mechanistic regulatory predictions. Then each TF was expanded to a list of family members and only those with a significant correlation with the bicluster eigengene were retained. Causal TFs were discovered through NEO. Finally, causal and mechanistic TFs were discovered by overlapping the cMonkey$_2$ and NEO predicted TF regulators or through significant enrichment of causal TF motif instances in the promoters of bicluster genes. FIG. 3C: Summary of miRNA to bicluster regulatory predictions and number of miRNAs discovered at each step. Mechanistic miRNA regulatory predictions were discovered using cMonkey$_2$ and only those miRNAs which were anti-correlated with the bicluster eigengene were retained. Causal miRNA regulators were required to have a negative effect of the miRNA on a bicluster. Finally, causal and mechanistic miRNA regulators were discovered by overlapping the cMonkey$_2$ and NEO discovered miRNA regulators (* overlapping causal and mechanistic miRNAs were not required to be predicted for the same bicluster).

FIGS. 4A-4D. Network of combinatorial TF and miRNA regulatory interactions, effect of combined knock-down of TF pairs on proliferation, and emergent transcriptional signature underlying the synergistic phenotypic effect of ETV6 and NFKB1 single and double knock-down on proliferation. FIG. 4A: Edges link TFs and miRNAs found together in at least one combinatorial regulatory model, and legend describes additional information overlays. FIG. 4B: Effect of combinatorial TF knock-down with siRNA on proliferation. Single TF knock downs for each pair (yellow and blue bars) were used to compute Bliss additive expected combined effect (light green bar) which is compared to the experimentally observed effect (dark green bar). If the observed effect is greater than the expected the effect is synergistic, if it is less than the expected then it is antagonistic, and if it is equivalent then the effect is considered additive. FIG. 4C: Significant overlap of 48 genes with higher expression following double knock-down of ETV6 and NFKB1 with the overlapping 247 genes with significantly lower expression following single knock-down of either TF (p-value $<2.2\times10^{-16}$). FIG. 4D: Fold-change for 48 genes significantly lower following ETV6 or NFKB1 single TF knock-down and become significantly higher expression following double knock-/down of ETV6 and NFKB1. KD=knock-down; Exp. Comb.=expected combination effect size; Obs. Comb.=observed combination effect size; Comb.=combination; ns=not significant; *=antagonistic effect with p-value ≤0.05; =antagonistic effect with p-value ≤0.01; *=antagonistic effect with p-value ≤0.001; ##=synergistic effect with p-value ≤0.01.

FIG. 5A: Therapeutic indication (over-expression or knock-down) of a TF or miRNA regulating a bicluster is determined by considering both the direction of association between bicluster expression and patient survival, and the direction of correlation bicluster expression and the predicted regulator. This decision tree was applied to each bicluster with at least one predicted regulator. Then survival analysis is used to determine if increased expression of the bicluster eigengene is associated with decreased (positive coefficient) or increased (negative coefficient) patient survival. Then whether the predicted regulator functions as an activator or repressor is used to determine the therapeutic indication of whether the predicted TF or miRNA should be over-expressed or knocked-down to increase patient survival. FIG. 5B: Determining the most likely responders based on GBM subtype(s) for therapeutic intervention with a predicted regulator is determined based on a combination of the direction of the association with patient survival and subtype enrichment in the specified tail of bicluster expression. When shorter survival is associated with higher bicluster expression the enrichment in the fifth quintile is used to determine the most likely responders (red box). FIG. 5C: When shorter survival is associated with lower bicluster expression the enrichment in the fifth quintile is used to determine the most likely responders (orange box).

DETAILED DESCRIPTION

Figure 1A:
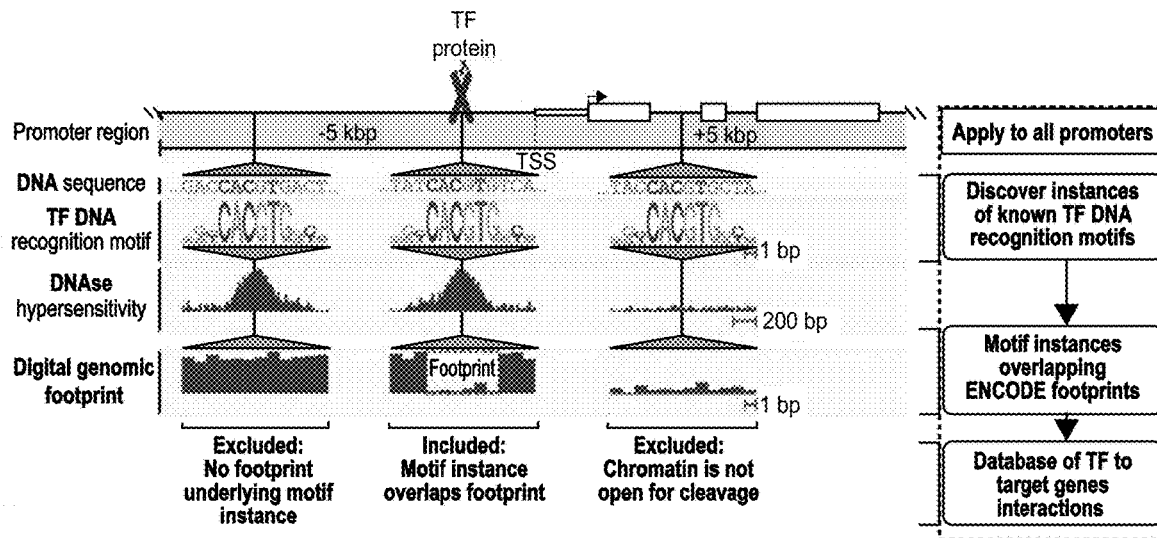
FIGS. 1A-1C. Construction of genome-wide TF-target gene interaction database by integrating genomic sequence, TF DNA recognition motifs, and DGF footprints.

Unless otherwise defined by explicit definition or example, scientific and technical terms have their usual and customary meaning as commonly understood by scientists in the field.

In the context of methods of treatment, ordinals describing an agent (e.g., "first agent," "second agent," "third agent") are used to uniquely identify and distinguish one agent from another and to indicate that the agents are different from each other, but are not intended to imply an order or a priority for the agents or steps of a method that employ them. Because in this circumstance the ordinals do not imply an order, it is possible to characterize embodiments of the invention with discontinuous ordinals (e.g., an embodiment with defined first, second, and fourth agents is simply an embodiment with three uniquely defined agents (with no implication that a "third" uniquely defined agent must be present).

Ordinals used to describe steps of a method (e.g., "first administering," "second administering") are indicative of an order of steps.

An agent "targets" a gene regulator if the agent interacts directly with the gene regulator (e.g., binds to the gene regulator) or indirectly (e.g., modulates expression or activity of the gene regulator). Examples of modulation of expression include interacting with the gene encoding the gene regulator to increase or decrease gene transcription, or interacting with mRNA to increase or decrease mRNA degradation or translation to protein (if the gene regulator is a protein). Examples of modulating activity of a gene regulator include interfering with binding between a gene regulator and its target, e.g., by binding to the gene regulator or binding to a target of the gene regulator.

In the context of administration of two or more agents, "synergistically effective amounts" are amounts of the agents that either (i) produce greater than additive therapeutic effects, compared to monotherapy with the agents; or (ii) produce at least comparable therapeutic effects and reduce toxic side effects, due to lower effective dosing or less frequent dosing, compared to monotherapy with the agents. An indication of such synergy can be provided in in vitro studies, e.g., with GBM cell lines, in studies to evaluate the killing of tumor cell lines in vitro or inhibition of cell growth. Synergy can be demonstrated in clinical trials in which the effects of monotherapy and combination therapy are compared and statistically analyzed.

A "mammalian subject" can be any mammal. Particularly contemplated are animals of agricultural importance, such as bovine, equine, and porcine animals; animals important as domestic pets, including canines and felines; animals important in research, including rodents and primates; large endangered species and zoo animals such as primates, felines, giraffes, elephants, rhinos. Especially contemplated are humans.

"Omics" refers to fields of study or collections of data that characterize multiple biological molecules, sometimes relative to each other, in the context of cells or organisms. Examples include genomics (evaluation/data pertaining to the genome of a cell or organism); proteomics (proteins); metabolomics (metabolites); transcriptome (RNA molecules); and other specialized classes of information, such as information about subsets or subtypes of any of the foregoing). Omics data may contain information about hundreds or thousands of species within a class of molecule. "Multi-omics" data refers to more than one type of omics data.

Overview of Strategy for Identifying Combination Therapeutic Interventions

We hypothesized that knowledge of the detailed architecture of transcription factor (TF) and miRNA regulatory interactions in the form of a transcriptional regulatory network (TRN) would provide the mechanistic details required to prioritize combinatorial interventions. Both TFs (Cai et al., 1996) and, more recently, miRNAs (Bouchie, 2013) have been used as therapeutic targets. In fact, consistent with the situation ~20 years ago (Cai et al., 1996), therapies targeting TFs still comprise 14% of the top 50 best-selling FDA approved drugs in 2014. Additionally, therapies targeting TFs and miRNAs have the potential for a broader effect than those targeting a single gene, as these regulators control many genes associated with diverse oncogenic biological processes.

Previous efforts on the inference of TRNs for cancers have relied on the discovery of correlates or mutual information between different features within multiomics datasets from patient tumors (Carro et al., 2010; Sumazin et al., 2011). Additionally, genetic markers have been used as anchors for dissecting causal relationships between traits (Chen et al., 2014; Jornsten et al., 2011). Mechanism-based strategies have also been developed and applied to inference of miRNA and TF regulation in cancers (Goodarzi et al., 2009; Reiss et al., 2015). Many of the foregoing approaches are complementary and have yet to be integrated into a unified TRN inference pipeline.

Characteristics of TRN inference approaches applied to GBM.

| Studies | TF | miRNA | Linear | Mutual Information | Mechanistic | Causal | Incorporate Mutations |
|---|---|---|---|---|---|---|---|
| Carro et al., 2010 | X | | X | X | | | |
| Sumazin et al., 2011 | | X | | X | X | | X |
| Chen et al., 2014 | X | | | X | | X | X |
| Jörnsten et al., 2011 | | | | | | | |
| Goodarzi et al., 2009 | X | X | | X | X | | |
| Reiss et al., 2015 | | X | X | | X | | |
| SYGNAL Pipeline | X | X | X | | X | X | X |

Modeling of Regulatory Interactions [A]

[A] Either of these should be sufficient, major difference is underlying assumptions of distributions are different.

We developed the SYstems Genetic Network AnaLysis (SYGNAL) pipeline (bottom line of table above) to integrate correlative, causal and mechanistic inference approaches into a unified framework that systematically infers the causal flow of information from mutations to TFs and miRNAs to perturbed gene expression patterns across patient tumors.

Importantly, the algorithms behind each component of the SYGNAL pipeline has been rigorously tested and validated in prior studies (Aten et al., 2008; Brooks et al., 2014; Friedman et al., 2009; Kertesz et al., 2007; Reiss et al., 2015). We have applied this pipeline to construct a GBM TRN and have extensively validated the TF and miRNA regulatory predictions, including combinatorial regulatory interactions. We demonstrate how this detailed map of disease-perturbed gene regulation derived from patient data can be used to prioritize TFs, miRNAs and drugs to tailor single and combinatorial interventions. Finally, we demonstrate how the GBM TRN can be used to glean new biological insights with a vignette focusing on the regulation of tumor lymphocyte infiltration in GBM, one of the significant findings from our network analysis.

Computer-Implemented Method for Identifying Treatment Targets

Figure 6:
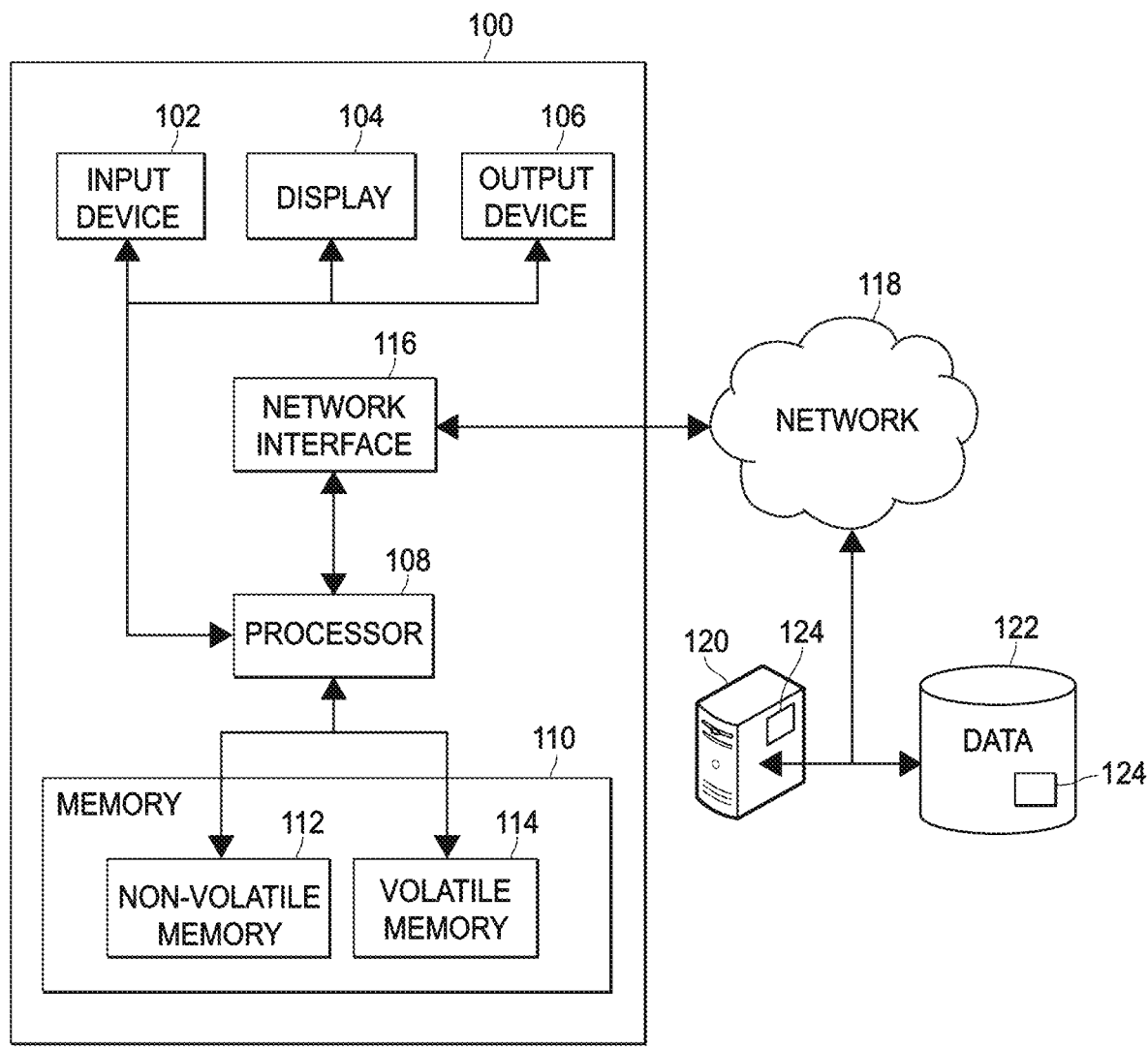
FIG. 6 is a block diagram depicting an example computer programmed to implement a method in accordance with the present description.

FIG. 6 depicts a block diagram of an example computer 100 programmed to implement a method in accordance with the present description. The computer 100 includes one or more input device(s) 102, one or more display device(s) 104, one or more output device(s) 106, and one or more processor(s) 108. Each of the input devices 102 may be any known input device including, without limitation, a pointing device (e.g., a keyboard, a mouse, a track pad, a touch screen, etc.) that allows a user to operate and provide input to the computer 100. The input devices 102 may be internal (as in the case of a laptop computer) or external (as in the case of a USB mouse) to the computer 100, may be hard-wired to or removable from the computer, and may utilize any protocol that facilitates communication between the input device 102 and the processor(s) 108.

Similarly, the display(s) 104 and the output device(s) 106 may be internal (as in the case of a laptop display) or external (as in the case of a USB monitor or a printer), may be hard-wired to or removable from the computer, and may utilize any protocol that facilitates communication between the display(s) 104 and output device(s) 106 and the processor(s) 108. Of course, the displays 104 can utilize any known technology. Additionally, in embodiments, the display 104 may be coupled to and/or integrated with the input device 102, as would be the case in a touch-screen.

As will be understood, the processor(s) 108 may be one or more individual distinct processor packages, may be an integrated multi-core processor in a single package, or may even be multiple multi-core processor packages. The processor(s) 108 are programmed and/or programmable to perform the methods described below, according to machine readable instructions. The machine readable instructions may be stored on one or more memory device(s) 110 comprising any type of tangible, non-transitory media (e.g., magnetic media, solid state media, optical media, etc.) capable of storing data and/or machine-readable instructions executable by the processor 108. The memory 110 may have one or more elements of non-volatile memory 112 (e.g. solid state memory, hard drive, etc.) and one or more elements of volatile memory (e.g., Random Access Memory, or RAM) 114.

The processor 108 may also be communicatively coupled to a network interface 116. The network interface 116 is operable to communicate with one or more network devices via a communication protocol over a network 118. The network interface 116 may be communicatively coupled with the network 118 via any known (or later developed) wired or wireless technology, including without limitation, Ethernet networks, networks adhering to the IEEE 802.11 family of protocols, etc. The network 118, of course, may be any local or wide area network including, for example, the Internet, and may provide access to data (including machine-readable instructions, in embodiments) stored on one or more servers 120 and/or databases 122. In this manner, the processor 108 may retrieve, via the network interface 116 and the network 118, collections 124 of data stored on the servers 120 and/or the databases 122, which collections 124 of data may be updated periodically or in real time, in various embodiments. As a result, and as will be understood in view of the description to follow, the processor 108 may execute the methods described herein using the most recent collections 124 of data available as inputs, and/or may receive updated algorithms and/or computer-readable instructions for use in those methods. Of course, data retrieved via the network 118 may be stored in either or both of the non-volatile memory 112 and the volatile memory 114 for later access and/or manipulation by the processor 108 and/or for comparison to current data stored on the servers 120 and/or the databases 122, in making a determination as to whether the one or more of the collections 124 of data have been updated since they were last retrieved via the network 118.

The collections 124 of data stored on the servers 120 and/or the databases 122 may include, by way of example, various multi-omics data. Such data may include genomics data, transcriptomics data, catalogs of predicted targets such as microRNA (miRNA) targets, catalogs of predicted transcription factor (TF) targets, etc. In embodiments, the collections 124 of data include one or more of: the TargetScan database; the PITA database; multi-omics data from The Cancer Genome Atlas (TCGA) for one or more conditions (e.g., for glioblastoma multiforme—GBM); and a transcription factor target database as described with reference to FIG. 11.

Turning now to FIGS. 7-10 it should be understood that while the methods depicted in those figures will be described with reference to application of the method to a specific set of data (e.g., data related to glioblastoma multiforme), to map disease-relevant gene regulatory interactions for GBM, the method is applicable in other contexts and may be applied to mapping disease-relevant gene regulatory interactions for other cancers and/or for other non-cancer conditions, including but not limited to auto-immune conditions, allergic conditions, infections, inflammatory conditions, and graft-versus-host disease. It should also be understood that it is not, strictly speaking, necessary to perform each step described and/or depicted in the methods below as, in some circumstances, execution of a portion of the methods described herein may yield data that are useful in exploring potential treatments for the condition(s) in question.

FIGS. 7-10 depict a method 150 of deciphering transcriptional regulatory networks from multi-omic and clinical patient data. The method 150 applies a variety of known algorithms to a combination of known and newly constructed data sets, in a novel and advantageous sequence, as will be described below, to identify transcription factors (TFs) and micro-RNAs (miRNAs) to target and prioritize combinatorial disease interventions. For clarity, the method 150 depicts both data (inputs and outputs) and processes. In the FIGS. 7-10 (and in FIG. 11), processes are depicted as rectangles and have reference numerals in the range 200-299, while data sets (inputs to and outputs from the processes) are depicted as non-rectangular parallelograms and have reference numerals in the range 300-399. For the set of multi-omics data studied during development of the method 150, the number of members of each set of data is depicted in the upper right-hand corner of each data set block. It is worth noting that the method 150 could yield different results if one or more of the input data sets is updated.

Figure 7:
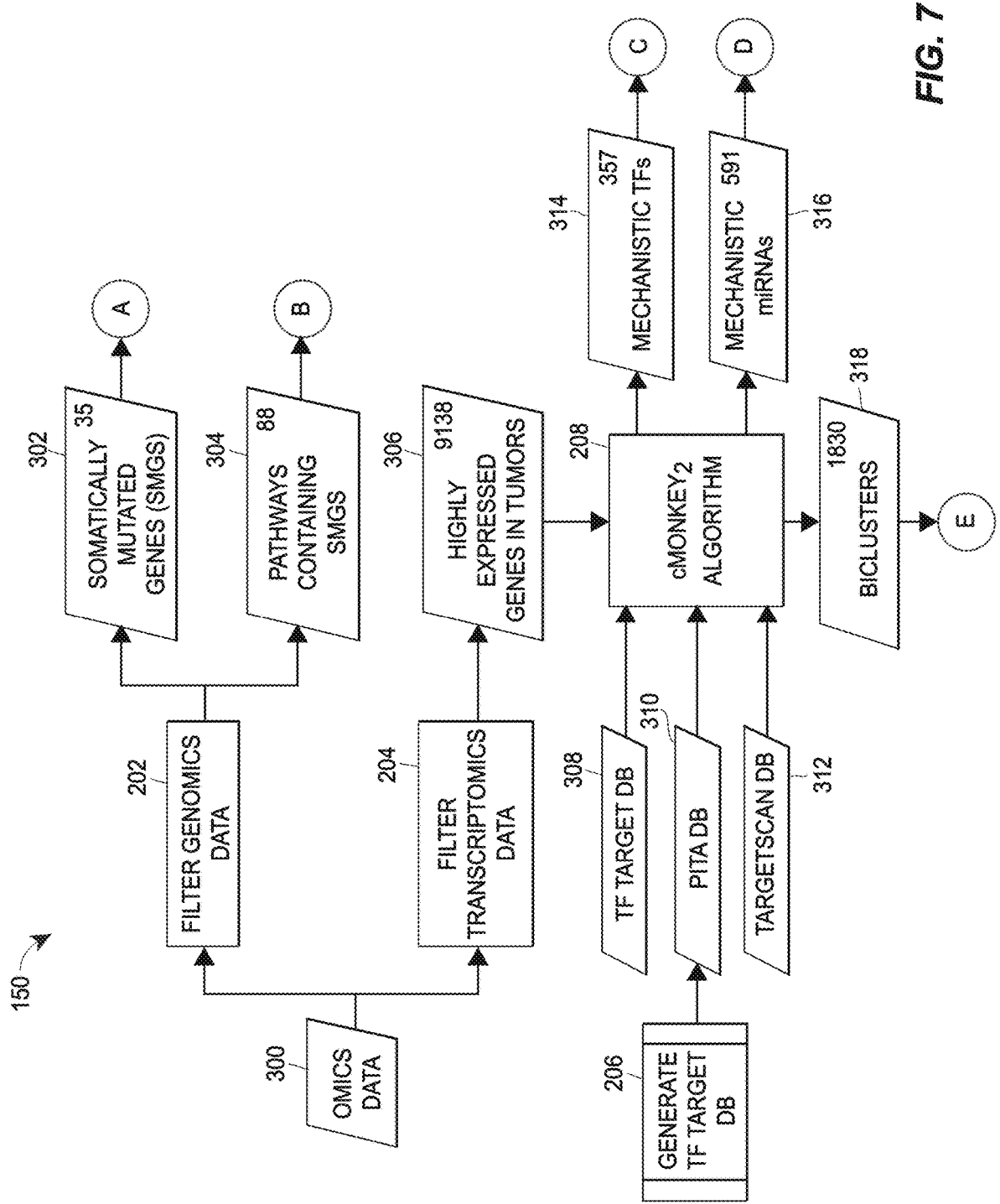
FIG. 7 is a flow chart depicting a portion of a method for identifying treatment targets in accordance with the present description.

Referring to FIG. 7, the method 150 generally starts with the acquisition of multi-omics data (data 300). As described herein, the multi-omics data (data 300) are, in an embodiment, directed to mapping disease-relevant gene regulatory interactions for GBM, a set of multi-omics data from The Cancer Genome Atlas (TCGA) for GBM. Of course other multi-omics data, whether or not from the TCGA, may serve as the multi-omics data (data 300) where the method 150 is being applied to map disease-relevant gene regulatory interactions for other diseases. Additionally, any given set of multi-omics data may be updated periodically to include a different (usually larger) set of patients and/or controls. In any event, the TCGA multi-omics data (data 300) include some or all of transcriptomics data, clinical survival data, and miRNA data and, in some sets of multi-omics data, genomics data.

The transcriptomics data of the multi-omics data (data 300) are filtered (process 204) to restrict the study to a set (data 306) of genes expressed at a level that was greater than or equal to the median expression of all genes across at least 50% of all tumors. The set (data 306) of highly expressed genes (9138 for this study) includes a number of TFs (788 in this study) and a number of miRNA regulators (534 in this study).

The filtered data (data 306) are input into the cMonkey2 algorithm (process 208). The cMonkey2 algorithm (process 208) identifies conditionally co-regulated modules of genes (biclusters). As should be understood, the cMonkey2 algorithm (process 208) will produce for a given number of input gene expression profiles a given number of co-regulated biclusters. For the filtered data (data 306) including 9138 genes in this study, the cMonkey2 algorithm (process 208) reduced the expression profiles to 610 co-regulated biclusters. The cMonkey2 algorithm (process 208) may be run multiple times on a set of input data (data 306), each time using a different training configuration. In the embodiment depicted in FIG. 7, the cMonkey2 algorithm (process 208) is run three times and, as a result, produces a set (data 318) of co-regulated biclusters three times in number of what a single run would produce. (Thus, for the GBM data, the cMonkey2 algorithm (process 208) produced a total of 1830 biclusters over three runs.) The first run used a TF-target gene interaction database (data 308) as input to the set-enrichment module of the cMonkey2 algorithm (process 208) to discover transcription factor-mediated (TF-mediated) regulation, and a corresponding set (data 314) of TF targets (357 in this case). The second and third runs of the cMonkey2 algorithm (process 208) used the PITA database (data 310) and TargetScan database (data 312) as input to the set-enrichment module to discover microRNA-mediated (miRNA-mediated) regulation, and a corresponding set (data 316) of miRNA regulators (591 in this case). While the PITA database (data 310) and TargetScan database (data 312) are known, the TF-target gene interaction database (data 308) is a novel database that integrates genomic sequence, TF DNA recognition motifs, and digital genomic footprints (DGFs), and is generated (process 206) for use with the method 150. A DGF constitutes experimental evidence that a DNA-binding protein was bound to a genomic location and, when coincident with an instance of a DNA recognition motif for a TF, suggests an interaction of a specific TF with that genomic location. DGFs are tissue- or cell-type specific. The TF target gene interaction database (data 308) constructed herein (process 206) includes the data for all cell and tissue types for which DGF data exist and, therefore, constitutes a single database allowing the cMonkey2 algorithm (process 208) to discover TF-mediated regulation related to any tissue or cell type.)

Figure 8:
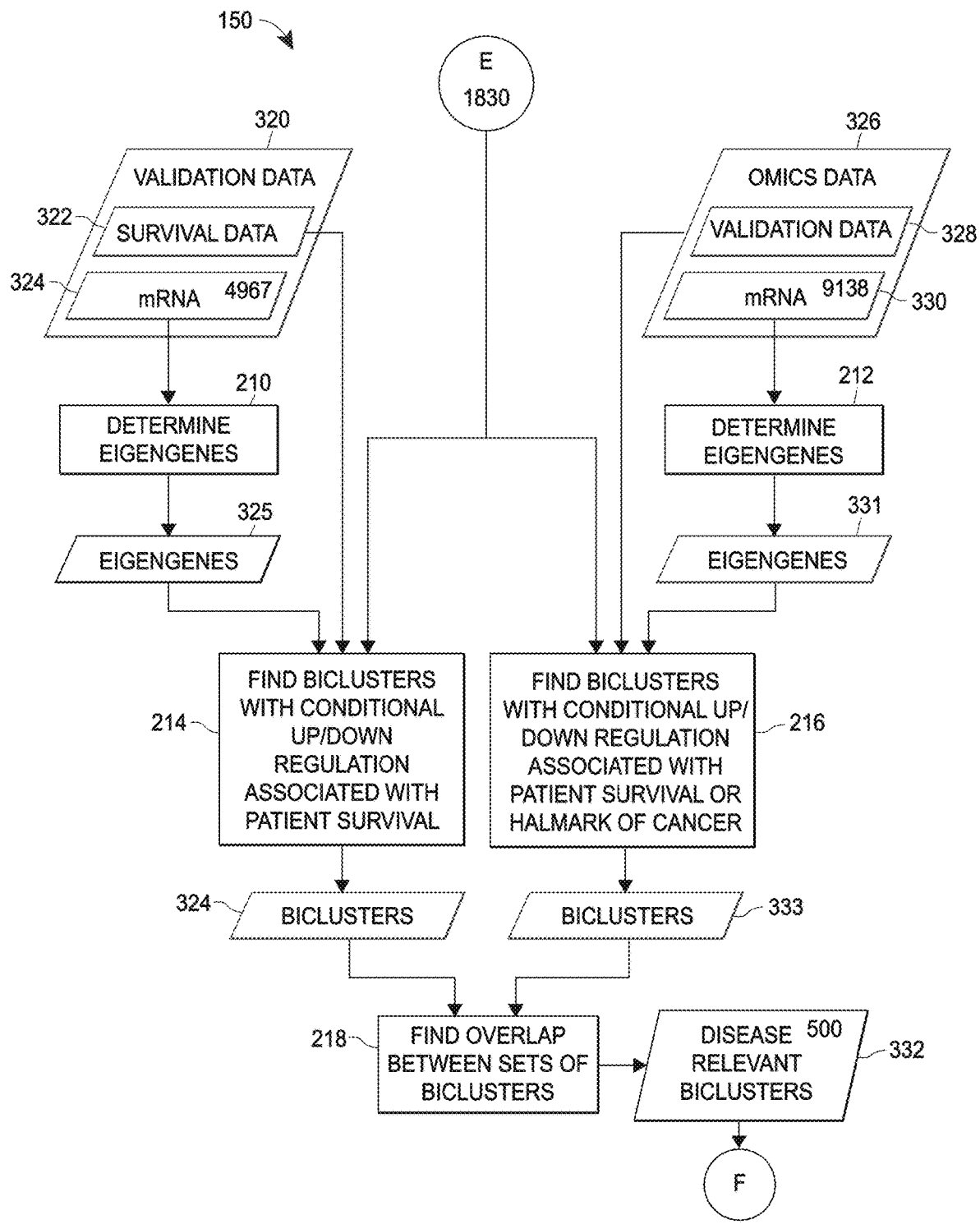
FIG. 8 is a flow chart depicting an additional portion of the method of FIG. 7.
Figure 9:
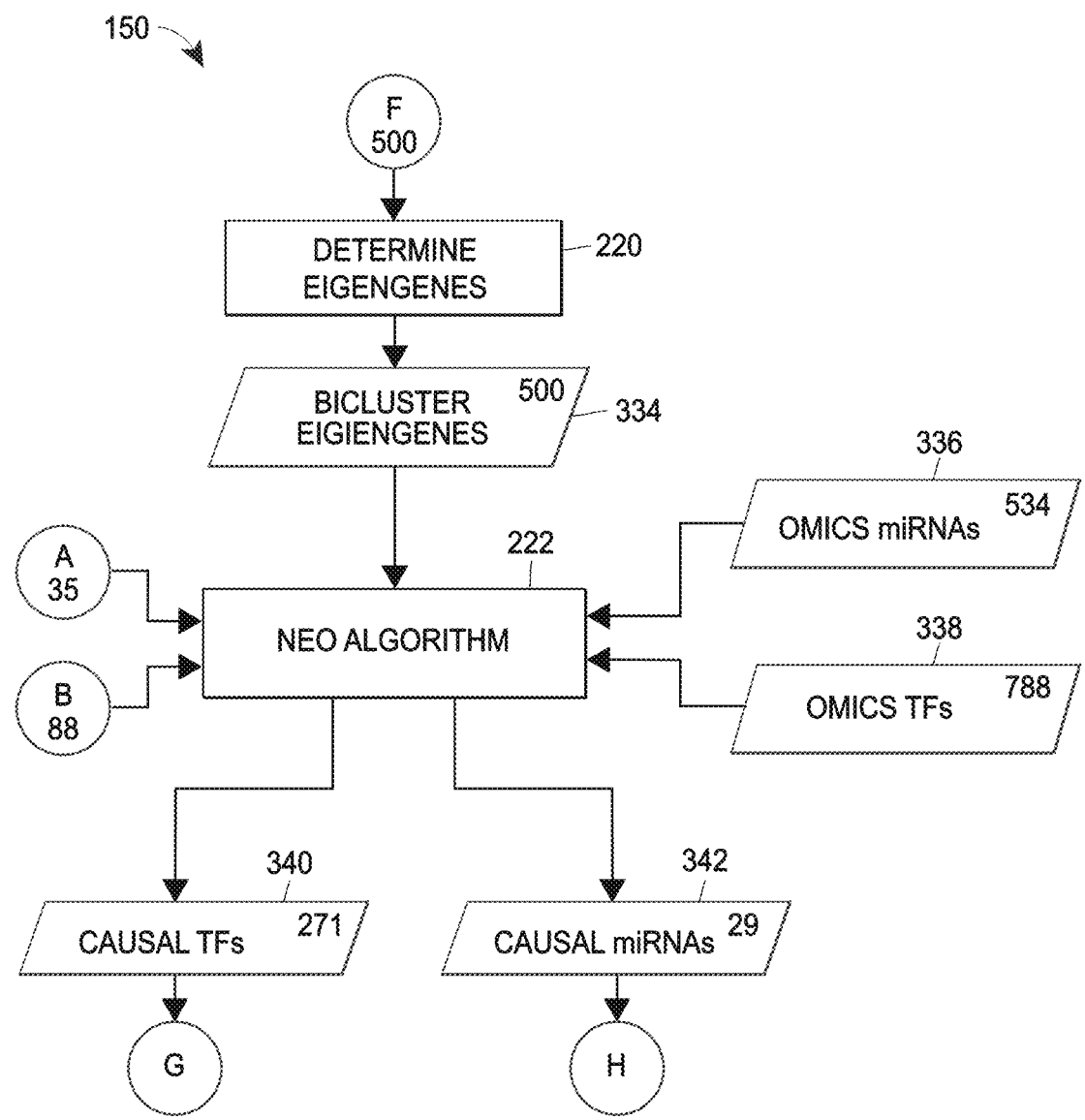
FIG. 9 is a flow chart depicting an additional portion of the method of FIGS. 7 and 8.

Turning now to FIG. 8, the biclusters (data 318) are post-processed to infer a mechanistic regulatory network. Generally speaking, the biclusters (data 318) are analyzed with respect to multi-omics data (data 326). The multi-omics data (data 326) may be a subset of the multi-omics data (data 300), and may include a set (data 328) of clinical survival data and a set (data 330) of mRNA data (9138 genes in this study), from the latter of which a set (data 331) of eigengenes is determined (process 212). Using the set (data 328) of clinical survival data and the set (data 331) of eigengenes, the biclusters (data 318) are analyzed (process 216) to find a set (data 333) of biclusters with conditional up/down regulation associated with either patient survival or one of the hallmarks of cancer.

The biclusters (data 318) are also analyzed with respect to one or more sets (data 320) of validation data. Each set (data 320) of validation data includes a set (data 322) of clinical survival data and a set (data 324) of mRNA data (4967 genes in the validation data used in this study), from the latter of which a set (data 325) of eigengenes is determined (process 210). Using the set (data 322) of clinical survival data and the set (data 325) of eigengenes, the biclusters (data 318) are analyzed (process 214) to find a set (data 327) of biclusters with conditional up/down regulation associated with patient survival in any of the one or more sets (data 320) of validation data.

The set (data 327) of biclusters identified from the validation data (data 320) and the set (data 333) of biclusters identified from the multi-omics data (data 326) are compared (process 218) to find a set (data 332) of disease relevant biclusters (in this study, 500 biclusters) identified in both analyses (i.e., biclusters that show up in both sets (data 327, data 333) of biclusters.) From a bicluster it is possible to discover a regulatory factor (TF or miRNA) that can be used as a therapeutic intervention point to modulate the activity of the bicluster genes. The therapeutic intervention direction can be determined using the approach described in FIG. 12.

The method 150 continues, in some (though not necessarily all) embodiments, with further analysis of the disease relevant biclusters (data 332). The disease relevant biclusters (data 332) are analyzed to determine the eigengenes of the biclusters (process 220), resulting in a set (data 334) of disease relevant bicluster eigengenes (500 in the instant study). The set (data 334) of disease relevant bicluster eigengenes is then analyzed using the Network Edge Orienting (NEO) algorithm (process 222) to infer causal flows of information from a mutation or mutated pathway to a TF or miRNA to a bicluster—that is, to evaluate whether somatic mutations causally affect TF or miRNA expression, which in turn causally affect the expression of co-regulated genes within a bicluster. The NEO algorithm (process 222) takes somatic mutations, TF or miRNA expression, and a bicluster eigengene (the first principal component of co-regulated genes within each bicluster) as input into structural equation models that compute causal edge orienting scores. Each score is a relative model fitting index for the causal model relative to alternative causal models, and larger scores are indicative of strong evidence that this causal orientation is correct. In an embodiment, a score is considered indicative of causality if the fit is at least three times better than that of the next best alternative model, though in other embodiments, other thresholds may be implemented to include weaker or only stronger indications of causality. The causality based approach adds somatically mutated genes and pathways to the Transcriptional Regulatory Network (TRN) by inferring that the mutations influence the expression of TFs and miRNAs, which in turn modulate the expression of their predicted target genes. It is worth noting that the inference of a causal model does not imply mechanistic linkages between the nodes, and therefore the intersection of mechanistic and causal inference approaches is very powerful evidence of regulation.

In order to compute the score using the NEO algorithm (process 222), the algorithm must be provided not only with the disease relevant bicluster eigengenes (data 334) to be scored, but also with the somatic mutations/pathways, and TFs and miRNAs against which the disease relevant bicluster eigengenes (data 334) will be scored. Referring again to FIG. 7, these data come from the multi-omics data (data 300). The multi-omics data (data 300) are filtered (process 202) to determine a set (data 302) of genes that are somatically mutated (in this case minor allele frequency ≥0.05, 35 genes), and a set (data 304) of pathways that contain one or more somatically mutated genes (in this case minor allele frequency ≥0.05, 88 pathways). In embodiments, a gene is considered to be mutated in a particular instance (e.g., in a patient's GBM tumor) if a somatic mutation is observed that modifies the gene's coding sequence (missense, nonsense, frame-shift, in-frame insertion or deletion, splice site, modifies translation start site, introduces new start site, or removes stop codon). In embodiments, a pathway was considered to include a SMG if at least one gene member of the pathway had a nonsynonymous somatic mutation. Referring again to FIG. 9, the TF expression data (data 336, 534 miRNAs in this study) and miRNA expression data (data 338) also come from the multi-omics data (data 300, 788 TFs in this study). With these data (data 302, 304, 336, and 338) the NEO algorithm (process 222) can analyze the disease relevant bicluster eigengenes (data 334) to predict a set (data 340) of causal TFs and a set (data 342) of causal miRNAs (271 and 29, respectively, in this study).

Figure 10:
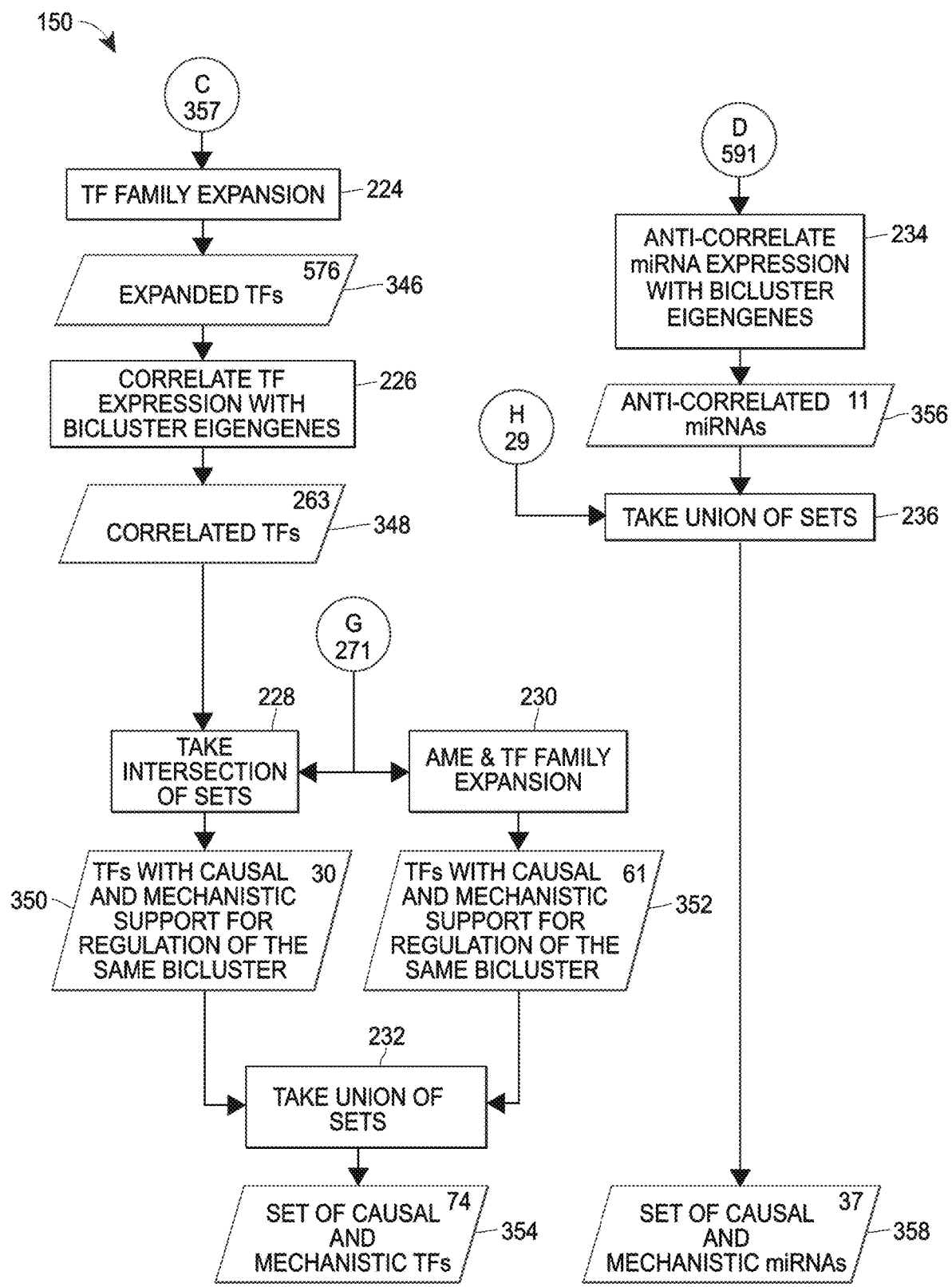
FIG. 10 is a flow chart depicting another portion of the method of FIGS. 7, 8, and 9.

With reference now to FIG. 10, the mechanistic TFs (data 314) output by the cMonkey2 algorithm (process 208) are expanded (process 224) according to family memberships. The precomputed TF target gene database (data 308) is limited to TFs with known DNA recognition motifs. By building upon the fact that families of TFs that have emerged through gene duplication events tend to have similar DNA recognition motifs, and assuming that the motifs within a TF family will not vary significantly, the predicted influences of a TF with a known DNA recognition motif can be extended to include family members that likely share a similar motif in a set (data 346) of expanded TFs. (In the present study, that yielded 576 expanded TFs.) Expression correlation between each member of the expanded TF family (data 346) and a target bicluster's eigengene is then used to discover the most likely regulator of genes in that bicluster (process 226) to yield a set (data 348) of correlated TFs (263 in the present study). The correlated mechanistic TFs (data 348) are compared with the causal TFs (data 340) output by the NEO algorithm (process 222) by taking the intersection of the two sets (process 228), to yield a set (data 350) of TFs with both causal and mechanistic support for regulation of the same bicluster (in this case 30 TFs), and implying that the genes in the bicluster share a common promoter sequence and are correlated with a TF that is being driven by a somatic mutation in the disease (GBM in this case).

The causal TFs (data 340) are also subjected to the analysis of motif enrichment (AME) algorithm (process 230) to determine if the motif for a causally inferred TF was significantly enriched in the promoter sequences of the genes from a bicluster (AME corrected p-value ≤0.05 and percent targets 50%), to yield a second set (data 352) of TFs with causal and mechanistic support for regulation of the same bicluster (in this case 61 TFs).

The two sets (data 350 and data 352) of TFs with causal and mechanistic support for the regulation of the same bicluster are combined (process 232) to yield a set (data 354) of causal and mechanistic TFs (74 in the present study). That is, the set (data 354) of causal and mechanistic TFs is the union of the first set (data 350) of TFs with both causal and mechanistic support for regulation of the same bicluster and the second set (data 352) of TFs with causal and mechanistic support for regulation of the same bicluster.

Similarly, the set (data 316) of mechanistic miRNAs (591 here) output by the cMonkey2 algorithm (process 208) are restricted (rather than expanded) because miRNAs typically act as repressors. Accordingly, the mechanistic miRNAs (data 316) are analyzed (process 234) to select only miRNAs that exhibit anti-correlated expression with bicluster eigengenes, to result in a set (data 356) of anti-correlated miRNAs (11 in this study). The set (data 356) of anti-correlated miRNAs is combined (process 236) with the set (data 342) of causal miRNAs output by the NEO algorithm (process 222) to yield a set (data 358) of causal and mechanistic miRNAs (37 in this study). That is, the set (data 358) of causal and mechanistic miRNAs is the union of the set (data 356) of anti-correlated miRNAs and the set (data 342) of causal miRNAs.

Figure 11:
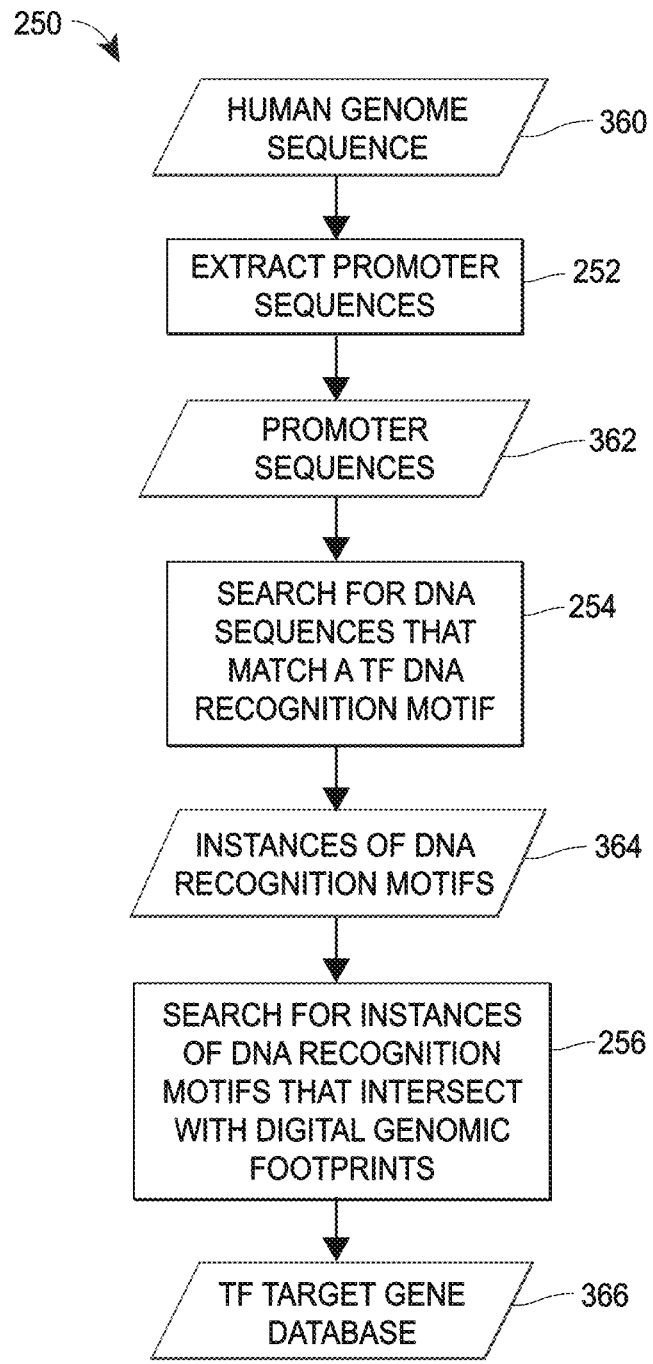
FIG. 11 is a flow chart depicting a method of generating a target database used as an input in the method depicted in FIG. 7.

With brief reference back to FIG. 7, the TF target database (data 308) that constitutes one set of training data for the cMonkey2 algorithm (process 208) is generated by a method 250 depicted in FIG. 11. When constructing the TF target database, the size of the sequence window surrounding the transcription start site (TSS)—the promoter region—in which to search for potential TF binding sites needs to be optimized. An excessively large window lowers the specificity of detection, whereas a window that is too small could exclude regions that contain bona fide TF binding locations. In an embodiment, the optimum promoter region is defined as the maximum sequence window surrounding the TSS that produces the same or greater sensitivity and specificity for predicting TF target gene interactions as the core promoter (i.e., ±500 bp of the TSS). The maximum is chosen as the optimum in this embodiment because we know that human TF target gene interactions can be separated by very long distances from the TSS both up- and down-stream from the TSS. To find the optimum region, the downstream (3') promoter boundary was fixed at +500 bp and the upstream (5') promoter boundary was varied (−1, −2.5, −5, −10, and −20 kbp). When a significant decrease in the sensitivity and specificity is observed beyond an increase of the upstream promoter boundary past a certain value (e.g., −5 kbp), the upstream promoter boundary is fixed at that value and the downstream promoter boundary is varied accordingly (e.g., +1, +2.5, +5, +10, +20 kbp) in the same manner (e.g., fixing the downstream promoter at +5 kbp). As a result, the optimal promoter search space for potential TF binding sites is, for example, ±5 kbp from the TSS of human genes, and this promoter size is used to pre-compute the mechanistic TF regulatory network (i.e., the database of TF target gene interactions).

Starting with a human genome sequence (e.g., UCSC hg19) (data 360), the optimal promoter search space determined above can be implemented to extract promoter sequences (process 252) and determine a set (data 362) of promoter sequences within the genome. Those promoter sequences (data 362) can then be searched for sequences that match a TF DNA recognition motif (process 254), yielding a set (data 364) of instances of DNA recognition motifs. In an embodiment, this is accomplished using the "Find Individual Motif Occurrences" (FIMO) algorithm, operating with TFs collected from JASPAR, TRANSFAC, UniPROBE, AND SELEX databases. In an embodiment, redundancy across and within the JASPAR, TRANSFAC, UniPROBE, AND SELEX databases of DNA recognition motifs for the same TF can be removed by including a single representative motif for significantly similar motifs.

The instances of DNA recognition motifs (data 364) are then searched against digital genomic footprints (DGFs) to find DNA recognition motifs that intersect with DGFs by, for example, at least one base-pair (process 256). Genes are considered targets of a TF if at least one significant motif instance in the cis-regulatory regions overlapped with DGFs (data 366).

In a broad sense, the methods described above fit into a generalized pipeline comprising four phases. The first phase may be broadly described as dimensionality reduction, includes the processes 204 and 208. The second phase, broadly described as mechanistic regulatory network inference, includes the processes 210, 212, 214, 216, and 218. The third phase includes processes 220 and 222, and can be broadly conceptualized as causal regulatory network inference. Processes 224, 226, 228, 230, 232, 234, and 236 are included in the fourth phase, which may generally be described as annotating mechanism for causal regulatory inferences.

The third and fourth phases, which generally rely on the availability in the multi-omics data (data 300) of genomics data from which somatically mutated genes and pathways may be identified, need not be implemented in all embodiments. In embodiments, phases one and two may be implemented to arrive at the set (data 332) of disease relevant biclusters, which by itself may be a useful set of data for identifying therapeutic targets.

Figure 12:
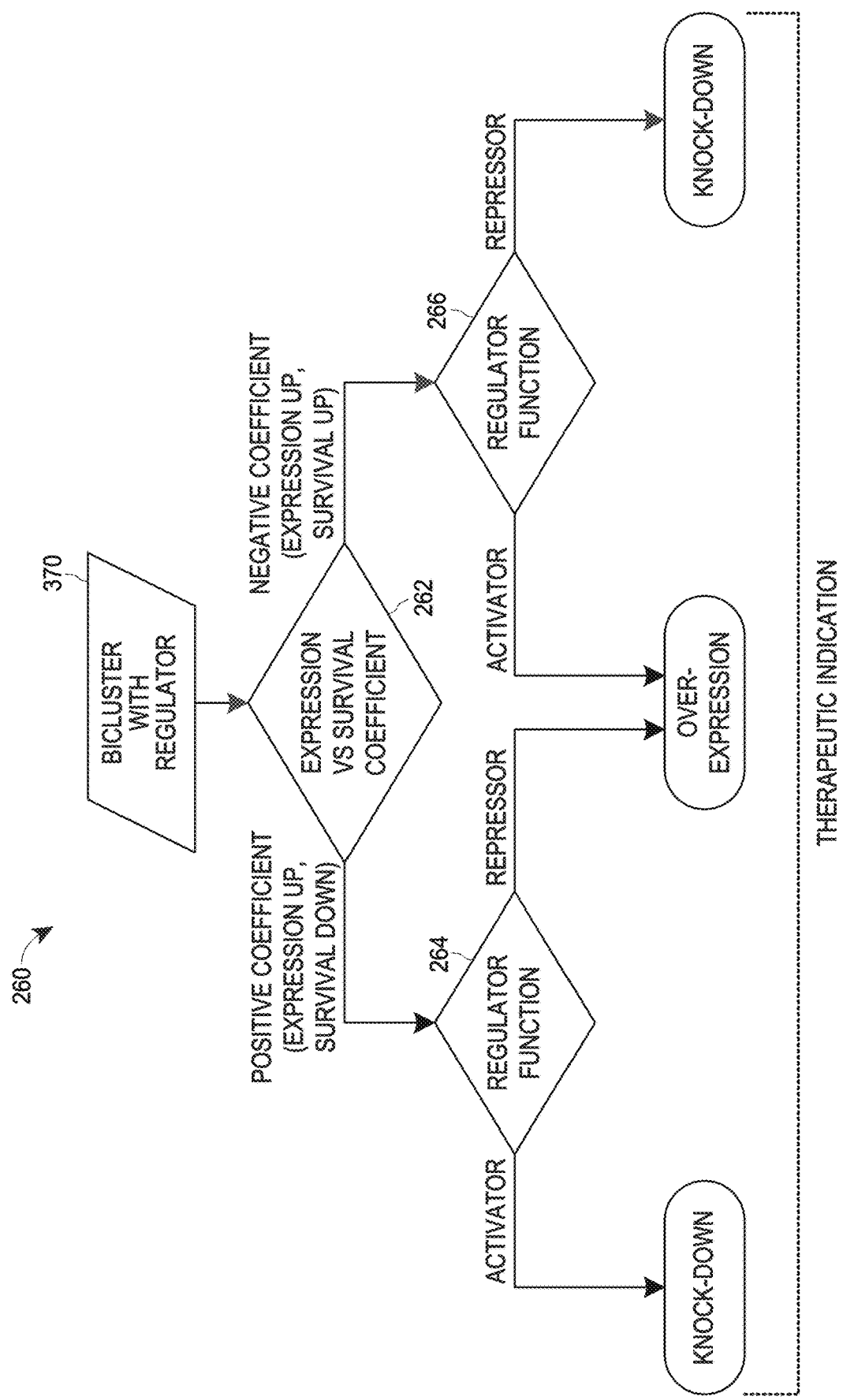
FIG. 12 is a decision tree for predicting the therapeutic indication of a given therapeutic target.

Having identified putative sets of TF and miRNA regulators, it is useful to determine which would be useful as therapeutic targets and which disease subtypes are most likely to respond to treatment and, in particular, for predicting the therapeutic indication (over-expression or knock-down). A decision tree for making such determinations is depicted in FIG. 12. For each bicluster with a regulator (data 370), an evaluation is made as to whether the regulator is positively or negatively associated with survival (process 262). A positive coefficient indicates that survival decreases with increased expression of the regulator, while a negative coefficient indicates that survival increases with increased expression of the regulator. For regulators having a positive coefficient, a determination is made as to whether the regulator generally functions as an activator or a repressor (process 264). Regulators with positive coefficients that generally act as activators are targets for therapeutic knock-down, while regulators with positive coefficients that generally act as repressors are targets for therapeutic over-expression. Similarly, for regulators having a negative coefficient, a determination is made as to whether the regulator generally functions as an activator or a repressor (process 266). Regulators with negative coefficients that generally act as activators are targets for therapeutic over-expression, while regulators with negative coefficients that generally act as repressors are targets for therapeutic knock-down.

Though it should be understood, it is worth noting that each of the processes described above executes on a processor (e.g., the processor 108) operating in a computer (e.g., the computer 100). That is, each process is embodied in a set of machine-readable instructions that are stored on a tangible, non-transitory computer-readable medium, which instructions may be retrieved from memory and executed by the processor using various input data and producing various output data.

Similarly, it should be understood that as data are manipulated and/or generated, the data may be stored locally in the non-volatile memory 112 and/or the volatile memory 114, and/or may be stored on the server 120 and/or the database 122 via the network 118. Data used as inputs but not generated by the processes described herein as part of the method 150 may be retrieved from their source(s) via the network 118 and stored locally in the memory 110 until overwritten, for example, by updated data retrieved via the network 118. For example, the multi-omics data (data 300) may be maintained by an external entity (e.g., The Cancer Genome Atlas) and stored on servers (e.g., the server 120) maintained by the external entity. The multi-omics data (data 300) may be periodically updated as new data are received and added to the dataset. The revised dataset may be downloaded again to the computer 100 via the network 118, and the method 150 re-executed to get an updated set of mechanistic and/or causal TFs and/or miRNAs based on the new data. In a similar manner, the PITA database (data 310), the TargetScan database (data 312), the validation data (data 320), and other sets of data may be updated periodically and the results of the method 150 re-evaluated. Similarly, algorithms associated with the processes herein may be updated, in embodiments, by retrieving revised computer-executable instructions.

Still further, it should be recognized that the processes and methods described herein may be useful in the identification of potential therapeutic targets for specific diseases (e.g., for specific cancers such as GBM) and for specific instances of those diseases (i.e., for patient-specific therapies). As a result, the utility of the methods and processes is contingent on the production of data on therapeutically relevant time scales. To be blunt, the data produced by the instant processes and methods is particularly useful in the clinic if it can be procured in time to be applied to a particular disease before the disease progresses and/or the patient succumbs to the condition. The magnitude of the datasets involved—for example, the three billion base pairs in the human genome, and the thousands of base pairs in a promoter sequence, etc.—make any implementation of the method outside of a computer environment—even if it were possible—therapeutically irrelevant as it the time scale over which such analysis would occur would be measured in years or decades, and would never be complete because of updates to the datasets used as input to the methods.

The first algorithm discovers biclusters of co-regulated genes through dimensionality reduction of transcriptomic data with simultaneous integration of cis-regulatory information. The biclusters are then used as input into a causal modeling algorithm which integrates genomic and transcriptomic data into a directed graph of information flows from genotype to regulator (TF or miRNA) to downstream target gene expression. Important to describe the functionality of each of the algorithms so that if the algorithms are updated, the scope of the claims is not limited to just one embodiment of the algorithm (e.g., cMonkey2).

Example: Application of the Computer-Implemented Method for Identifying and Characterizing Treatment Targets for GBM This example illustrates application of the computer-implemented method to glioblastoma multiforme.

Experimental Procedures

Constructing a TF-Target Gene Interaction Network

Regulatory sequences for each gene were acquired from the UCSC human genome release hg19. Unique TF DNA recognition motifs were collected from a public DNA recognition motif repository (JASPAR; Mathelier et al., 2014), a private DNA recognition motif repository (TRANSFAC; Matys et al., 2006), protein binding microarray DNA recognition motif repository (UniPROBE; Newburger and Bulyk, 2009) and a recent study that used high-throughput SELEX sequencing to discover DNA recognition motifs for most human TFs (Jolma et al., 2013). Digital genomic footprints aggregated across all tissue and cell lines were acquired from ENCODE (Neph et al., 2012). A gene was considered a target of a TF if it had at least one significant motif instance in its cis-regulatory regions that overlapped with a DGF by at least one base-pair. The genomic locations bound by 71 TFs in 148 ChIP-seq experiments (Wang et al., 2012) were downloaded from the UCSC genome browser. Overlap p-values of each TF versus each ChIP-seq TF bound gene-set were used to compute the sensitivity and specificity for predicting the TF that was immunoprecipitated in ChIP-seq studies.

Acquisition of TCGA and Independent Validation Cohort Data for GBM

All TCGA data were acquired from the Broad Firehose. Validation cohort data were either downloaded from the NCBI Gene Expression Omnibus (GSE7696 and GSE16011) (Gravendeel et al., 2009; Murat et al., 2008) or EMBL-EBI ArrayExpress (E-MTAB-3073) (Madhavan et al., 2009).

SYstems Genetics Network AnaLysis (SYGNAL) Pipeline

The SYstems Genetics Network AnaLysis (SYGNAL) pipeline was composed of 4 steps that are described briefly. First, simultaneous dimensionality reduction and mechanistic regulatory inference to discover TF and miRNA mediated regulation of biclusters based on the enrichment of TF or miRNA binding sites is accomplished using the cMonkey$_2$ biclustering algorithm (Reiss et al., 2015). Second, post-processing of the mechanistic regulatory network provides additional information about regulators, enrichment with functional categories, association with hallmarks of cancer, and association with patient survival. Third, the causal regulatory network inference approaches were applied to discover TF and miRNA mediated regulation based on the fitting of casual graphical models to the expression data. Fourth, we overlap the mechanistic and causal inferences for TF and miRNA mediated regulation of biclusters.

Discovering Combinatorial Regulation

We tested for significant evidence of combinatorial regulation using bidirectional stepwise linear regression and computed the significance of the increase in variance explained using ANOVA F-test. Co-occurrence of TF and miRNA binding sites was computed using a hypergeometric overlap p-value.

Results

Inference of a Comprehensive, Mechanistic Human TF-Target Gene Interaction Database To infer mechanistic transcription factor (TF)-mediated regulation of co-expressed transcripts, we constructed a database of TF-to-target gene interactions. The TF-to-target gene interactions were identified by intersecting the locations of 2,331 unique DNA recognition motifs for 690 TFs across the human genome (Matys et al., 2006; Newburger and Bulyk, 2009; Jolma et al., 2013; Mathelier et al., 2014) and encyclopedia of DNA elements (ENCODE)-determined 8.4 million genomic sites with digital genomic footprints (DGFs) across 41 diverse cell and tissue types (Neph et al., 2012). A DGF is experimental evidence that a DNA-binding protein was bound to a genomic location and, when coincident with a motif instance, suggests an interaction of a specific TF with that genomic location (FIG. 1A). We identified 17,415,125 genomic locations within the optimal promoter region of human genes (±5 Kbp from the transcriptional start site (TSS)) that matched significantly to a TF DNA recognition motif (FIMO p-value $\leq 1\times 10^{-5}$; FIG. 1A). The 3,505,491 motif instances that overlapped by at least 1 bp with a DGF were used to construct a map of interactions between the 690 TFs and 18,153 genes (FIG. 1A).

Figure 1B:
Figure 1C:
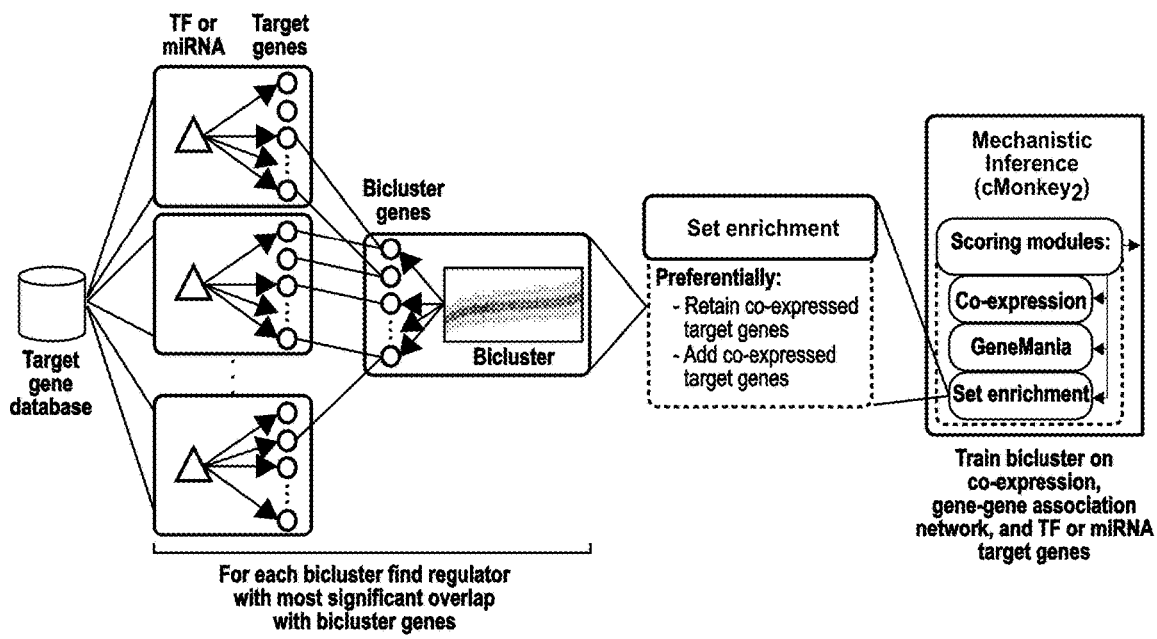

We then systematically evaluated the sensitivity and specificity of the inferred regulatory interactions by comparing the predicted TF-target gene interactions against a gold-standard physical map of protein-DNA interactions for 125 different TFs, constructed from 148 ChIP-seq experiments across 68 cell lines (FIG. 1B; Wang et al., 2012). Specifically, we tested the ability of the inferred regulatory interactions to predict the TF that was targeted for chromatin immunoprecipitation from ChIP-seq enriched genomic locations in each experiment. We chose this comparison because it mirrors how the interactions will be used to infer TF mediated regulation of co-expressed genes.

Figures 2A, 2B, 2C:
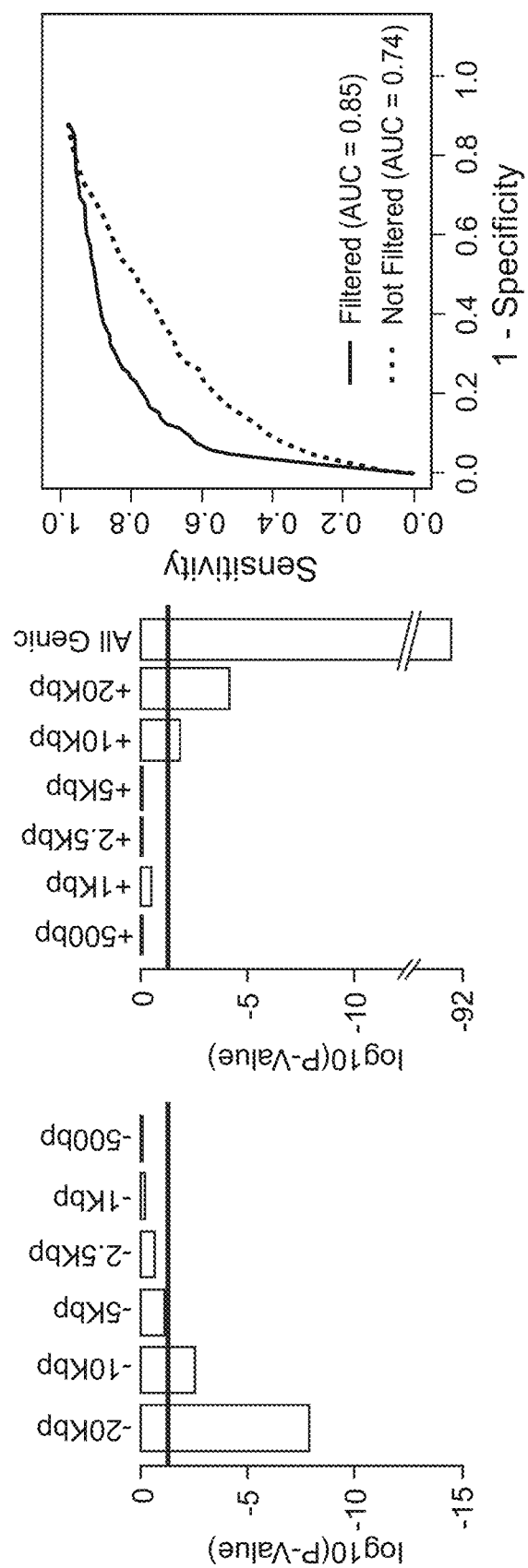
FIGS. 2A-2C. Determining the optimal promoter size to search for human TF binding sites.

First, we established that the optimal promoter region for predicting TF-DNA interactions using this approach was ±5 Kbp from the TSS, by systematically analyzing specificity and sensitivity of predictions across increasing promoter lengths compared to a 'core promoter' (i.e., ±500 bp of the TSS (Xie et al., 2005); see FIGS. 2A and 2B. An excessively large window lowers the specificity of detection, whereas a window that is too small could exclude regions that contain bona fide TF binding locations. We defined the optimum promoter region as the maximum sequence window surrounding the TSS that produces the same or greater sensitivity and specificity for predicting TF-target gene interactions as the 'core promoter' (i.e., ±500 bp of the TSS (Xie et al., 2005)). The maximum is chosen as the optimum because we know that human TF-target gene interactions can be separated by very long distances from the TSS both up- and down-stream from the TSS. To find this optimum region, we first fixed the downstream (3') promoter boundary at +500 bp and varied the upstream (5') promoter boundary (−1, −2.5, −5, −10 and −20 Kbp. Relative to the core promoter, a significant decrease in the sensitivity and specificity (p-value $\leq 0.05$) was observed when the upstream promoter boundary increased beyond −5 Kbp (p-value=$2.9\times 10^{-3}$). We then fixed the upstream promoter boundary at −5 Kbp and varied the downstream promoter boundary (+1, +2.5, +5, +10, +20 Kbp, and all genic sequences). We observed a significant decrease in sensitivity and specificity when the downstream promoter went beyond +5 Kbp (p-value=$1.5\times 10^{-2}$). Thus, we empirically defined the optimal promoter search space for potential TF binding sites to be ±5 Kbp from the TSS of human genes, and this was the promoter size used to pre-compute the mechanistic TF regulatory network (i.e., a database of TF-target gene interactions).

Next, we demonstrated that the sensitivity and specificity of predicting TF-target gene interactions improves significantly when motif instances are filtered based on DGF locations (unfiltered receiver operating characteristic area under the curve (ROC AUC)=0.74; filtered ROC AUC=0.85; comparison p-value=$6.9 \times 10^{-8}$; FIG. 2C). Notably, TF-target gene interactions accurately predicted the immunoprecipitated TF even in the 48 cell lines and tissues that were not represented within the ENCODE compendium of DGF profiles (DGF profiled ROC AUC=0.85, not profiled ROC AUC=0.82, comparison p-value=0.24). This result demonstrated that the collection of DGF profiles from 41 cell types within ENCODE had captured transcriptional regulation by most TFs across most cell types, including those that were not DGF profiled. Importantly, the specific cell-type and context for a given set of TF-target gene interactions can be recovered post hoc by analyzing the patterns of conditional co-expression of the target genes. We accomplished using the set-enrichment scoring module in the cMonkey$_2$ biclustering algorithm, which discovers the most enriched TF and trains each bicluster by preferentially retaining and adding co-expressed genes with the enriched TFs binding sites (FIG. 10). This approach with cMonkey$_2$ can also be used to discover miRNA mediated regulation using a miRNA-target gene database (PITA or TargetScan) as input for the set-enrichment scoring module.

Constructing a Transcriptional Regulatory Network for Glioblastoma Multiforme

We used patient data for glioblastoma multiforme (GBM) to develop the SYstems Genetics Network AnaLysis (SYGNAL) pipeline by integrating the methodology for constructing a mechanistic TF-target gene interaction database (described above) with previously developed multi-omics data mining methodologies, including (i) dimensionality reduction by discovering co-regulated gene modules (cMonkey$_2$; Reiss et al., 2015), (ii) inference of mechanistic miRNA regulatory network (framework for inference of regulation by miRNAs (FIRM) integrated into cMonkey$_2$; Plaisier et al., 2012), and (iii) mapping of causal effects from somatic mutations to regulators to their downstream target genes (network edge orienting (NEO); Aten et al., 2008). The SYGNAL pipeline constructs a TRN in three steps: 1) simultaneous dimensionality reduction and mechanistic inference of regulation by a TF of miRNA for a bicluster of genes and conditions (patients are considered conditions in the case of cancer); 2) filter biclusters by validating co-expression and ensuring disease relevance; and 3) causal inference that infers relationships linking somatic mutations to a TF or miRNA to the regulation of a bicluster. We applied the SYGNAL pipeline to multi-omics data from The Cancer Genome Atlas (TCGA) for GBM across 422 patients and 9 normal post-mortem controls to infer an integrated TF and miRNA regulatory network (FIG. 3A) (Brennan et al., 2013). The TCGA multi-omics data were refined at each omic level to enhance the signal-to-noise ratio.

The integrated analysis of all these multi-omics data with the SYGNAL pipeline and subsequent filtering discovered 500 biclusters (out of 1,830 biclusters) of genes that were significantly co-expressed across different subsets of patient tumors (in the TCGA and at least one independent GBM cohort) and were disease-relevant (significantly associated with patient survival or a hallmark of cancer; see, e.g., FIG. 3A). The SYGNAL pipeline also inferred causal influences for somatically mutated genes and pathways on the expression of TFs and miRNAs, which in turn were predicted to modulate the expression of co-regulated genes within one of the 500 biclusters (i.e., somatic mutation→TF or miRNA→bicluster; FIGS. 3B and 3C).

Using this approach, somatic mutations within 34 genes and 68 pathways were causally associated, through TFs and miRNAs, to the differential regulation of disease relevant genes (FIGS. 3A-3C). Notably, 9 of the 34 mutated genes are well known driver mutations in GBM (Gonzalez-Perez et al., 2013): AHNAK2, EGFR, IDH1, MLL3, NF1, PIK3CA, PIK3R1, PTEN and RB1. The SYGNAL pipeline derived network identified additional GBM driver mutations in 25 genes and 68 pathways that putatively act via modulating the activity of TFs and miRNAs, which in turn regulate the expression of 5,193 disease relevant genes associated with patient survival and/or hallmarks of cancer. Thus, the SYGNAL pipeline provides the means to synthesize genotype, gene expression and clinical information into a TRN (the gbmSYGNAL network) with both mechanistic and causal underpinnings to explain how specific mutations act through TFs and miRNAs to generate disease-relevant gene expression signatures observed within patient data.

TF Regulation in the gbmSYGNAL Network

The gbmSYGNAL network predicted at least one TF or miRNA as a regulator responsible for co-regulating genes within each of 237 biclusters. We hypothesized that we could extend predicted influences of a TF to its paralogs by assuming that the motifs within a TF family will not vary significantly (Wingender et al., 2013). Inclusion of TFs via expanded family memberships resulted in an ~1.5-fold increase in the number of TFs (51 to 74) that were incorporated into the network with both mechanism-based and causality-based evidence for regulation (p-value=$5.0 \times 10^{-5}$). These 74 TF's are as follows: NR2F1, MAFB, KLF2, ZNF217, ELF1, TBX10, ETV6, TFAP2C, IRF1, NFKB1, MYB, ETV7, KLF1, ZIC5, ISL1, ONECUT2, SOX9, ZFP42, IKZF1, ZNF281, E2F4, ESX1, ISX, TEAD2, PPARG, KLF4, GATA1, CREB5, SMAD9, CREB3L3, RARA, TCF4, TBX21, E2F8, TRIM28, TCF3, KLF12, TFCP2L1, IRF4, GATA2, CEBPD, CEBPE, KLF6, SOX4, GATA3, ZHX3, E2F7, SPDEF, TBX4, HAND1, RELB, ETS2, ASCL2, GABPA, ZEB1, JUNB, ELK3, RBPJ, NFIA, E2F3, CREB1, RARG, ELK1, KLF17, EGR3, ZNF148, MGA, ETV1, RXRB, RUNX3, ZSCAN4, LEF1, HOXD3, and SOX5.

To test gbmSYGNAL predictions, we extracted phenotype data for 1,445 TF knock outs (96% of known TFs) from our recent genome-wide CRISPR-Cas9 screen where we assayed consequences of each perturbation on the proliferation phenotype of two patient-derived glioma stem cell isolates (0131 and 0827) and two control neural stem cell lines (CB660 and U5) (Toledo et al., 2015). In total, knockout of 387 TFs significantly altered proliferation in glioma stem cell isolates (FDR ≤0.05) of which effects of knocking out 158 TFs were glioma-specific (i.e., significant effects in glioma stem cell isolates but not in neural stem cells). The gbmSYGNAL network derived directly from patient data was significantly enriched with 26 TFs that had altered proliferation phenotype in the CRISPR-Cas9 screen (p-value=$2.9 \times 10^{-2}$). Notably, thirteen of these TFs altered proliferation only in the glioma stem cell isolates (p-value=$2.5 \times 10^{-2}$; CEBPE, E2F4, HOXD3, KLF1, KLF17, KLF6, MYB, RXRB, ZFP42, ZIC5, ZNF148, ZNF217, ZSCAN4). The observation that 86% of the TF knock-outs had phenotypes in only one glioma stem cell isolate, underscores the known variability of such studies because of the extensive genetic heterogeneity across GBM tumors (Brennan et al., 2013). Specifically, knock-out of a particular TF will only show a phenotype in an appropriate genetic context, i.e., a patient-derived cell-line in which the specific TF-associated TRN is perturbed. We expect that future studies with patient derived glioma stem cell isolates with a different spectrum of mutations will provide appropriate context in which knock-outs of additional TFs in the gbm-SYGNAL network will alter proliferation. Thus, the CRISPR-Cas9 screen provided an unbiased phenotypic demonstration that the gbmSYGNAL network had deciphered disease-relevant transcriptional regulatory interactions directly from patient data.

In addition, three independent sources of evidence also supported biologically meaningful roles in GBM for a significant fraction of TFs in the gbmSYGNAL network:

(1) 8 of the 74 TFs were previously implicated in GBM by a regulatory network of 53 TFs that was inferred using a different dataset and a different set of algorithms (p-value=$4.4 \times 10^{-3}$) (Carro et al., 2010);

(2) according to the DisGeNET database (Piñero et al., 2015) of disease to gene associations, 16 of the 74 TFs have important functions in GBM (p-value=$5.2 \times 10^{-4}$); and (3) 33 of the 74 TFs (p-value=$2.3 \times 10^{-2}$) were differentially expressed in at least one GBM subtype relative to post-mortem controls (fold-change ≥2 and Benjamini-Hochberg (BH)-corrected p-value ≤0.05).

In summary, the gbmSYGNAL network implicated 74 TFs in the regulation of 3,170 GBM-relevant genes across 191 biclusters. Strikingly, 58 of the 74 TFs had not been previously associated with GBM. Each of these TFs is contemplated herein as a target for monotherapy and for combination therapy according to methods of the invention.

miRNA Regulation in the gbmSYGNAL Network

We incorporated miRNA regulation into the gbmSYGNAL network by integrating the Framework for inference of Regulation by miRNAs (FIRM; Plaisier et al., 2012) into cMonkey$_2$ using the set-enrichment scoring module. In the context of transcriptional regulation, miRNAs are known predominantly for their ability to repress transcript levels (Baek et al., 2008). Therefore, we limited miRNA regulatory predictions to models where the miRNA had a repressive effect. Altogether, 37 miRNAs were implicated in the regulation of genes within disease-relevant biclusters, either because their binding sites were enriched in the 3' UTRs of co-expressed genes within disease-relevant blusters (11 miRNAs), or because somatic mutations in the miRNAs were causally associated with disease-relevant expression changes (29 miRNAs) (Table S9). Four miRNAs (miR-19b, miR-23a, miR-128a and miR-128b) were implicated by both inference procedures (p-value=$2.8 \times 10^{-7}$).

| Bicluster | Mechanistic Correlated miRNAs | Causal miRNAs |
|---|---|---|
| pita_58 | NA | hsa-miR-142-5p hsa-miR-223 hsa-miR-27a hsa-miR-452 hsa-miR-513 |
| pita_76 | NA | hsa-miR-181d |
| pita_122 | NA | hsa-miR-181d |
| pita_126 | NA | hsa-miR-139 |
| pita_154 | NA | hsa-miR-142-5p hsa-miR-146b hsa-miR-146b hsa-miR-152 hsa-miR-223 hsa-miR-34a |
| pita_227 | NA | hsa-miR-181c |
| pita_251 | NA | hsa-miR-142-5p hsa-miR-223 hsa-miR-27a hsa-miR-27a |
| pita_254 | hsa-miR-200b | NA |

-continued

| Bicluster | Mechanistic Correlated miRNAs | Causal miRNAs |
|---|---|---|
| pita_262 | NA | hsa-miR-181d hsa-miR-181d |
| pita_282 | hsa-miR-128 hsa-miR-340 hsa-miR-495 | hsa-miR-133a |
| pita_314 | hsa-miR-128 hsa-miR-182 hsa-miR-9 | hsa-miR-181c |
| pita_358 | NA | hsa-miR-106b hsa-miR-17-5p |
| pita_369 | hsa-miR-551b | NA |
| pita_400 | NA | hsa-miR-142-5p hsa-miR-146b hsa-miR-223 |
| pita_411 | NA | hsa-miR-23a |
| pita_438 | NA | hsa-miR-128a hsa-miR-181a-3p hsa-miR-181d |
| pita_452 | hsa-miR-495 | NA |
| pita_469 | NA | hsa-miR-15b |
| pita_487 | NA | hsa-miR-21 |
| pita_516 | NA | hsa-miR-181d |
| pita_528 | NA | hsa-miR-23a hsa-miR-27a hsa-miR-27a hsa-miR-513 |
| pita_604 | NA | hsa-miR-142-5p |
| targetscan_6 | NA | hsa-miR-27a |
| targetscan_12 | hsa-miR-495 | NA |
| targetscan_27 | hsa-miR-200b | NA |
| targetscan_38 | NA | hsa-miR-181d hsa-miR-324-5p |
| targetscan_50 | NA | hsa-miR-181d |
| targetscan_89 | NA | hsa-miR-15b hsa-miR-25 |
| targetscan_135 | NA | hsa-miR-23a |
| targetscan_151 | NA | hsa-miR-181d |
| targetscan_161 | NA | hsa-miR-146b hsa-miR-34a |
| targetscan_286 | hsa-miR-23a | hsa-miR-27a |
| targetscan_288 | hsa-miR-340 | NA |
| targetscan_375 | NA | hsa-miR-23a |
| targetscan_377 | NA | hsa-miR-181c |
| targetscan_379 | hsa-miR-182 hsa-miR-183 hsa-miR-33b | NA |
| targetscan_416 | NA | hsa-miR-133a hsa-miR-133b hsa-miR-138 hsa-miR-139 |
| targetscan_424 | hsa-miR-33b | NA |
| targetscan_444 | NA | hsa-miR-128a hsa-miR-128b |
| targetscan_474 | NA | hsa-miR-23a |
| targetscan_487 | NA | hsa-miR-181d |
| targetscan_489 | NA | hsa-miR-223 |
| targetscan_533 | NA | hsa-miR-181d |
| targetscan_562 | NA | hsa-miR-181d |
| targetscan_584 | NA | hsa-miR-17-5p |
| targetscan_586 | NA | hsa-miR-142-5p hsa-miR-223 hsa-miR-27a hsa-miR-513 |
| targetscan_592 | NA | hsa-miR-181d |
| tfbs_db_6 | NA | hsa-miR-23a hsa-miR-27a |
| tfbs_db_43 | hsa-miR-340 hsa-miR-495 | NA |
| tfbs_db_51 | NA | hsa-miR-181d |
| tfbs_db_72 | hsa-miR-9 | NA |
| tfbs_db_76 | NA | hsa-miR-106a hsa-miR-106b hsa-miR-130b hsa-miR-17-5p |
| tfbs_db_90 | NA | hsa-miR-222 |
| tfbs_db_92 | NA | hsa-miR-142-5p hsa-miR-223 hsa-miR-27a hsa-miR-452 hsa-miR-513 |
| tfbs_db_125 | NA | hsa-miR-181d |
| tfbs_db_128 | hsa-miR-19b | hsa-miR-181c |
| tfbs_db_170 | NA | hsa-miR-142-5p hsa-miR-223 hsa-miR-23a hsa-miR-27a |
| tfbs_db_195 | NA | hsa-miR-142-5p |
| tfbs_db_239 | NA | hsa-miR-27a |
| tfbs_db_294 | NA | hsa-miR-23a |
| tfbs_db_426 | NA | hsa-miR-34a |
| tfbs_db_428 | hsa-miR-551b | hsa-miR-181d |
| tfbs_db_443 | NA | hsa-miR-152 |
| tfbs_db_468 | NA | hsa-miR-15b hsa-miR-25 |
| tfbs_db_525 | NA | hsa-miR-19a hsa-miR-19b |
| tfbs_db_530 | NA | hsa-miR-452 hsa-miR-513 |
| tfbs_db_537 | hsa-miR-495 | hsa-miR-133a |
| tfbs_db_541 | NA | hsa-miR-128a |

-continued

| Bicluster | Mechanistic Correlated miRNAs | Causal miRNAs |
|---|---|---|
| tfbs__db__586 | NA | hsa-miR-106b |
| tfbs__db__587 | hsa-miR-495 | NA |
| tfbs__db__591 | NA | hsa-miR-23a |
| Total | 11 | 29 |

Several independent lines of evidence supported the biological and disease significance of the miRNAs in the gbmSYGNAL network: first, 28 miRNAs were implicated in GBM in manually curated databases of miRNAs dysregulated and causally associated with human diseases (p-value ≤4.3×10$^{-3}$; miR2Disease (Jiang et al., 2009), and human miRNA disease database (HMDD) (Lu et al., 2008)); second, perturbations of 7 miRNAs have been shown to alter cancer phenotypes in GBM (miR-17, mir-15b, miR-21, miR-34a, miR-128, miR-146 and miR-222); and third, 25 miRNAs were also differentially expressed in at least one GBM subtype relative to post-mortem controls (p-value=1.1×10$^{-2}$; differential expression fold-change ≥2 and BH-corrected p-value ≤0.05). That 28 of the 37 miRNAs have been implicated as dysregulated or causally associated with GBM demonstrates the ability of the SYGNAL pipeline to recapitulate known regulatory interactions. The remaining/additional 9 miRNAs demonstrate the ability of the SYGNAL pipeline to discover new biology (miR-33b, miR-152, miR-181a-3p, miR-223, miR-324, miR-340, miR-495, miR-513 and miR-551b).

We selected the newly GBM associated miR-223 and miR-1292, whose expression was not profiled in the TOGA studies (and therefore was not included in the gbmSYGNAL network), to be screened for effects on proliferation or apoptosis in a primary astrocyte cell line (HA) and two GBM-derived cell lines (T98G and U251, available from ATCC and Sigma-Aldrich). We evaluated the potential roles of each miRNA in regulating proliferation and apoptosis by introducing miRNA mimics to simulate overexpression and miRNA inhibitors for knock-down. Over-expression of miR-223 led to significantly lowered proliferation and increased apoptosis in normal human astrocytes (fold-change ≥2 and B-H p-value ≤0.05). However, miR-223 over-expression marginally increased apoptosis and had little effect on proliferation in the two GBM cell lines. Thus, miR-223 does not appear to be an important factor for proliferation or apoptosis in the GBM cell lines we tested, although it may be important in other GBM cell lines or for other cancer phenotypes (e.g. angiogenesis or invasion).

On the other hand, knock-down of miR-1292 significantly reduced proliferation in normal human astrocytes and the U251 glioma cell line (fold-change ≥2 and B-H p-value ≤0.05). The miR-1292 was expressed at appreciable levels across all three cells lines (miRNA-seq counts 48 per sample in primary astrocytes and both GBM cell lines). Expression data for this miRNA across patient tumors was unavailable. Thus, predicted influence of miR-1292 was based entirely on the discovery of its binding site in the 3' UTRs of genes within disease-relevant biclusters, and brings the number of novel GBM associated miRNAs to 10. Taken together, the gbmSYGNAL network recapitulated much of what was known about miRNA regulation in GBM and discovered 10 new miRNA regulators, and the effects of miR-1292 were experimentally validated. Each of these 10 miRNAs are contemplated as targets for both monotherapy and combination therapy (agents directed at a second target) according to methods of the invention.

Combinatorial Regulatory Interactions

Nearly 40% of all biclusters in the gbmSYGNAL network (93 out of 242 biclusters) were predicted to be under combinatorial control of two or more regulators. Using GBM patient tumor expression data and bidirectional stepwise linear regression we constructed an additive combinatorial regulatory model that best explains the expression for each of the 93 bicluster eigengenes (the first principal component of the co-regulated genes). There was significant evidence that 87 of the 93 biclusters were putatively governed by an additive combinatorial regulatory scheme including two or more regulators (BH-corrected ANOVA p-value 0.05) as summarized in the following table:

| Bicluster | Combinatorial Regulators | Maximum Single Adjusted $R^2$ | Adjusted $R^2$ | Delta Adjusted $R^2$ | ANOVA B-H Corrected P-Value |
|---|---|---|---|---|---|
| targetscan__541 | IRF1 + PPARG + ELF1 | 0.278010203 | 0.506351797 | 0.228341595 | 2.44E−29 |
| targetscan__391 | TBX10 + ETV7 + ELF1 + ETV6 | 0.426572714 | 0.608980147 | 0.182407432 | 9.52E−29 |
| pita__145 | MYB + ZFP42 + SOX9 + ISL1 + ONECUT2 | 0.430041144 | 0.613363141 | 0.183321997 | 1.88E−28 |
| targetscan__413 | ZEB1 + KLF12 | 0.43923068 | 0.606161804 | 0.166931124 | 3.29E−28 |
| tfbs__db__266 | TFAP2C + ZIC5 + TBX10 + CREB3L3 | 0.232920002 | 0.470056118 | 0.237136115 | 9.76E−28 |
| tfbs__db__203 | SMAD9 + E2F3 + KLF1 + KLF17 | 0.273996938 | 0.495332191 | 0.221335253 | 2.94E−27 |
| pita__462 | TRIM28 + E2F8 + ZNF281 | 0.326622898 | 0.521254993 | 0.194632094 | 2.84E−26 |
| pita__58 | hsa-miR-27a + ZNF217 + hsa-miR-513 + hsa-miR-142-5p + hsa-miR-452 | 0.412523001 | 0.575913196 | 0.163390195 | 1.23E−23 |
| targetscan__602 | IRF4 + ZIC5 + TFAP2C | 0.259997127 | 0.450209393 | 0.190212266 | 8.54E−23 |
| tfbs__db__95 | ZIC5 + TBX10 + RARA | 0.210283495 | 0.408422672 | 0.198139177 | 3.79E−22 |
| tfbs__db__239 | hsa-miR-27a + EGR3 | 0.309964086 | 0.474689724 | 0.164725638 | 8.60E−22 |
| pita__229 | PPARG + ETV7 | 0.318996442 | 0.474279358 | 0.155282916 | 1.12E−20 |
| pita__438 | hsa-miR-128a + hsa-miR-181a-3p + hsa-miR-181d | 0.288911145 | 0.457142527 | 0.168231382 | 1.16E−20 |
| tfbs__db__456 | ELF1 + IRF1 | 0.280313646 | 0.430678603 | 0.150364957 | 9.91E−19 |
| pita__262 | NFKB1 + hsa-miR-181d | 0.317968204 | 0.459449289 | 0.141481085 | 1.39E−18 |
| pita__122 | NFKB1 + hsa-miR-181d | 0.293868638 | 0.437051118 | 0.14318248 | 4.05E−18 |
| tfbs__db__331 | ELF1 + PPARG | 0.261607394 | 0.409993883 | 0.148386489 | 6.08E−18 |

-continued

| Bicluster | Combinatorial Regulators | Maximum Single Adjusted $R^2$ | Adjusted $R^2$ | Delta Adjusted $R^2$ | ANOVA B-H Corrected P-Value |
|---|---|---|---|---|---|
| pita_154 | hsa-miR-34a + hsa-miR-152 + hsa-miR-223 | 0.286481736 | 0.428543122 | 0.142061386 | 6.81E−17 |
| tfbs_db_43 | IRF1 + hsa-miR-340 + ZNF281 + hsa-miR-495 | 0.455259415 | 0.567213321 | 0.111953906 | 7.50E−17 |
| pita_378 | TCF4 + IRF1 | 0.313377124 | 0.441908601 | 0.128531477 | 1.38E−16 |
| pita_141 | ZIC5 + KLF1 + TFAP2C | 0.181455305 | 0.340840118 | 0.159384813 | 1.77E−16 |
| tfbs_db_92 | hsa-miR-27a + hsa-miR-142-5p + hsa-miR-513 + hsa-miR-223 | 0.2551207 | 0.404200035 | 0.149079335 | 2.42E−16 |
| pita_126 | hsa-miR-139 + NFKB1 | 0.401116074 | 0.509977156 | 0.108861083 | 4.51E−16 |
| tfbs_db_76 | hsa-miR-130b + TCF3 + hsa-miR-17-5p + hsa-miR-106a | 0.42496289 | 0.538016524 | 0.113053635 | 5.21E−16 |
| targetscan_586 | hsa-miR-27a + hsa-miR-223 + hsa-miR-513 + hsa-miR-142-5p | 0.270896176 | 0.410959589 | 0.140063413 | 1.40E−15 |
| targetscan_592 | ETV7 + hsa-miR-181d | 0.268489391 | 0.396979662 | 0.128490271 | 1.71E−15 |
| tfbs_db_435 | TFCP2L1 + SMAD9 + RXRB | 0.15580408 | 0.310380649 | 0.154576569 | 2.20E−15 |
| pita_71 | ETV6 + TFAP2C | 0.27444373 | 0.398565639 | 0.124121909 | 4.64E−15 |
| pita_282 | IRF1 + hsa-miR-340 + hsa-miR-128a + hsa-miR-495 | 0.469403359 | 0.566885859 | 0.0974825 | 8.44E−15 |
| targetscan_533 | IRF1 + hsa-miR-181d | 0.372036787 | 0.475943985 | 0.103907199 | 1.57E−14 |
| tfbs_db_525 | ZNF281 + hsa-miR-19a | 0.249102729 | 0.372618404 | 0.123515675 | 1.91E−14 |
| pita_605 | CEBPD + CEBPE + KLF6 | 0.626207244 | 0.688564843 | 0.062357599 | 7.45E−14 |
| pita_411 | hsa-miR-23a + TBX21 | 0.287343598 | 0.396335296 | 0.108991698 | 2.36E−13 |
| targetscan_576 | IRF1 + ELF1 | 0.242769933 | 0.356791817 | 0.114021884 | 3.89E−13 |
| targetscan_140 | ZHX3 + GATA3 + GATA1 | 0.288769111 | 0.401716758 | 0.112947647 | 4.06E−13 |
| targetscan_502 | RBPJ + ZIC5 | 0.312935032 | 0.415446543 | 0.102511511 | 5.07E−13 |
| tfbs_db_263 | CREB1 + E2F4 | 0.289754357 | 0.385965456 | 0.096211099 | 9.78E−12 |
| tfbs_db_541 | hsa-miR-128a + SOX5 | 0.301748881 | 0.391635081 | 0.0898862 | 4.06E−11 |
| tfbs_db_281 | KLF12 + ZNF148 + PPARG | 0.4126 | 0.492377497 | 0.079777497 | 5.17E−11 |
| targetscan_313 | ZNF281 + TEAD2 | 0.243333471 | 0.338043661 | 0.09471019 | 8.36E−11 |
| tfbs_db_186 | IRF1 + ELF1 | 0.202274724 | 0.301308054 | 0.09903333 | 1.02E−10 |
| targetscan_484 | ELK3 + ETV6 | 0.284613108 | 0.369558917 | 0.084945808 | 3.14E−10 |
| tfbs_db_326 | IKZF1 + IRF1 | 0.392475829 | 0.461504901 | 0.069029072 | 9.07E−10 |
| targetscan_530 | NFKB1 + ETV6 | 0.380536334 | 0.450796252 | 0.070259917 | 9.27E−10 |
| targetscan_173 | IRF1 + NFKB1 | 0.452498414 | 0.513509673 | 0.061011259 | 1.38E−09 |
| tfbs_db_426 | TCF4 + hsa-miR-34a + RARG | 0.43113881 | 0.49800477 | 0.066865959 | 2.04E−09 |
| pita_317 | SMAD9 + CREB5 + KLF1 | 0.28659769 | 0.370261053 | 0.083663364 | 2.11E−09 |
| pita_314 | hsa-miR-9 + hsa-miR-128a + hsa-miR-182 + hsa-miR-181c | 0.201523291 | 0.299362357 | 0.097839066 | 2.51E−09 |
| pita_150 | IKZF1 + IRF1 | 0.430165137 | 0.491137934 | 0.060972796 | 3.19E−09 |
| targetscan_231 | IRF4 + HAND1 + ETV7 | 0.451712647 | 0.514073936 | 0.062361288 | 4.07E−09 |
| targetscan_288 | IRF1 + hsa-miR-340 | 0.269350187 | 0.346174616 | 0.07682443 | 4.47E−09 |
| tfbs_db_128 | hsa-miR-19b + hsa-miR-181c | 0.173022499 | 0.259757697 | 0.086735198 | 4.61E−09 |
| pita_528 | hsa-miR-27a + hsa-miR-513 | 0.370290576 | 0.435829724 | 0.065539149 | 5.31E−09 |
| tfbs_db_581 | TCF4 + ELF1 | 0.1234944 | 0.212513912 | 0.089019513 | 8.74E−09 |
| pita_135 | TBX10 + ETV7 | 0.328244436 | 0.394510437 | 0.066266001 | 1.56E−08 |
| tfbs_db_294 | hsa-miR-23a + E2F4 | 0.162523685 | 0.244065499 | 0.081541814 | 1.98E−08 |
| pita_591 | ETV7 + ZIC5 | 0.349189814 | 0.411171939 | 0.061982125 | 2.99E−08 |
| pita_400 | hsa-miR-142-5p + hsa-miR-146b + hsa-miR-223 | 0.270641445 | 0.345602302 | 0.074960857 | 3.09E−08 |
| pita_469 | TCF3 + hsa-miR-15b | 0.225158522 | 0.297638119 | 0.072479597 | 3.99E−08 |
| targetscan_286 | hsa-miR-27a + TEAD2 + hsa-miR-23a | 0.376210144 | 0.439124937 | 0.062914792 | 4.28E−08 |
| targetscan_60 | ETV7 + ELF1 | 0.300926226 | 0.362989631 | 0.062063406 | 1.00E−07 |
| tfbs_db_181 | ETV7 + ELF1 | 0.306836393 | 0.366472183 | 0.05963579 | 1.70E−07 |
| targetscan_38 | hsa-miR-324-5p + hsa-miR-181d | 0.227025512 | 0.292826581 | 0.065801069 | 1.98E−07 |
| tfbs_db_480 | ZSCAN4 + TFCP2L1 | 0.100172318 | 0.167970034 | 0.067797716 | 1.41E−06 |
| tfbs_db_586 | PPARG + hsa-miR-106b | 0.118603027 | 0.181847913 | 0.063244887 | 2.83E−06 |
| targetscan_9 | IRF1 + ETV6 | 0.290984498 | 0.34159819 | 0.050613691 | 2.93E−06 |
| targetscan_456 | ELF1 + ETV6 | 0.206706225 | 0.263097518 | 0.056391293 | 2.99E−06 |
| targetscan_135 | hsa-miR-23a + TBX10 | 0.284819664 | 0.33188843 | 0.047068767 | 8.03E−06 |
| pita_358 | hsa-miR-17-5p + hsa-miR-106b | 0.373856305 | 0.41497106 | 0.041114755 | 8.03E−06 |
| targetscan_161 | hsa-miR-34a + hsa-miR-146b | 0.299760158 | 0.345983763 | 0.046223605 | 8.03E−06 |
| targetscan_89 | hsa-miR-25 + hsa-miR-15b | 0.214370932 | 0.26482722 | 0.050456288 | 1.00E−05 |
| tfbs_db_468 | hsa-miR-25 + hsa-miR-15b | 0.191010393 | 0.239376596 | 0.048366203 | 2.34E−05 |
| pita_251 | hsa-miR-27a + hsa-miR-223 | 0.428359387 | 0.460840429 | 0.032481041 | 4.03E−05 |
| targetscan_429 | SOX9 + TBX10 | 0.211168752 | 0.253342291 | 0.042173539 | 7.49E−05 |
| tfbs_db_170 | hsa-miR-27a + hsa-miR-223 + hsa-miR-23a + hsa-miR-142-5p | 0.426072774 | 0.462381773 | 0.036308999 | 0.000103093 |
| tfbs_db_182 | ZHX3 + TFAP2C | 0.285016904 | 0.320429762 | 0.035412858 | 0.000143118 |
| tfbs_db_529 | ETV7 + HOXD3 | 0.249729313 | 0.286962059 | 0.037232746 | 0.000143118 |
| pita_280 | NR2F1 + GATA1 | 0.155258805 | 0.193669953 | 0.038411148 | 0.000286164 |
| targetscan_416 | hsa-miR-139 + hsa-miR-138 | 0.450416119 | 0.473800223 | 0.023384104 | 0.000475445 |

-continued

| Bicluster | Combinatorial Regulators | Maximum Single Adjusted $R^2$ | Adjusted $R^2$ | Delta Adjusted $R^2$ | ANOVA B-H Corrected P-Value |
|---|---|---|---|---|---|
| tfbs_db_537 | IRF1 + hsa-miR-495 + hsa-miR-133a | 0.441743136 | 0.466555745 | 0.024812608 | 0.001011151 |
| tfbs_db_587 | IRF1 + hsa-miR-495 | 0.506045184 | 0.524364658 | 0.018319474 | 0.001188693 |
| pita_452 | IRF1 + hsa-miR-495 | 0.482856225 | 0.500735596 | 0.017879371 | 0.001774871 |
| pita_320 | TFAP2C + E2F4 | 0.096595039 | 0.124383741 | 0.027788702 | 0.003127734 |
| targetscan_12 | IRF1 + hsa-miR-495 | 0.466025135 | 0.482674195 | 0.01664906 | 0.003127734 |
| targetscan_369 | CREB3L3 + GATA1 | 0.28159801 | 0.300240359 | 0.018642349 | 0.006758954 |
| tfbs_db_428 | hsa-miR-181d + hsa-miR-551b | 0.183365065 | 0.197416624 | 0.014051559 | 0.033698449 |
| pita_254 | KLF4 + hsa-miR-200b | 0.15537609 | 0.168705794 | 0.013329703 | 0.036228049 |

Each of these combinations are contemplated as targets for combination therapy (agents directed at two or more targets) according to methods of the invention.

Of the 87 additive combinatorial models of bicluster regulation, 58 included two regulators, 17 included three regulators, 10 included four regulators, and 2 included five regulators. In the combinatorial models there were 54 TFs and 31 miRNAs that integrated into 45 TF-TF, 17 miRNA-miRNA, and 25 TF-miRNA combinatorial regulatory interactions (FIG. 4A). We conducted the same analyses above with correction for bicluster redundancy and obtained similar results, indicating that bicluster redundancy has not biased these analyses. Even though biclusters might be redundant the subtle distinctions may reflect real differences between patients and processes, and future work can address this redundancy through ensemble based methods that assign confidence metrics to gene co-occurrence across biclusters (Brooks et al., 2014).

The 54 TFs in the combinatorial models include 23 of the 26 TFs in the gbmSYGNAL network with significantly altered proliferation in glioma stem cell isolate CRISPR-Cas9 knock-outs (p-value=$4.6 \times 10^{-3}$; FIG. 4A), and all 13 TFs with glioma specific proliferation effects (p-value $<2.2 \times 10^{-16}$). These data demonstrate that a majority of the TFs involved in combinatorial regulatory interactions are functional and disease-relevant. Additionally, 44% of TF-TF, miRNA-miRNA and TF-miRNA pairs within combinatorial models had significant binding site co-occurrence within the corresponding regulatory regions (promoter or 3' UTR) of bicluster genes (BH-corrected p-value ≤0.05). This observation demonstrates that the predicted combinatorial regulators are directly interacting with regulatory regions of the same genes and thereby mediating their co-expression. The ability of the SYGNAL pipeline to uncover combinatorial regulatory interactions provides deeper understanding of GBM etiology and enables strategies for combinatorial therapeutic interventions.

Effects of Double Knock-Down of Combinatorial Regulators on Proliferation and Apoptosis Published reports have demonstrated that combinations of master regulators can be used to predict synergistic compound pairs (Bansal et al., 2014). Therefore, we explored whether combinatorial regulation in the gbmSYGNAL network can facilitate discovery of combinatorial interventions that lead to additive or synergistic outcomes. From the list of 87 predicted combinatorial regulatory models, we selected four pairwise TF combinations (CEBPD-CEBPE, ELF1-PPARG, ETV6-NFKB1, and IRF1-IKZF1) that maximized coverage of four different criteria: (1) their location in the combinatorial network; (2) the increase in variance explained by the combinatorial model; (3) whether there are known interactions between the TFs; and (4) whether there is a significant co-occurrence of binding sites between the TFs.

| $TF_1$ | $TF_2$ | Combinatorial Network | Combinatorial Model | Known Interaction | Significant Co-occurrence of Binding Sites |
|---|---|---|---|---|---|
| CEBPD | CEBPE | Isolated in the combinatorial network along with KLF6 | In conjunction with KLF6 they have a moderate increase in variance explained for pita_605 | Known to dimerize | Yes |
| ELF1 | PPARG | Both moderately connected in the network | In two models with very dramatic increases in variance explained (minimum of ~15% increase R2) | None | Yes |
| ETV6 | NFKB1 | Both moderately connected in the network, but lacking significant overlap of genes with binding sites | Only two regulators in model with for bicluster targetscan_530 and a moderate increase in variance explained | None | No |
| IRF1 | IKZF1 | IRF1 most highly connected and IKZF1 is a stub | Only two regulators in model with for bicluster tfbs_db_326 and a moderate increase in variance explained | None | Yes |

We assayed the effect of double knock-downs of the four pair-wise combinations in all three cell lines on proliferation and apoptosis, with results summarized in the following tables:

Combinatorial TF-TF siRNA Knock-Down Effects on Proliferation.

| siRNA Knock-Down | HA Fold-Change | HA p-Value | T98G Fold-Change | T98G p-Value | U251 Fold-Change | U251 p-Value |
| --- | --- | --- | --- | --- | --- | --- |
| CEBPD | 1.69 | $6.0 \times 10^{-4}$ | −1.14 | $7.1 \times 10^{-3}$ | 1.17 | $3.5 \times 10^{-2}$ |
| CEBPE | 1.43 | $5.9 \times 10^{-3}$ | −1.06 | $3.5 \times 10^{-1}$ | 1.17 | $3.8 \times 10^{-2}$ |
| CEBPD + CEBPE | 1.48 | $2.7 \times 10^{-1}$ | −1.25 | $7.6 \times 10^{-2}$ | 1.09 | $2.4 \times 10^{-2}$ |
| ELF1 | 1.62 | $1.1 \times 10^{-3}$ | 1.08 | $5.0 \times 10^{-2}$ | 1.36 | $1.9 \times 10^{-3}$ |
| PPARG | 1.32 | $8.4 \times 10^{-2}$ | −1.69 | $1.1 \times 10^{-2}$ | −1.20 | $1.9 \times 10^{-2}$ |
| ELF1 + PPARG | 1.11 | $8.3 \times 10^{-1}$ | 1.04 | $8.1 \times 10^{-1}$ | −1.01 | $5.7 \times 10^{-1}$ |
| ETV6 | 1.40 | $7.8 \times 10^{-2}$ | 1.12 | $5.7 \times 10^{-2}$ | −1.69 | $2.4 \times 10^{-3}$ |
| NFKB1 | 1.07 | $7.1 \times 10^{-1}$ | −1 | $5.2 \times 10^{-1}$ | −1.04 | $3.6 \times 10^{-1}$ |
| ETV6 + NFKB1 | 1.23 | $5.9 \times 10^{-1}$ | 1.23 | $1.9 \times 10^{-1}$ | −2.22 | $2.9 \times 10^{-7}$ |
| IKZF1 | 1.82 | $7.0 \times 10^{-4}$ | 1.16 | $4.5 \times 10^{-2}$ | 1.14 | $7.7 \times 10^{-2}$ |
| IRF1 | 2.46 | $1.0 \times 10^{-3}$ | 1.52 | $1.7 \times 10^{-3}$ | 1.31 | $2.5 \times 10^{-3}$ |
| IKZF1 + IRF1 | 1.39 | $5.1 \times 10^{-1}$ | 1.08 | $2.2 \times 10^{-1}$ | 1.03 | $6.3 \times 10^{-1}$ |

Significant after Benjamini-Hochberg mutliple hypothesis correction (36 tests).

Combinatorial TF-TF siRNA Knock-Down Effects on Apoptosis.

| siRNA Knock-Down | HA Fold-Change | HA p-Value | T98G Fold-Change | T98G p-Value | U251 Fold-Change | U251 p-Value |
| --- | --- | --- | --- | --- | --- | --- |
| CEBPD | −1.39 | $1.3 \times 10^{-2}$ | −1.25 | $2.1 \times 10^{-1}$ | −1.19 | $2.4 \times 10^{-2}$ |
| CEBPE | −1.18 | $1.3 \times 10^{-1}$ | −1.20 | $2.6 \times 10^{-1}$ | −1.02 | $8.1 \times 10^{-1}$ |
| CEBPD + CEBPE | −1.18 | $1.1 \times 10^{-1}$ | −1.32 | $9.8 \times 10^{-2}$ | −1.25 | $3.4 \times 10^{-3}$ |
| ELF1 | −1.27 | $4.5 \times 10^{-2}$ | −1.41 | $6.6 \times 10^{-2}$ | −1.11 | $1.6 \times 10^{-1}$ |
| PPARG | −1.47 | $7.2 \times 10^{-3}$ | −1.67 | $2.8 \times 10^{-2}$ | −1.41 | $3.2 \times 10^{-3}$ |
| ELF1 + PPARG | −1.33 | $1.3 \times 10^{-2}$ | −1.54 | $2.5 \times 10^{-2}$ | −1.32 | $6.9 \times 10^{-4}$ |
| ETV6 | −1.10 | $3.3 \times 10^{-1}$ | −1.05 | $8.3 \times 10^{-1}$ | −1.09 | $2.9 \times 10^{-1}$ |
| NFKB1 | −1.43 | $9.4 \times 10^{-3}$ | −1.33 | $1.8 \times 10^{-1}$ | −1.19 | $4.3 \times 10^{-2}$ |
| ETV6 + NFKB1 | −1.19 | $8.0 \times 10^{-2}$ | −1.23 | $7.5 \times 10^{-2}$ | −1.22 | $2.5 \times 10^{-3}$ |
| IKZF1 | −1.09 | $2.7 \times 10^{-1}$ | 1.15 | $1.9 \times 10^{-1}$ | −1.04 | $6.1 \times 10^{-1}$ |
| IRF1 | −1.25 | $3.4 \times 10^{-2}$ | 1.05 | $4.8 \times 10^{-1}$ | 1 | $6.2 \times 10^{-1}$ |
| IKZF1 + IRF1 | −1.11 | $4.7 \times 10^{-1}$ | 1.1 | $8.7 \times 10^{-1}$ | 1.03 | $8.5 \times 10^{-1}$ |

Significant after Benjamini-Hochberg mutliple hypothesis correction (36 tests).

We used the Bliss independence model (Bliss, 1939) to assess the extent to which combinatorial effects deviated from an additive model: 1) additive, combined effect is indistinguishable from the expected additive effect; 2) antagonistic, combined effect is less than the expected additive effect; or 3) synergistic, combined effect is greater than the expected additive effect. Double knock-down of ETV6 and NFKB1 synergistically reduced proliferation in the U251 GBM cell line (observed fold-change=−2.22±0.02; expected additive fold-change=−1.82; BH-corrected T-test p-value=$8.2 \times 10^{-3}$; FIG. 4B). Double knock-down of CEBPD and CEPBE resulted in an additive decrease in apoptosis in the U251 GBM cell line (observed fold-change=−1.25±0.12; expected additive fold-change=−1.23; BH-corrected T-test p-value=0.67). Double knock-downs of IKZF1-IRF1 and ELF1-PPARG had antagonistic effects on proliferation and apoptosis, respectively (FIG. 4B). These results indicate that the topology of combinatorial regulatory interactions in the gbmSYGNAL network can accelerate the identification of synergistically acting drug combinations.

An Emergent Transcriptional Signature Underlies the Synergistic Effect of a Pairwise Combination To elucidate the mechanism(s) underlying the synergistic interaction between ETV6 and NFKB1, we analyzed the genome-wide transcriptional consequences of single and double knock-down of the two TFs in U251 cells. As expected, transcript levels of both TFs were reduced when knocked-down, individually or in combination (fold-change ≤−1.8 and p-value ≤0.05). Consistent with their predicted roles as activators, knock-down of each TF led to significant down-regulation for a large number of genes (ETV6: 287 genes; NFKB1: 1,306 genes; fold-change ≤−2 and BH-corrected p-value ≤0.1), and significantly fewer genes were up-regulated (ETV6: 5 genes; NFKB1: 7 genes; fold-change ≥2 and BH-corrected p-value ≤0.1). The down-regulated genes were significantly enriched with predicted targets of the perturbed TF (ETV6: 21 genes and p-value=0.042; NFKB1: 97 genes and p-value=$5.5 \times 10^{-3}$). In addition, a common set of 247 genes were down-regulated in both knock-downs, suggesting a significant overlap in the regulatory networks of the two TFs (p-value <$2.2 \times 10^{-16}$; FIG. 4C). However, there is not a significant amount of ETV6 and NFKB1 motif co-occurrence in the 247 genes (p-value=0.63), suggesting that their combinatorial influence may be more complicated than simply binding to the same promoters.

Relative to the single knock-downs, the double knock-down of ETV6 and NFKB1 resulted in the up-regulation of a significantly larger number of genes (438 genes; fold-change ≥2 and BH-corrected p-value ≤0.1; FIG. 3C) and down-regulation of only 22 genes (fold-change ≤−2 and BH-corrected p-value ≤0.1; FIG. 3C). A significant fraction of the up-regulated genes in the double knock-down were down-regulated in the single TF knock-downs (ETV6: 57 genes and p-value <$2.2 \times 10^{-16}$; NFKB1: 210 genes and p-value <$2.2 \times 10^{-16}$; FIG. 4C). Notably, 48 up-regulated genes in the double knock-down were among the 247 genes that were down-regulated by single knock-down of both TFs (p-value <$2.2 \times 10^{-16}$; FIGS. 4C and 4D). This reversal in direction of differential expression for 210 genes and the up-regulation of an additional 228 genes is unexpected given the consequences of single knock-downs for the TFs. The precise mechanism for this synergistic anti-proliferative interaction is not readily discernible from the transcriptome changes, and it is unlikely that we could have predicted the impact of the double knock-down from the single knock-downs. While effects like this are to be expected in a massively combinatorial non-linear network, we have shown that knowledge of the topology of regulatory interactions can facilitate the selection of synergistically acting TFs and miRNAs.

Approach to Discover Synergistic Combinations of Inhibitors and miRNA Mimics from the gbmSYGNAL Network It has been shown that the simultaneous knock-down of an oncogene mRNA and inhibition of its protein activity using a drug can lead to a synergistic effect (Choi et al., 2012). Therefore, we systematically screened for synergistic phenotypic effects of combining miRNA mimics and established inhibitor therapies that were predicted to target the same oncogene in the gbmSYGNAL network. Inhibitors targeting 49 oncogenes have been considered in treating GBM (Alexander et al., 2013; Ohka et al., 2012; Patil et al., 2013; Sathornsumetee et al., 2007; Wen et al., 2006). The gbmSYGNAL network included 18 of these 49 oncogenes, 5 of which were predicted to be regulated by at least one miRNA (6 miRNAs, 7 inhibitors, and 7 possible combinations; see Table below). We assayed the consequence of single treatments for the 6 miRNA mimics (miR-450a, miR-486-3p, miR-506, miR-511, miR-578 and miR-892b) and 7 inhibitors (erlotinib, gefitinib, imatinib, romidepsin, sorafenib, vatalanib and vorinostat) on proliferation and apoptosis across the HA, T98G and U251 cell lines. For these studies we specifically screened for significant (BH-corrected p-value ≤0.05) anti-proliferative (proliferation fold-change ≤0.8) and pro-apoptotic (apoptosis fold-change ≥1.25) effects as these are the desired therapeutic responses when treating cancers.

All inhibitors, as expected, and three miRNAs (miR-486-3p, miR-506 and miR-892b) had significant anti-proliferative effects in at least one cell line. Six inhibitors (with the exception of gefitinib) had significant pro-apoptotic effects in at least one cell line, whereas of the miRNA mimics only miR-892b had a significant pro-apoptotic effect in HA and T98G cells. Together, the single agent screens identified 6 inhibitor-miRNA combinations targeting 3 oncogenes (FLT1, HDAC5 and KDR) that could be tested for synergistic anti-proliferative effects; and two inhibitor-miRNA combinations targeting two oncogenes (FLT1 and KDR) that could be tested for synergistic pro-apoptotic effects.

Targeted Inhibitor and miRNA Mimic Combinations.

response curves for romidepsin and miR-486-3p in the U251 cell line (romidepsin $IC_{50}$=1.1 nM, miR-486-3p $IC_{50}$=4.6 nM; FIGS. 4D and E). Then we designed a 6×6 dose response matrix with a range of concentrations centered on the $IC_{50}$ of each therapeutic agent. Four different combinations from this dose response matrix generated synergistic effects (synergy score 2.3; cumulative log volume=3.19). Significant synergy was observed for romidepsin concentrations between 0.167 to 0.634 nM and miR-486-3p concentrations between 0.5 to 4.6 nM. Maximal synergy was observed with a combination of 0.634 nM romidepsin and 4.6 nM miR-486-3p mimic, which generated an effect size (fold-change=−3.1) that was equivalent to 1.75 fold higher concentration of single treatment with 1.1 nM romidepsin. The effect size of this combination was also very similar to the effects of 1.85 nM romidepsin that was previously observed to be anti-proliferative and pro-apoptotic in GBM cell lines (Sawa et al., 2004). This data demonstrates that the gbmSYGNAL network can facilitate discovery of combinations of inhibitors and novel miRNAs that act synergistically on cancer phenotypes of GBM cell lines. Applied in a high throughout framework, this approach could in turn aid in the prioritization of future studies on delivery and dosing that together will help to assess the therapeutic potential of selected combinations, such as ETV6-NFKB.

These combination therapies are specifically contemplated as aspects of the invention. Furthermore, in some variations, these combinations are contemplated at doses that achieve in vivo concentrations within 50%, or within 25%, or within 10%, or within the ranges described herein as having synergistic effects against cell lines. More particularly, doses and routes of administration are contemplated that achieve such concentrations locally, at the site of the tumor.

NF1 and PIK3CA Modulate IRF1 which Regulates Antigen Processing and Presentation and is Associated with Tumor Lymphocyte Infiltration Finally, we demonstrate how the gbmSYGNAL network knits together layers of biological and clinical data into a cohesive platform for making deeper and more meaningful insights. For example, the gbmSYGNAL network links somatic driver mutations in either NF1 or PIK3CA to the

| Oncogene | Gene(s) | Oncogene Inhibitor | miRNA(s) | Signficant Effect on Proliferation | Significant Effect on Apoptosis |
|---|---|---|---|---|---|
| EGFR | EGFR | Erlotinib | miR-450a | | |
| | | Gefitinib | | | |
| PDGFR | PDGFRB | Imatinib | miR-511 | | |
| VEGFR | FLT1 (VEGFR1) KDR (VEGFR2) | Sorafenib Vatalanib | miR-578 miR-892b | T98G, U251 T98G, U251 | HA, 198G T98G |
| HDAC | HDAC5 | Vorinostat | miR-486-3p | HA, U251 | |
| | | Romidepsin | miR-506 | HA, U251 | |

Figure 5A:
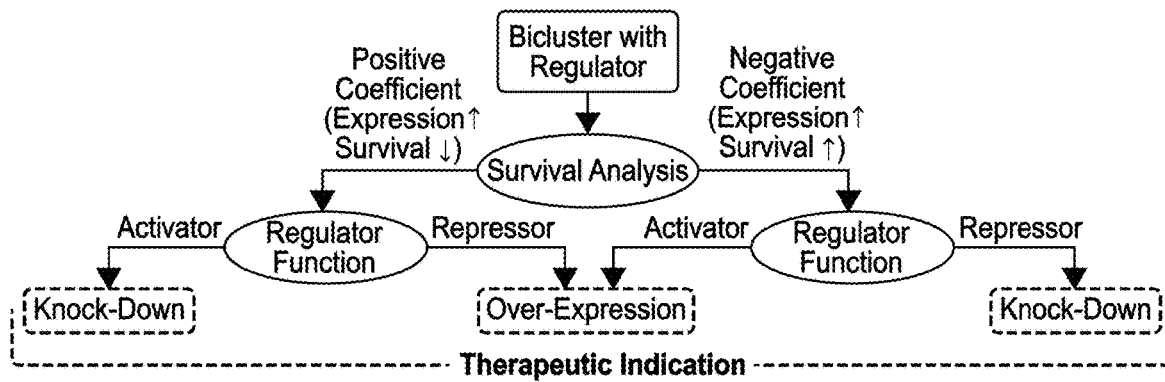
FIGS. 5A-5C. Determining the therapeutic indication for predicted regulators and the GBM subtype most likely to respond to treatment.

We selected romidepsin-miR-486-3p for further experimentation because romidepsin had the strongest effects on proliferation and apoptosis in every cell line, which explains why it is an attractive therapeutic candidate (Sawa et al., 2004; Sun et al., 2009). In the gbmSYGNAL network, both romidepsin and miR-486-3p target HDAC5, which is up-regulated in GBM patient tumors and known to increase proliferation of GBM cells (Liu et al., 2014). Therefore, we hypothesized that the potentially synergistic effect of romidepsin and miR-486-3p on HDAC5 would generate a stronger and longer-lasting treatment. We generated dose up-regulation of the TF IRF1 (p-value=$4.1 \times 10^{-4}$) that activates the expression of 27 genes within PITA 282 (p-value=$1.5 \times 10^{-2}$), which is associated with increased tumor lymphocyte infiltration and a worse prognosis. This data was particularly interesting because both NF1 and PIK3CA are known GBM driver mutations (Gonzalez-Perez et al., 2013). Up-regulation of IRF1 led to increased expression of the PITA_282 genes (R=0.67; p-value <$2.2 \times 10^{-16}$; FIG. 5C) and subtracting out the activation by IRF1 removed the causal influence of somatic mutations from NF1 and PIK3CA (p-value=0.79; FIG. 5D). Incorporation of somatic homozygous deletion of NF1 into these analyses reinforces these findings.

Furthermore, the IRF1 DNA recognition motif MA0050.1 was enriched within the promoters of 25 of the 27 genes (MA0050.1 TOMTOM q-value=$6.4\times10^{-7}$), demonstrating that IRF1 directly regulates these genes through binding to their promoter sequences. Based on the structure of the combinatorial regulatory network, IRF1 is a hub because it was included in 12 combinatorial models with as many distinct regulators, suggesting it may have additional functions when paired with other TFs. Knock-out of IRF1 in the CRISPR-Cas9 screen led to increased proliferation in the 0827 glioma stem cell isolate (fold-change=1.6 and FDR=$4.8\times10^{-2}$).

We rank-ordered patient tumors based on the median expression of PITA_282 bicluster genes enriched for specific GBM subtypes in the tails of the distribution. We found that the proneural subtype (including the G-CIMP phenotype) was highly enriched in the bottom quintile and the mesenchymal subtype was highly enriched in the upper two quintiles. Additionally, the PITA_282 bicluster was significantly associated with patient survival, where patients with tumors in the upper quintile had shorter survival on average relative to patients whose tumors were in the bottom quintile (HR=1.8; 95% CI=1.2-2.6; p-value=$1.2\times10^{-3}$).

The PITA 282 bicluster was associated with four hallmarks of cancer: tumor promoting inflammation, evading immune detection, self-sufficiency in growth signals, and insensitivity to antigrowth signals. More specifically, twelve of the 27 PITA 282 genes are involved in MHC class I antigen processing and presentation machinery (APM) (GO: 0002474 B-H p-value=$3.0\times10^{-9}$). Thus, we find that increased MHC class I APM is associated with reduced survival of GBM patients. A similar trend was observed in medulloblastoma where increased MHC class I APM was associated with unfavorable prognostic marker expression (Smith et al., 2009).

We then asked whether higher MHC class I APM expression in patient tumors had any impact on tumor lymphocyte infiltration as measured by pathological assessment (Rutledge et al., 2013). Tumors with tumor infiltrating lymphocytes had significantly increased IRF1 expression (p-value=$8.1\times10^{-4}$), and 15 of the 27 genes in PITA_282 had significantly increased expression with increased numbers of tumor infiltrating lymphocytes (p-value ≤0.05). The SYGNAL pipeline integrated multiple layers biological and clinical data into the gbmSYNAL network, and this allowed us to explain how somatic mutations in NF1 and PIK3CA up-regulate IRF1, which in turn activates the expression of downstream target genes that are associated with increased lymphocyte infiltration and worse patient survival.

Analysis

We developed the TF-target gene interaction database and the SYstems Genetics Network AnaLysis pipeline to construct transcriptional regulatory networks that model the influence of somatic mutations on TFs and miRNAs and consequently their downstream target genes. The SYGNAL pipeline is powerful because it is rooted in an integrative model that stitches together multi-omic and clinical patient data and incorporates mechanistic regulatory interactions which provide the means to maneuver the system back into a more healthy state. Using the rich multi-omic TOGA GBM dataset, we constructed the gbmSYGNAL network, and thereby discovered 67 novel regulators of GBM associated co-expression signatures (58 TFs and 9 miRNAs). Importantly, we demonstrated that the topology of the gbmSYG-NAL network can serve as a guide for discovering individual and combinations of regulatory factors that control proliferation and apoptosis, thereby providing a platform for identifying new anti-cancer interventions, including combination therapies with synergies. Furthermore, we demonstrate how the information rich gbmSYGNAL network can be used to gain new biological insights, such as the relationship between variability of tumor lymphocyte infiltration and patient survival (Rutledge et al., 2013).

Network understanding of a complex disease such as GBM as has been generated in this work provides a platform for the prioritization of TFs, miRNAs, drugs and their combinations as an alternative to unconstrained high-throughput screens. Our results, combined with findings from recent work (Bansal et al., 2014), demonstrate that it is feasible to predict synergistic compound pairs, and our discovery of a synergistic anti-proliferative effect (ETV6-NFKB1) from few tests provides proof-of-principle for using this approach to discover tailored combinatorial therapies matched to the characteristics of a patients disease.

The discovery of inhibitor-miRNA combinations using the gbmSYGNAL network took advantage of a similar principle that a synergistic interaction can emerge upon combining a miRNA mimic and an inhibitor that target the same oncogene (Choi et al., 2012). Using this principle, we identified a synergistic interaction between romidepsin and miR-486-3p, which can be attributed to the fact that they both target HDAC5 in the gbmSYGNAL network. Such synergistic combinations address at least two issues in using romidespin for cancer therapy. First, the short half-life of romidepsin in patients poses a significant challenge to keep the dosage at a level that is needed to effectively treat tumors (Iwamoto et al., 2011); combinations with other therapies that increase the efficacy of romidepsin could lengthen the effective treatment window and potentially lead to better therapeutic outcomes. Second, the synergism generates similar efficacy at a lower inhibitor dosage, which could in turn help to increase the specificity of the combination treatment, and lessen the toxic side-effects present at higher doses (Lehár et al., 2009).

We also demonstrated how the gbmSYGNAL network can be used to glean new biological insights by providing meaningful linkages across GBM driver mutations (NF1 and PIK3CA), differential regulation of regulators (IRF1) and their downstream genes associated with two hallmarks of cancer ('evading immune detection' and 'tumor promoting inflammation'), a cancer phenotype (tumor lymphocyte infiltration) and clinical outcome (shorter patient survival). It was previously known that mutations in NF1 significantly increased the number of tumor infiltrating lymphocytes, and that tumor infiltrating lymphocytes were enriched in the mesenchymal subtype (Rutledge et al., 2013). However, the mechanism by which NF1 mutations affected lymphocyte infiltration into tumors was not known. Through the gbm-SYGNAL network we were able to provide a mechanism for IRF1, a transcription factor that is characterized by being an integral part of the immune response, to regulate antigen processing and presentation genes, which could modify the recruitment of lymphocytes and other immune cells to the tumor. This example biological insight demonstrates how patient-derived data can be integrated into a platform that explains the etiology of a disease and provides a knob which can be turned to maneuver the system back to a more healthy state.

The use of small RNA molecules (siRNA, and miRNA mimics or inhibitors) in cancer therapy is attractive because they specifically manipulate the expression of one regulator, and thereby predictably impact many downstream oncogenic genes and processes (Heneghan et al., 2010). However, even as issues of stability and delivery of these RNA molecules across the blood brain barrier (in the case of GBM) are being solved (Karkan et al., 2008), there is still the challenge of determining which regulators to target. Designing combination therapy is even more complex and difficult because of the astronomically large numbers of possible combinations (Lehár et al., 2009). Thus, combinatorial regulation within the gbmSYGNAL network is a powerful framework to prioritize a smaller subset of TF, miRNA and drug combinations to screen for possible synergistic interactions. Although demonstrated for GBM, this strategy is broadly applicable, as tools developed for the construction of the gbmSYGNAL network are generalizable for constructing similar TRNs for any human disease directly from cross-sectional patient cohort data that include a compendium of transcriptome profiles.

Examples: Treatments for GMB Using Combination Therapies

The foregoing example identifies 87 combinations of regulators (TFs and/or miRNAs) to target for therapy.

We developed a set of guidelines to determine which TF and miRNA regulators would be useful as therapeutic targets and which GBM subtypes are most likely to respond to treatment. We created a decision tree that predicts the therapeutic indication (over-expression or knock-down) for a regulator based on information provided by the SYGNAL pipeline: 1) whether shorter patient survival is associated with increased or decreased bicluster expression direction, and 2) regulator function (activator or repressor) (FIG. 5A).

Figure 5B:
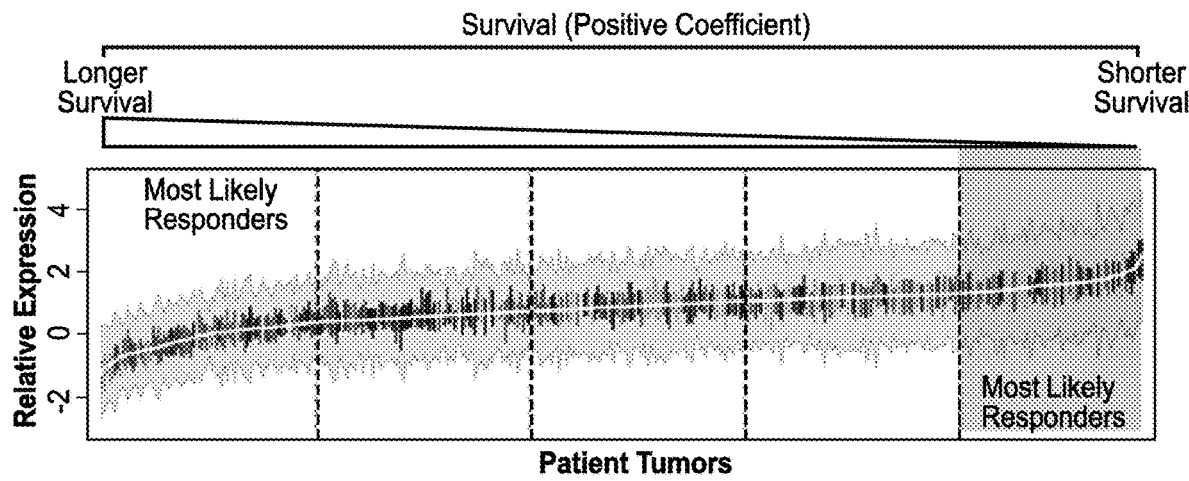
Figure 5C:
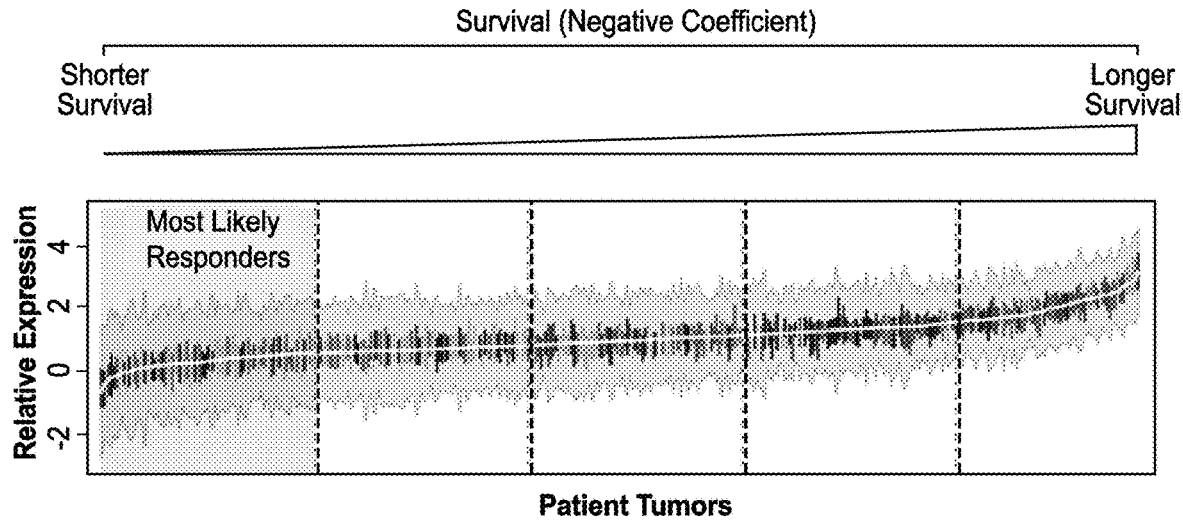

It is also possible to predict which GBM subtype(s) are most likely to respond to treatment with this therapeutic indication based on a combination of GBM subtype enrichment in the tails of bicluster expression and whether survival was associated with increased or decreased bicluster expression FIGS. 5B and 5C. We determined a therapeutic indication of over-expression for 33 TFs and 17 miRNAs, knock-down for 30 TFs and 10 miRNAs, and 6 TFs and 2 miRNAs had indications for over-expression and knock-down for different biclusters. We identified 123 regulators that could be targeted for the mesenchymal subtype, 33 regulators for neural, 17 regulators for classical, 4 regulators for G-CIMP, and 1 regulator for proneural. By using these guidelines it is possible to rationally predict whether to over-express or knock-down TFs or miRNAs and to predict which GBM subtypes are most likely to respond to treatment.

Using the foregoing approach to analyzing regulators, and the combinations of regulators identified in the preceding example, we identified a number of combinations as immediately amenable to treatment using targeted oligonucleotides. For instance, transcription factors to be targeted for knock-down can be targeted using inhibitory nucleic acids described herein, including siRNA and antisense nucleic acids, for knock-down. On the other hand, because miRNA are small RNA molecules, both knock-down (miRNA inhibitor) and over-expression (replacement/replenishment with miRNA or mimetic mimic) are possible. Consequently, combinations in which TFs are identified for knock-down and miRNA are identified for either knock-down or replenishment/over-expression are all amenable to treatment with combinations of oligonucleotides. Over half of the combinations (48 of the 87) identified above can be targeted using this approach of using only small RNA molecules or other oligonucleotides. Each line in the following table represents such a combination of targets:

| Regulators to Knockdown | Regulators to Over-Express |
|---|---|
| NFKB1 | hsa-miR-181d |
| NFKB1 | hsa-miR-139 |
| IRF1 + IKZF1 | |
| hsa-miR-142-5p + hsa-miR-152 + hsa-miR-223 + hsa-miR-34a + hsa-miR-146b | |
| PPARG + ETV7 | |
| hsa-miR-142-5p + hsa-miR-223 + hsa-miR-27a | |
| NFKB1 | hsa-miR-181d |
| IRF1 | hsa-miR-133a |
| | hsa-miR-106b + hsa-miR-17-5p |
| hsa-miR-142-5p + hsa-miR-223 + hsa-miR-146b | |
| | hsa-miR-181d + hsa-miR-181a-3p + hsa-miR-128a |
| hsa-miR-15b + TCF3 | |
| hsa-miR-27a + hsa-miR-513 + hsa-miR-23a | |
| ZNF217 + hsa-miR-27a + hsa-miR-452 + hsa-miR-142-5p + hsa-miR-513 + hsa-miR-223 | |
| ZIC5 + ETV7 | |
| KLF6 + CEBPE + CEBPD | |
| TBX10 + hsa-miR-23a | |
| hsa-miR-34a + hsa-miR-146b | |
| NFKB1 + IRF1 | |
| | hsa-miR-181d + hsa-miR-324-5p |
| ELF1 + ETV7 + ETV6 | |
| | hsa-miR-139 + hsa-miR-138 + hsa-miR-133a + hsa-miR-133b |
| ELF1 + ETV6 | |
| ELK3 + ETV6 | |
| NFKB1 + ETV6 | |
| IRF1 | hsa-miR-181d |
| ELF1 + PPARG + IRF1 | |
| ELF1 + IRF1 | |
| hsa-miR-142-5p + hsa-miR-513 + hsa-miR-223 + hsa-miR-27a | |
| ETV7 | hsa-miR-181d |
| ELF1 + ETV7 | |
| hsa-miR-25 + hsa-miR-15b | |
| IRF1 + ETV6 | |
| hsa-miR-142-5p + hsa-miR-223 + hsa-miR-23a + hsa-miR-27a | |
| ELF1 + ETV7 | |
| ELF1 + IRF1 | |
| KLF17 + KLF1 | |
| IRF1 + IKZF1 | |
| ELF1 + PPARG | |
| TFAP2C + hsa-miR-34a + RARG | |
| SMAD9 + TFCP2L1 | |
| ELF1 + IRF1 | |
| hsa-miR-25 + hsa-miR-15b | |
| | hsa-miR-19a + hsa-miR-19b |
| IRF1 | hsa-miR-133a |
| PPARG | hsa-miR-106b |
| | hsa-miR-106a + hsa-miR-106b + hsa-miR-130b + hsa-miR-17-5p |
| hsa-miR-142-5p + hsa-miR-452 + hsa-miR-223 + hsa-miR-513 + hsa-miR-27a | |

All of these specific combination therapies are specifically contemplated as aspects of the invention, both as methods of treatment and as compositions and combinations of therapeutic agents.

The efficacy of single agent and combination therapies can be evaluated in cell lines as described above, and then in animal models for GBM. See, e.g., Chen et al., "Vertebrate animal models of glioma: understanding the mechanisms and developing new therapies." *Biochim Biophys*

*Acta.* (2013 August); 1836(1):158-65; Oh et al., "Immunocompetent murine models for the study of glioblastoma immunotherapy." *J Transl Med.* (2014 Apr. 29); 12:107; and Welker et al., "Standardized orthotopic xenografts in zebrafish reveal glioma cell-line-specific characteristics and tumor cell heterogeneity." *Dis Model Mech.* (2016 Feb. 1); 9(2):199-210, all incorporated herein by reference in their entirety and specifically with respect to glioblastoma animal models and protocols.

In additional experiments, the foregoing agents, singly or in the specified combinations, are tested in the animal models in combination with existing standard-of-care therapeutics.

Transcription Factors

A "transcription factor" is a sequence-specific DNA-binding protein that, through binding to DNA, alters the rate of transcription of DNA into messenger RNA. Transcription factors contain one or more DNA binding domains and typically bind to enhancer or promoter regions of genes that they regulate. Defining characteristics include the presence of a DNA-binding domain that recognizes and binds specific enhancer or promoter sequences of genes; and a trans-activating domain which may contain binding sites for other proteins (transcription coregulators). Some transcription factors bind to a DNA promoter sequence near the transcription start site and help form the transcription initiation complex. Other transcription factors bind to regulatory sequences, such as enhancer sequences, and can either stimulate or repress transcription of the related gene. The sequences to which TFs bind can be thousands of base pairs upstream or downstream from the gene that is regulated through the binding.

Approximately 8% of human genes encode transcription factors, which play important roles in development, cell cycle, and health/disease. Several human diseases are linked to mutations in transcription factors. Numerous TFs from humans and other species have been described and characterized, with information found in publicly available databases such as GenBank. See, e.g., http-colon-slash-slash-www.transcriptionfactor.org/. An extensive database of TFs, organized by the structure of DNA binding domains, can be found on the internet at http (colon-slash-slash) tfclass.bio-inf.med.uni-goettingen.de/tfclass. See also Wingender et al., "TFClass: An expandable hierarchical classification of human transcription factors." *Nucleic Acids Res.* 41, D165-D170 (2013), both incorporated herein by reference in their entireties.

Of particular interest to some embodiments of the invention are transcription factors listed in the following Transcription Factor Table:

TRANSCRIPTION FACTOR TABLE

| TF | Entrez ID | Genbank Protein ID |
|---|---|---|
| ASCL2 | 430 | AAB39362; AAI36568; AAI36562; AAH57801; AAL35362; AAB86993 |
| CEBPD | 1052 | AAI05110; EAW86679; AAB27293; AAA59927 |
| CEBPE | 1053 | AAH35797; AAC50709; AAC51130; AAC50708 |
| CREB1 | 1385 | AAD13869; AAH10636; AAQ24858; CAA42620; AAA35715; AAA35716; AAA35717; CAA39151; AAB20597; EAW70407; EAW70409; CAG28545; EAW70406; BAG37655; AAH95407; EAW70410; BAG35615; EAW70405; AAV38316 |
| E2F7 | 144455 | BAG53257; BAG53510; AAI36368; AAI36367; AAH16658 |
| ELF1 | 1997 | AAH30507; EAX08640; CAI13220; BAG65147; EAX08641; CAE45881 |
| ELK3 | 2004 | AAH17371; EAW97561; BAG35573; CAG47047; CAA85309; EAW97565; EAW97564; EAW97563; EAW97562 |
| ETS2 | 2114 | AAA52411; CAA38966; AAH42954; AAH17040; EAX09676; EAX09674; EAX09673; BAA95514; CAB90468; AAP35484; BAG37939; AAB94057; AAA52412 |
| ETV6 | 2120 | ABI30005; AAB17135; AAB17134; AAC50690; AAH43399; EAW96240; BAF82130; AAA19786 |
| ETV7 | 51513 | AAH35853; EAX03890; EAX03888; EAX03885; CAI21616; CAI21615; BAG64776; BAG62628; BAG53734; CAC17012; AAD33989; AAF25007; AAF44743; AAF44742; AAF28350; AAD43252; AAD43251; AAD43250 |
| GABPA | 2551 | AAA65706; BAA02575; EAX09968; EAX09969; AFH41795; EAX09967; ABV90873; ACD11490 |
| IKZF1 | 10320 | AAH18349; EAW60979; EAL23900; EAW60981; EAW60978; EAW60977; AAP88838; BAG64603; AAR84585; AAB50683; AAC50459; CAJ29975; AGI59420 |
| IRF1 | 3659 | AAH09483; AAV38561; AAA36043; CAA32624; EAW62332; CAG46514; ABH05670; BAG36735; AAV38560; AGV15458 |
| JUNB | 3726 | AAH09466; AAH09465; AAH04250; AAU43800; AAA74915; CAA35738; AAA59198; EAW84307; BAG36478; AAV38565 |
| KLF1 | 10661 | AAH33580; AAB51173; AAC51108; AAC50562 |
| KLF17 | 128209 | AAH49844; CAI15911; BAC05070 |
| KLF2 | 10365 | AAH71983; ABK41959; AAF13295; AAD55891; AAD25076 |
| KLF6 | 1316 | AAH00311; EAW86479; EAW86477; CAH71011; CAH71010; CAH74050; BAG38183; BAG56791; CAH74049; AAP35424; AAM73548; BAA33050; AAC39929; AAC23699 |
| LEF1 | 51176 | AAH50632; AAH40559; EAX06225; EAX06223; BAH13928; BAG57649; AAG26886; AAF13268; AAG01022; EAX06224; EAX06222 |
| MAFB | 9935 | AAH36689; AAH28098; EAW76000; CAB75863; BAG51303; AAD30106 |
| NFIA | 4774 | AAA93124; EAX06601; AAH22264; BAG61305; BAG61515; BAA92677 |
| NFKB1 | 4790 | AAH33210; AAH51765; CAH18336; AAO30127; BAG53760; BAF84139; CAB94757; AAF35232; AAA36361; AAA36360; EAX06136; EAX06135 |
| NR2F1 | 7025 | AAH17493; AAH04154; CAA31283; CAA34277; ADZ17390 |
| PPARG | 5468 | EAW64124; AAH06811; AAN38992; BAG70151; BAG70300; AAP35945; BAF83270; CAA62153; ABC97372; BAA23354; CAA62152; BAA18949; AAA80314; AAC51248; AAB04028; EAW64123; BAM71699; ADZ17377; BAI63629 |
| RARG | 5916 | AAG41595; CAB60726; AAG41594; AAA60253; CAA40548; AAH93727; AAH93729; BAH14630; EAW96676; BAH12478; BAH12537; AAA63254; AAA60254; AAA52692; EAW96678; EAW96677; BAH02280; BAF83277; ADZ17339; ADZ17340 |
| RELB | 5971 | AAH28013; AAC82346; ABC40746; AAA36127; EAW57316 |

-continued

TRANSCRIPTION FACTOR TABLE

| TF | Entrez ID | Genbank Protein ID |
| --- | --- | --- |
| RUNX3 | 864 | AAH13362; AAA86465; CAI20422; EAW95148; CAA18856; CAC42093; CAA84541; CAA56093; EAW95149 |
| SMAD9 | 4093 | AAI04763; AAI43241; AAH11559; AAI04761; EAX08572; CAM19158; EAX08571; BAA21129; CAI14007; BAA21128; EAX08573 |
| SOX9 | 6662 | AAH07951; AAH56420; AAP35521; EAW89102; CAA86598; AAB32870 |
| TBX10 | 347853 | AAI13488; AAC23481; AAO73483; AAI13486 |
| TCF3 | 6929 | AAC41693; AAA56830; CAA36297; AAI10581; AAA56829; AAC27373; AAI10580; AAA52331; AAC99797; AAA61146; AAA36764 |
| TEAD2 | 8463 | AAH07556; CAA64214; EAW52469; AAH51301; BAF83425; BAG62008; BAC04104; EAW52471 |
| TFAP2C | 7022 | AAH51829; BAC11805; AAH35664; CAC10334; BAG63065; CAC86997; AAC51305; CAA64989 |
| TFCP2L1 | 29842 | AAX88871; AAH64698; AAF32275 |
| ZHX3 | 23051 | AAH68569; EAW75988; EAW75987; CAA18538; BAA23691; BAC65211 |
| ZIC5 | 85416 | CAH70366; AAK55418 |
| ZNF217 | 7764 | AAI13428; EAW75580; CAC08433; AAC39895 |

Therapeutic Agents Targeting Nucleic Acids

In some variations of the invention, a therapeutic agent is selected and/or administered that targets, mimics, or comprises a gene regulator identified as relevant to a subject's neoplastic condition.

In some embodiments, the therapeutic agent is a nucleic acid. As used herein, a "nucleic acid" or a "nucleic acid molecule" means a chain of two or more nucleotides such as RNA (ribonucleic acid) and DNA (deoxyribonucleic acid), and chemically-modified nucleotides. Nucleic acid molecules may be in the form of RNA (e.g., mRNA, microRNA, siRNA, shRNA or synthetic chemically modified RNA) or in the form of DNA (e.g., cDNA, genomic DNA, and synthetic DNA). The DNA may be double-stranded or single-stranded, and if single-stranded, may be a coding (sense) strand or a non-coding (anti-sense) strand. RNA may also be present in double-stranded form, if desired. The nucleic acid need not be double-stranded over the entire length of the molecule (i.e., a single strand of nucleic acid may be hybridized to a second strand over a subregion of its sequence).

siRNA

In some embodiments, the nucleic acid is an siRNA molecule. In some embodiments, the siRNA molecule has a length from 5-60 (e.g., about 10-50) nucleotides, i.e., each strand comprises 5-60 (e.g., 10-50) nucleotides (or nucleotide analogs), although molecules having more than 60 nucleotides in length also are contemplated. In some embodiments, the siRNA molecule has a length from about 5-15 (e.g., 5, 6, 7, 8, 9, 10, 11, 12, 13, 14, or 15); about 16-30 (e.g., 16, 17, 18, 19, 20, 21, 22, 23, 24, 25, 26, 27, 28, 29, or 30); about 18-25 (e.g., 18, 19, 20, 21, 22, 23, 24, or 25); about 25-30 (e.g., 25, 26, 27, 28, 29, or 30); about 25-35 (e.g., 25, 26, 27, 28, 29, 30, 31, 32, 33, 34 or 35); about 30-35 (e.g., 30, 31, 32, 33, 34 or 35); or about 30-60 (e.g., 35, 40, 45, 50, 55, or 60) nucleotides in each strand, wherein one of the strands is sufficiently complementary to a target region, and the other strand is identical or substantially identical to the first strand (e.g., having 5 or fewer (e.g., 1, 2, 3, or 4) mismatches relative to the first strand.

In some embodiments, the strands of the siRNA molecule are of different lengths (e.g., they differ in length by 5 or fewer nucleotides (e.g., 1, 2, 3, or 4). In other embodiments, the strands of the siRNA molecule are of the same length.

In some embodiments, the strands of the siRNA molecule are aligned such that one or both ends of the siRNA molecule are blunt-ended (i.e., lack an overhang). In other embodiments, the strands of the siRNA molecule are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. In certain embodiments, at least one (preferably both) ends of the duplex comprise a 2 nucleotide overhang (e.g., dTdT overhangs).

In some embodiments, the sense strand of the siRNA is designed to have a sequence sufficiently identical to a portion of the target gene sequence. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is contemplated. In some embodiments, the sense strand has 4, 3, 2, 1, or 0 mismatched nucleotide(s) with a target region, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition. Sequence identity between one or more nucleic acid sequences may be determined by sequence comparison and alignment algorithms known in the art, such as BLAST and CLUSTALW.

miRNA

In some embodiments, a gene regulator of interest is a microRNA (miRNA), a term that refers to short RNA molecules found in eukaryotes that are involved in RNA-based gene regulation. Generally, miRNAs are noncoding RNAs of approximately 20-25 (e.g., 22) nucleotides that regulate gene expression at the post-transcriptional level, including involvement in RNA silencing. The miRNA functions through base-pairing with complementary sequences, e.g., in an mRNA molecule. Following the base-pairing (binding/annealing), translation of the mRNA is reduced or silenced, typically through cleavage of the mRNA, destabilization of the mRNA, deadenylation, and/or reduction in translation efficiency by ribosomes. An miRNA only needs to pair partially to its target mRNA to elicit translational repression. The seed or an miRNA has been defined as nucleotides 2-8 of the miRNA. A large fraction of the targets of miRNAs have, in their 3'UTRs, perfect Watson-Crick complementary sites to the seed of the miRNA.

The miRNA sequence can be identical to that of any naturally occurring miRNA (see e.g. The miRNA Registry; Griffiths-Jones S, Nuc. Acids Res., 2004) or a mimetic with a highly similar sequence. More than one thousand natural miRNAs have been identified to date in humans and together they are thought to comprise about 1% of all predicted genes in the genome.

Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004).

Information about miRNA species, including those specifically mentioned herein, is published, for example, at miRBase (http colon-slash-slash www.mirbase.org/); and the MIRIAM Registry (http colon-slash-slash www.ebi-.ac.uk/miriam/main/collections/MIR:00000078)

Of particular interest to some embodiments of the invention are miRNA listed in the following miRNA Table:

miRNA Table

| miRNA Name | miRBase ID | Sequence 5'-3' | SEQ ID NO: |
|---|---|---|---|
| hsa-miR-106a-5p | MIMAT0000103 | AAAAGUGCUUACAGUGCAGGUAG | 1 |
| hsa-miR-106b-5p | MIMAT0000680 | UAAAGUGCUGACAGUGCAGAU | 2 |
| hsa-miR-128-1-5p | MIMAT0026477 | CGGGGCCGUAGCACUGUCUGAGA | 3 |
| hsa-miR-128-1-5p | MIMAT0026477 | CGGGGCCGUAGCACUGUCUGAGA | 4 |
| hsa-miR-130b-5p | MIMAT0004680 | ACUCUUUCCCUGUUGCACUAC | 5 |
| hsa-miR-133a-5p | MIMAT0026478 | AGCUGGUAAAAUGGAACCAAAU | 6 |
| hsa-miR-133b | MIMAT0000770 | UUUGGUCCCCUUCAACCAGCUA | 7 |
| hsa-miR-138-5p | MIMAT0000430 | AGCUGGUGUUGUGAAUCAGGCCG | 8 |
| hsa-miR-139-5p | MIMAT0000250 | UCUACAGUGCACGUGUCUCCAGU | 9 |
| hsa-miR-142-5p | MIMAT0000433 | CAUAAAGUAGAAAGCACUACU | 10 |
| hsa-miR-146b-5p | MIMAT0002809 | UGAGAACUGAAUUCCAUAGGCU | 11 |
| hsa-miR-152-5p | MIMAT0026479 | AGGUUCUGUGAUACACUCCGACU | 12 |
| hsa-miR-15b-5p | MIMAT0000417 | UAGCAGCACAUCAUGGUUUACA | 13 |
| hsa-miR-17-5p | MIMAT0000070 | CAAAGUGCUUACAGUGCAGGUAG | 14 |
| hsa-miR-181a-3p | MIMAT0000270 | ACCAUCGACCGUUGAUUGUACC | 15 |
| hsa-miR-181c-5p | MIMAT0000258 | AACAUUCAACCUGUCGGUGAGU | 16 |
| hsa-miR-181d-5p | MIMAT0002821 | AACAUUCAUUGUUGUCGGUGGGU | 17 |
| hsa-miR-19a-5p | MIMAT0004490 | AGUUUUGCAUAGUUGCACUACA | 18 |
| hsa-miR-19b-1-5p | MIMAT0004491 | AGUUUUGCAGGUUUGCAUCCAGC | 19 |
| hsa-miR-21-5p | MIMAT0000076 | UAGCUUAUCAGACUGAUGUUGA | 20 |
| hsa-miR-222-5p | MIMAT0004569 | CUCAGUAGCCAGUGUAGAUCCU | 21 |
| hsa-miR-223-5p | MIMAT0004570 | CGUGUAUUUGACAAGCUGAGUU | 22 |
| hsa-miR-23a-5p | MIMAT0004496 | GGGGUUCCUGGGGAUGGGAUUU | 23 |
| hsa-miR-25-5p | MIMAT0004498 | AGGCGGAGACUUGGGCAAUUG | 24 |
| hsa-miR-27a-5p | MIMAT0004501 | AGGGCUUAGCUGCUUGUGAGCA | 25 |
| hsa-miR-324-5p | MIMAT0000761 | CGCAUCCCCUAGGGCAUUGGUGU | 26 |
| hsa-miR-34a-5p | MIMAT0000255 | UGGCAGUGUCUUAGCUGGUUGU | 27 |
| hsa-miR-452-5p | MIMAT0001635 | AACUGUUUGCAGAGGAAACUGA | 28 |
| hsa-miR-513a-5p | MIMAT0002877 | UUCACAGGGAGGUGUCAU | 29 |

Naturally-occurring miRNAs are expressed by endogenous genes in vivo and are processed from a hairpin or stem-loop precursor (pre-miRNA or pri-miRNAs) by Dicer or other RNAses. MiRNAs can exist transiently in vivo as a double-stranded duplex, but only one strand is taken up by the RISC complex to direct gene silencing. Synthetic miRNA mimetics based at least in part on naturally-occurring miRNA sequences are contemplated for use in the context of the invention.

In some embodiments, the nucleic acid is an antagomiR or an RNA sponge. Antagomirs are chemically modified oligonucleotides that bind specifically to and silence particular microRNAs. An RNA sponge is a small synthetic RNA that bind to multiple microRNAs that have the same sequence in their 'seed region'.

Adaption of miRNAs (and other oligonucleotides) for therapy, including approaches for synthesis and delivery, has been described extensively in patent and journal scientific literature, including Rooij and Kauppinen, "Development of microRNA therapeutics is coming of age," *EMBO Mol Med.*, (2014 July); 6(7): 851-864, incorporated herein by reference in its entirety.

shRNA

In some embodiments, the nucleic acid is a short hairpin RNA (shRNA). In contrast to siRNAs, shRNAs mimic the natural precursors of microRNAs (miRNAs) and enter at the top of the gene silencing pathway. The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. In some embodiments, the stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In some embodiments, the length of the stem portions is 21 nucleotides or greater. When used in mammalian cells, the length of the stem portions are preferably less than about 30 nucleotides to avoid provoking non-specific responses like the interferon pathway. In non-mammalian cells, the stem can be longer than 30 nucleotides.

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (U's), e.g., all U's. The loop in the shRNAs can be 2, 3, 4, 5, 6, 7, 8, 9, or more, e.g., 15 or 20, or more nucleotides in length.

A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In some embodiments, shRNAs include the sequences of a desired siRNA molecule described above. In some embodiments, the sequence of the antisense portion of a shRNA can be designed essentially as described above or generally by selecting an 18, 19, 20, 21 nucleotide, or longer, sequence from within the target RNA, for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA, siRNA-like duplex, or miRNA desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro. In certain embodiments, shRNAs may include miRNA sequences, optionally end-modified miRNA sequences, to enhance entry into RISC. For purposes of the invention, it should be understood that administration of a precursor that is processed to form a therapeutic RNA in vivo is considered to be administration of the therapeutic RNA.

Antisense Nucleic Acids

In some embodiments, the nucleic acid molecule is an antisense nucleic acid molecule that is complementary to a target mRNA or to a portion of the mRNA, or a recombinant expression vector encoding the antisense nucleic acid molecule. Antisense nucleic acid molecules are generally single-stranded DNA, RNA, or DNA/RNA molecules which may comprise one or more nucleotide analogs. The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986). An antisense nucleic acid molecule comprises a nucleotide sequence that is complementary to the target mRNA sequence and accordingly is capable of hydrogen bonding to the mRNA. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Preferably, an antisense nucleic acid is designed so as to be complementary to a region preceding or spanning the initiation codon in the 3' untranslated region of an mRNA.

Given the known nucleotide sequence of a target mRNA, antisense nucleic acids of the invention can be designed according to the rules of Watson and Crick base pairing. The antisense nucleic acid molecule can be complementary to the entire coding region of an mRNA, but more preferably is antisense to only a portion of the coding or noncoding region of an mRNA. For example, the antisense oligonucleotide can be complementary to the region surrounding the translation start site of a target mRNA. An antisense oligonucleotide can be, for example, about 5, 10, 15, 20, 25, 30, 35, 40, 45, 50, 60, 70, 80, 100, 500, 1000 nucleotides or more in length. In some embodiments, the antisense oligonucleotide may be as long as, or longer than, the length of the mRNA that is targeted.

In some embodiments, antagomirs are contemplated. Exemplary antagomirs are 3' cholesterol-conjugated, 2'-O-methyl-modified antisense oligonucleotides that inhibit miRNA function. In some variations, antagomirs are fully complementary to mature miRNAs, such as mRNA's to be inhibited according to embodiments of the invention.

In some embodiments, antimiR molecules are contempled: chemically modified, single-stranded antisense oligonucleotides that inhibit miRNA function, and whose length ranges from 8-mer oligonucleotides that target the seed region of an miRNA to antimiRs that are fully complementary to mature miRNAs.

miRNA Traps/Sponges

In some embodiments, a therapeutic comprising multiple binding sights for an miRNA of interest is contemplated. Such miRNA "traps" or "sponges" serve to downregulate miRNA activity by binding endogenous copies of the miRNA. In some variations, the trap is synthesized ex vivo and administered as a therapeutic. In some variations, an expression vector is administered to cause transgenic overexpression of RNA harboring multiple miRNA binding sites.

Synthetic Nucleic Acids

Chemical modifications of nucleic acids may lead to increased stability, e.g., increased or enhanced in vivo stability, compared to an unmodified nucleic acid. Such chemical modifications can be used to stabilize the first (priming) strand of an siRNA for enhancing RISC activity/RNA silencing responsiveness in a cell (or cell extract or organism) and improve its intracellular half-life for subsequent receipt of the second strand wherein RNA silencing/gene silencing can now progress.

Modifications can also enhance properties such as cellular uptake of the RNA silencing agents and/or stability of the RNA silencing agents, can stabilize interactions between base pairs, and can maintain the structural integrity of the antisense RNA silencing agent-target RNA duplex. RNA silencing agent modifications can also be designed such that properties important for in vivo applications, in particular, human therapeutic applications, are improved without compromising the RNA silencing activity of the RNA silencing agents e.g., modifications to increase resistance of, for example, siRNA or miRNA molecules to nucleases. In some embodiments, modified siRNA molecules of the invention can enhance the efficiency of target RNA inhibition as compared to a corresponding unmodified siRNA. In some embodiments, modified nucleotides do not affect the ability of the antisense strand to adopt A-form helix conformation when base-pairing with the target RNA sequence, e.g., an A-form helix conformation comprising a normal major groove when base-pairing with the target RNA sequence.

Chemical modifications generally include end-, sugar-, base- and/or backbone-modifications to the ribonucleotides (i.e., include modifications to the phosphate-sugar backbone). In one embodiment, the RNA silencing agent of the invention comprises one or more (e.g., about 1, 2, 3, or 4) end modifications. For example, modification at the 5' end of an siRNA molecule comprises, for example, a 5'-propylamine group. Modifications to the 3'-OH terminus of an siRNA molecule can include, but are not limited to, 3'-puromycin, 3'-biotin (e.g., a photocleavable biotin), a peptide (e.g., a Tat peptide), a nanoparticle, a peptidomimetic, organic compounds (e.g., a dye such as a fluorescent dye), or a dendrimer. End modifications may be on the sense strand, on the antisense strand or both. In some embodiments, the 5' modifications are on the sense strand only.

In some embodiments, the nucleic acid comprises one or more (e.g., about 1, 2, 3, 4, 5, 6, 7, 8, 9, 10, or more) sugar-modified nucleotides. Sugar-modified nucleotides include, but are not limited to: 2'-fluoro modified ribonucleotides, 2'-OMe modified ribonucleotides, 2'-deoxy ribonucleotides, 2'-amino modified ribonucleotides and 2'-thio modified ribonucleotides. The sugar-modified nucleotide can be, for example, 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine or 2'-amino-butyryl-pyrene-uridine. In one embodiment, the sugar-modified nucleotide is a 2'-fluoro ribonucleotide. In some embodiments, when a 2'-deoxy ribonucleotide is present, it is upstream of the cleavage site referencing the antisense strand or downstream of the cleavage site referencing the antisense strand. The 2'-fluoro ribonucleotides can be in the sense and antisense strands. In some embodiments, the 2'-fluoro ribonucleotides are every uridine and cytidine. In other embodiments, the 2'-fluoro ribonucleotides are only present at the 3' and 5' ends of the sense strand, the antisense strand or both.

In some embodiments, the nucleic acid comprises one or more (e.g., about 1, 2, 3, 4, 5, 6, 7, 8, 9, 10, or more) nucleobase-modified nucleotides. Nucleobase-modified nucleotides useful in the invention include, but are not limited to: uridine and/or cytidine modified at the 5-position (e.g., 5-bromo-uridine, 5-(2-amino)propyl uridine, 5-amino-allyl-uridine, 5-iodo-uridine, 5-methyl-cytidine, 5-fluoro-cytidine, and 5-fluoro-uridine), ribo-thymidine, 2-aminopurine, 2,6-diaminopurine, 4-thio-uridine, adenosine and/or guanosines modified at the 8 position (e.g., 8-bromo guanosine), deaza nucleotides (e.g., 7-deaza-adenosine), 0- and N-alkylated nucleotides (e.g., N6-methyl adenosine) and non-nucleotide-type bases (e.g., deoxy-abasic, inosine, N3-methyl-uridine, N6, N6-dimethyl-adenosine, pseudouridine, purine ribonucleoside and ribavirin).

In some embodiments, the nucleic acid comprises one or more (e.g., about 1, 2, 3, 4, 5, 6, 7, 8, 9, 10, or more) backbone-modified nucleotides. Exemplary backbone-modified nucleotides contain a phosphorothioate group or a phosphorodithioate. In another embodiment, a backbone modification of the invention comprises a phosphonoacetate and/or thiophosphonoacetate internucleotide linkage (see for example Sheehan et al., 2003, Nucleic Acids Research, 31, 4109-4118). The backbone-modifications can be within the sense strand, antisense strand, or both the sense and antisense strands. In some embodiments, only a portion of the internucleotide linkages are modified in one or both strands. In other embodiments, all of the internucleotide linkages are modified in one or both strands. In one embodiment, the modified internucleotide linkages are at the 3' and 5' ends of one or both strands.

In some embodiments, the nucleic acid may comprise one or more (e.g., about 1, 2, 3, 4, 5, 6, 7, 8, 9, 10, or more) crosslinks, e.g., a crosslink wherein the sense strand is cross-linked to the antisense strand of the siRNA duplex. Known cross-linkers include psoralen, mitomycin C, cisplatin, and chloroethylnitrosoureas. In one embodiment, the crosslink of the invention is a psoralen crosslink. Preferably, the crosslink is present downstream of the cleavage site referencing the antisense strand, and more preferably, the crosslink is present at the 5' end of the sense strand.

In some embodiments, the nucleic acid comprises a nucleotide sequence wherein the antisense strand and target mRNA sequences comprise one or more (e.g., about 1, 2, 3, 4, 5, 6, 7, 8, 9, 10, or more) mismatches. In some embodiments, the mismatch is downstream of the cleavage site referencing the antisense strand, e.g., within 1-6 nucleotides from the 3' end of the antisense strand. In another embodiment, the nucleic acid molecule, e.g., RNA silencing agent, of the invention is an siRNA molecule that comprises a bulge, e.g., one or more (e.g., about 1, 2, 3, 4, 5, 6, 7, 8, 9, 10, or more) unpaired bases in the duplex siRNA. In some embodiments, the bulge is in the sense strand.

In some embodiments, locked nucleic acids (LNA) are employed. An exemplary LNA comprises a high-affinity RNA analogue, in which the ribose sugar is locked in a C3'-endo conformation by introduction of a 2'-0,4'-C methylene bridge.

In some embodiments, morpholino oligomers are utilized. Morpholino oligomers comprise a class of chemically modified antisense oligonucleotides, in which six-membered morpholine rings replace the sugar moieties and non-ionic phosphorodiamidate linkages replace the phosphate linkages.

In some embodiments peptide nucleic acids (PNA) are utilized. PNA oligomers comprise uncharged oligonucleotide analogues, in which the sugar-phosphate backbone has been replaced by a peptide-like backbone consisting of N-(2-aminoethyl)-glycine units.

In some embodiments, miRNA silencing is improved through chemical modification to improve binding affinity, stability, and/or pharmacokinetics. In some variations, sugar modifications for increasing the duplex melting temperature (Tm) and/or improving nuclease resistance of antimiRs are utilized. Such modifications include 2'-O-methyl (2'-O-Me), 2'-O-Methoxyethyl (2'-MOE) 2'-fluoro, and bicyclic locked nucleic acid (LNA) modifications. In some variations, increased nuclease resistance is achieved by substituting phosphorothioate (PS) linkages for phosphodiester (PO) backbone linkages, or by using peptide nucleic acid (PNA) or morpholino oligomers. PS backbone modifications also enhance binding to plasma proteins, leading to improved pharmacokinetics (reduced clearance). PNA oligomers are uncharged oligonucleotide analogues, in which the sugar-phosphate backbone has been replaced by a peptide-like backbone consisting of N-(2-aminoethyl)-glycine units. See Rooij and Kauppinen, "Development of microRNA therapeutics is coming of age," *EMBO Mol Med.*, (2014 July); 6(7): 851-864, and documents cited therein, all incorporated herein by reference.

The modifications described herein can be used in any combination to provide a modified nucleic acid.

Nucleic acids may be modified according to methods described in the art (Amarzguioui et. al., Nuc. Acids. Res., (2003) 31: 589-95; Chiu and Rana, RNA, (2003), 9: 1034-48; Chiu and Rana, Mol. Cell., (2002), 10: 549-61); Morrissey et al., Nat. Biotech., (2005), 23: 2002-7), each of which is incorporated by reference herein. In one embodiment, the nucleic acid is conjugated a lipophilic moiety. In one embodiment, the lipophilic moiety is a ligand that includes a cationic group. In another embodiment, the lipophilic moiety is attached to one or both strands of an siRNA. In a preferred embodiment, the lipophilic moiety is attached to one end of the sense strand of the siRNA. In another preferred embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In a preferred embodiment, the lipophilic moiety is a cholesterol. Other lipophilic moieties include cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine. In some embodiments, the Rnucleic acid may also contain a nuclear localization/nuclear targeting signal(s). Such modifications may be made exclusive of, or in addition to, any combination of other modifications as described herein. Nuclear targeting signals include any art-recognized signal capable of effecting a nuclear localization to a molecule, including, for example, NLS signal sequence peptides.

Synthetic nucleic acids (e.g., an antisense oligonucleotides) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In some embodiments of the invention, synthetic RNA duplexes are used to therapeutically restore a desired miRNA activity in cells. In some variations, the synthetic RNA duplexes harbor chemical modifications to improve stability and cellular uptake. For example, the strand identical to the miRNA of interest—the guide (antisense) strand—is modified for stability, and the opposite strand (passenger or sense strand) is synthesized to be less stable. The passenger strand optionally is linked to a molecule, such as cholesterol, to enhance cellular uptake. In some variations, the passenger strand is chemically modified to prevent RISC loading, though largely left unmodified to facilitate rapid degradation. Since the miRISC in target cells needs to recognize the guide strand as a miRNA, fewer chemical modifications are suitable. In some variations, a 2'-fluoro (2'-F) modification to the guide strand helps to protect it from exonucleases, making the guide strand more stable. See Rooij and Kauppinen, "Development of microRNA therapeutics is coming of age," *EMBO Mol Med.*, (2014 July); 6(7): 851-864; Garzon et al., "Targeting microRNAs in cancer: rationale, strategies and challenges." *Nat Rev Drug Discov*. (2010 October); 9(10): 775-89; and Bader et al., "Developing therapeutic microRNAs for cancer." *Gene Ther*. (2011 December); 18(12): 1121-6, all incorporated herein by reference in its entirety.

Nucleic Acid Synthesis

The nucleic acids described herein may be produced enzymatically or by partial/total organic synthesis. In one embodiment, the nucleic acid is prepared chemically. Methods of synthesizing RNA and DNA molecules are known in the art, in particular, the chemical synthesis methods as described in Verma and Eckstein (1998) Annul Rev. Biochem. 67:99-134. RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA molecules, e.g., RNA silencing oligonucleotides, can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) Methods Enzymol. 180:51-62). The RNA may be dried for storage or dissolved in an aqueous solution. The solution may contain buffers or salts to inhibit annealing, and/or promote stabilization of the single strands.

Nucleic acids can be produced biologically using an expression vector. For instance, to synthesize an antisense nucleic acid, one can insert into a vector all or a portion of a cDNA has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. The antisense expression vector is prepared according to standard recombinant DNA methods for constructing recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector can be introduced into cells using a standard transfection technique.

Ribozymes

In still another embodiment, the nucleic acid molecule is a ribozyme. Ribozymes are catalytic RNA molecules having extensive secondary structure and which intrinsically capable of cleaving a single-stranded nucleic acid, such as an mRNA, to which they have a complementary region.

Small Molecule Therapeutics

In some embodiments of the invention, small non-oligonucleotide molecules are used as therapeutic agents. For instance, many of the target molecules described herein are proteins whose biological activities are amenable to modulation with small molecules, such as small molecules that interfere with a protein's binding or signaling activities.

For instance, in some variations of the invention, the agent is a histone deacetylase inhibitor, such as Romidepsin (Istodax™; (1S,4S,7Z,10S,16E,21R)-7-ethylidene-4,21-diisopropyl-2-oxa-12,13-dithia-5,8,20,23-tetrazabicyclo [8.7.6]tricos-16-ene-3,6,9,19,22-pentone) or Vorinostat (suberanilohydroxamic acid; SAHA; N-Hydroxy-N'-phenyloctanediamide; Zolinza™).

In some variations of the invention a tyrosine kinase inhibitor is used as a therapeutic agent. Exemplary TK inhibitors include Axitinib, cediranib, pazopanib, Pegaptanib, ponatinib, Regorafenib, Sorafenib, sunitinib, Vandetanib, and Vatalanib.

Axitinib (AG013736; N-Methyl-2-[[3-[(E)-2-pyridin-2-ylethenyl]-1H-indazol-6-yl]sulfanyl]benzamide; Inlyta™) is a small molecule tyrosine kinase inhibitor developed by Pfizer. Cediranib (AZD-2171; 4-[(4-fluoro-2-methyl-1H-indol-5-yl)oxy]-6-methoxy-7-[3-(pyrrolidin-1-yl)propoxy] quinazoline; Recentin™) is an inhibitor of vascular endothelial growth factor (VEGF) receptor tyrosine kinases. Pazopanib (5-[[4-[(2,3-Dimethyl-2H-indazol-6-yl)methylamino]-2-pyrimidinyl]amino]-2-methylbenzolsulfonamide; Votrient™) is a selective multi-targeted receptor tyrosine kinase inhibitor that blocks tumour growth and inhibits angiogenesis. Pegaptanib (Macugen™; RNA, ((2'-deoxy-2'-fluoro)C-Gm-Gm-A-A-(2'-deoxy-2'-fluoro)U-(2'-deoxy-2'-fluoro)C-Am-Gm-(2'-deoxy-2'-fluoro)U-Gm-Am-Am-(2'-deoxy-2'-fluoro)U-Gm-(2'-deoxy-2'-fluoro)C-(2'-deoxy-2'-fluoro)U-(2'-deoxy-2'fluoro)U-Am-(2'-deoxy-2'-fluoro)U-Am-(2'-deoxy-2'-fluoro)C-Am-(2'-deoxy-2'-fluoro)U-(2'deoxy-2'-fluoro)C-(2'-deoxy-2'-fluoro)C-Gm-(3'→3')-dT), 5'-ester with α,α'-[4,12-dioxo-6[[[5-(phosphoonoxy)pentyl]amino]carbonyl]-3,13-dioxa-5,11-diaza-1,15-pentadecanediyl]bis[ω-methoxypoly(oxy-1,2-ethanediyl)], sodium salt) is a pegylated anti-VEGF aptamer, a single strand nucleic acid that binds with specificity to the $VEGF_{165}$ isoform.

Ponatinib (Iclusig™; previously AP24534; 3-(2-Imidazo [1,2-b]pyridazin-3-ylethynyl)-4-methyl-N-[4-[(4-methylpiperazin-1-yl)methyl]-3-(trifluoromethyl)phenyl]benzamide) is an orally administered TK inhibitor drug that targets BCR-ABL. Regorafenib (BAY 73-4506; 4-[4-({[4-Chloro-3-(trifluoromethyl)phenyl]carbamoyl}amino)-3-fluorophenoxy]-N-methylpyridine-2-carboxamide hydrate; Stivarga™) is an oral multi-kinase inhibitor developed by Bayer that targets VEGFR2 and TIE2. Sorafenib (4-[4-[[4-chloro-3-(trifluoromethyl)phenyl]carbamoylamino] phenoxy]-N-methyl-pyridine-2-carboxamide Nexavar™) is a multi-kinase inhibitor with activity against VEGFR, PDGFR, and other kinases. Sunitinib (SU11248; N-(2-diethylaminoethyl)-5-[(Z)-(5-fluoro-2-oxo-1H-indol-3-ylidene)methyl]-2,4-dimethyl-1H-pyrrole-3-carboxamide; Sutent™), developed by Pfizer, is another orally administrable receptor tyrosine kinase inhibitor. Vandetanib (N-(4-bromo-2-fluorophenyl)-6-methoxy-7-[(1-methylpiperidin-4-yl)methoxy]quinazolin-4-amine; Caprelsa™) is an orally administrable tyrosine kinase inhibitor developed by Astra Zeneca that blocks VEGF2 and EGFR. Vatalanib (N-(4-chlorophenyl)-4-(pyridin-4-ylmethyl)phthalazin-1-amine) is a TK inhibitor that targets VEGFR's and PDGFR-beta, among others.

In still other variations, antibodies and soluble receptors can be used as TK inhibitors. for instance, antibodies that bind to the extracellular domain of VEGFR1, antibodies that bind to the extracellular domain of VEGFR2, and combinations thereof can be used as modulators of these receptors. Likewise, ligand traps that comprise soluble extracellular domain fragments of such receptors can be used to sequester ligand and inhibit receptor tyrosine kinases. Exemplary agents include Bevacizumab or Aflibercept.

Pharmaceutical Formulations and Routes of Administration

Compounds for therapeutic administration described herein or identifiable according to the teachings herein may be formulated in pharmaceutical compositions with a pharmaceutically acceptable excipient. The compound or composition comprising the compound is administered by any route that permits treatment of the disease or condition.

One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

In many embodiments, localized administration to a target tissue, tumor, organ, or fluid is desirable and contemplated, e.g., to increase localized dose at the target and reduce off-target side effects. For instance, in an embodiment in which treatment is targeted to a tumor, intra-tumoral injection, or localized administration to an organ or tissue harboring the tumor (e.g., by injection or catheter-mediated localized delivery) is contemplated. In an embodiment where the tumor is a glioblastoma, localized administration to the brain or CNS or cerebrospinal fluid is contemplated.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In some embodiments, an active agent is formulated with one or more pharmaceutically acceptable excipients, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Formulation and Delivery of Nucleic Acids

Nucleic acids as described herein can be administered directly or delivered to cells by transformation or transfection via a vector, including viral vectors or plasmids, into which has been placed DNA encoding the nucleic acid with the appropriate regulatory sequences, including a promoter, to result in expression of the nucleic acid in the desired cell. Known methods include standard transient transfection, stable transfection and delivery using viruses ranging from retroviruses to adenoviruses. Delivery of nucleic acid inhibitors by replicating or replication-deficient vectors is contemplated. Expression can also be driven by either constitutive or inducible promoter systems (Paddison et al., Methods Mol. Biol. 265:85-100, 2004). In other embodiments, expression may be under the control of tissue or development-specific promoters.

For example, vectors may be introduced by transfection using carrier compositions such as Lipofectamine 2000 (Life Technologies) or Oligofectamine (Life Technologies). Transfection efficiency may be checked using fluorescence microscopy for mammalian cell lines after co-transfection of hGFP-encoding pAD3 (Kehlenback et al., 1998, J. Cell Biol. 141:863-74).

Delivery of nucleic acids may also be achieved via (a) liposomes and liposome-protein conjugates and mixtures; (b) non-liposomal lipid and cationic lipid formulations; (c) activated dendrimer formulations; (d) a polymer formulation such as polyethylenimine (PEI) or pluronic gels or ethylene vinyl acetate copolymer (EVAc), (e) a viral-liposome complex, such as Sendai virus; (f) as a peptide-DNA conjugate;

(g) catheters to deliver intra-luminal formulations of the nucleic acid as a solution or in a complex with a liposome; (h) catheters to deliver to adventitial tissue as a solution or in a complex with a liposome; or (i) bound to a delivery agent such as a targeting moiety, or any suitable carrier such as a peptide or fatty acid molecule. The delivery route will be the one that provides the best inhibitory effect as measured according to the criteria described herein.

Nucleic acids and small molecules also may be packaged into synthetic or isolated cellular exosomes for administration and delivery to subjects. See, e.g., Johnsen et al., "A comprehensive overview of exosomes as drug delivery vehicles—Endogenous nanocarriers for targeted cancer therapy," Biochimica et Biophysica Acta (BBA)—Reviews on Cancer (August 2014) 1846(1): 75-87; US Patent Publication 2014/0093557; US Patent Publication No. 20150093433; all incorporated herein by reference in their entirety.

Tools to improve delivery of miRNA modulators include cholesterol conjugation and modification of the phosphate backbone of the miRNA with phosphorothioate (PS) linkages.

Nucleic acids and other therapeutic agents also can be conjugated to carrier proteins to improve pharmacokinetics and/or targeted delivery. For example, Karkan et al, "A Unique Carrier for Delivery of Therapeutic Compounds beyond the Blood-Brain Barrier," *PLoS ONE*, (June 2008) 3(6): e2469 describe conjugation of drugs n iron-transport protein, termed p97 (melanotransferrin) to improve trafficking across the blood-brain barrier. Such conjugates are contemplated herein for methods of treatment of diseases of the brain, including glioblastomas. Such conjugates of therapeutic agents described herein are, as compositions of matter, aspects of the invention.

Vectors for Delivery of Polynucleotide Therapies and Antigens

Any suitable vector may be used to introduce a polynucleotide that encodes a therapeutic agent of the invention. Exemplary vectors that have been described in the literature include replication deficient retroviral vectors, including but not limited to lentivirus vectors [Kim et al., J. Virol., 72(1): 811-816 (1998); Kingsman & Johnson, Scrip Magazine, October, 1998, pp. 43 46.]; adeno-associated viral (AAV) vectors [U.S. Pat. Nos. 5,474,935; 5,139,941; 5,622,856; 5,658,776; 5,773,289; 5,789,390; 5,834,441; 5,863,541; 5,851,521; 5,252,479; Gnatenko et al., J. Invest. Med., 45: 87 98 (1997)]; adenoviral (AV) vectors [See, e.g., U.S. Pat. Nos. 5,792,453; 5,824,544; 5,707,618; 5,693,509; 5,670,488; 5,585,362; Quantin et al., Proc. Natl. Acad. Sci. USA, 89: 2581 2584 (1992); Stratford Perricadet et al., J. Clin. Invest., 90: 626 630 (1992); and Rosenfeld et al., Cell, 68: 143 155 (1992)]; an adenoviral adenoassociated viral chimeric (see for example, U.S. Pat. No. 5,856,152) or a vaccinia viral or a herpesviral (see for example, U.S. Pat. Nos. 5,879,934; 5,849,571; 5,830,727; 5,661,033; 5,328,688; Lipofectin mediated gene transfer (BRL); liposomal vectors [See, e.g., U.S. Pat. No. 5,631,237 (Liposomes comprising Sendai virus proteins)]; and combinations thereof.

Vector selection and selection of appropriate expression control sequences (e.g., tissue specific promoters) can facilitate more targeted/localized expression.

Methods of Treatment

Provided herein are methods of treatment of different types of cancer in a mammalian subject in need thereof, comprising administering to the subject a compound or composition as described herein, in an amount effective to treat the cancer. Standard dose-response studies are used to optimize dose and dosing schedule. To help refine initial dose, the levels of a target miRNA or transcription factor can be measured in animal models and/or tissue samples (e.g., isolated primary tumors).

The disclosed methods are useful for treating cancer, for example, inhibiting cancer growth, including complete cancer remission, for inhibiting cancer metastasis, and for promoting cancer resistance. The term "cancer growth" generally refers to any one of a number of indices that suggest change within the cancer to a more developed form. Thus, indices for measuring an inhibition of cancer growth include but are not limited to a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens.

Although aspects of the invention has been described with particularity in the context of glioblastoma, the invention can be applied to other cancers as well. In one aspect, the cancer comprises a solid tumor, for example, a carcinoma and a sarcoma. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. The invention also provides methods of treatment of cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Age (child and adult), sex (male and female), primary and secondary, pre- and post-metastatic, acute and chronic, benign and malignant, anatomical location cancer embodiments and variations are contemplated targets. Cancers are grouped by embryonic origin (e.g., carcinoma, lymphomas, and sarcomas), by organ or physiological system, and by miscellaneous grouping. Particular cancers may overlap in their classification, and their listing in one group does not exclude them from another.

Brain and central nervous system (CNS) cancers and tumors that may be targeted include astrocytomas (including cerebellar and cerebral), brain stem glioma, brain tumors, malignant gliomas, ependymoma, glioblastoma, medulloblastoma, supratentorial primitive neuroectodermal tumors, visual pathway and hypothalamic gliomas, primary central nervous system lymphoma, ependymoma, brain stem glioma, visual pathway and hypothalamic glioma, extracranial germ cell tumor, medulloblastoma, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, gliomas, and metastatic tumor cell invasion in the central nervous system.

Dosing

The term "therapeutically effective amount" refers to an amount of a compound sufficient exhibit a detectable treatment, amelioration, or inhibitory effect in a patient or in an experimental trial involving multiple patients compared to a placebo or control. In the context of a therapy for a subject with a neoplastic condition, evidence of a therapeutic effect includes any one or more of the following: shrinkage of the neoplasm, a slowing or halting of growth/progression, inhibiting metastasis, increased survival, increased progression-free survival, increased quality of life during period of survival (e.g., reduction of symptoms/discomfort), and other accepted measures.

A dose of administration will depend on factors such as route of administration (local vs. systemic), patient characteristics (e.g., gender, weight, health, side effects); the nature and extent of the condition; and the therapeutic or combination of therapeutics selected for administration. Therapeutically effective amounts for a given situation can be estimated from in vitro studies to determine, e.g., $IC_{50}$ concentrations, pre-clinical studies and clinical studies in animals and humans, and the like, and determined by routine experimentation that is within the skill and judgment of the clinician.

Combination Therapy

The methods disclosed herein include the use combinations of therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used. In some cases, a compound disclosed herein is administered and/or formulated with a second therapeutic.

The combinations therapies taught herein can be further combined with other standard-of-care therapies for treating the same or similar conditions.

In the context of cancers, the additional therapeutic can be one or more of a chemotherapeutic or an immunotherapeutic agent (e.g., a therapeutic antibody or a cancer vaccine). In some specific cases, the additional therapeutic is a cytokine, an anti-inflammatory agent, a cancer vaccine, a cancer antigen, or a polynucleotide encoding a cancer antigen. In some cases, the second therapeutic is radiation.

REFERENCES CITED

Following is a non-comprehensive list of scientific references cited herein. All of the references are incorporated by reference in their entirety, and in particular for the material for which they have been cited.

Alexander, B. M., Lee, E. Q., Reardon, D. A., and Wen, P. Y. (2013). Current and future directions for Phase II trials in high-grade glioma. Expert Rev. Neurother. 13, 369-387.

Aten, J. E., Fuller, T. F., Lusis, A. J., and Horvath, S. (2008). Using genetic markers to orient the edges in quantitative trait networks: the NEO software. BMC Syst. Biol. 2, 34.

Baek, D., Villén, J., Shin, C., Camargo, F. D., Gygi, S. P., and Bartel, D. P. (2008). The impact of microRNAs on protein output. Nature 455, 64-71.

Bansal, M., Yang, J., Karan, C., Menden, M. P., Costello, J. C., Tang, H., Xiao, G., Li, Y., Allen, J., Zhong, R., et al. (2014). A community computational challenge to predict the activity of pairs of compounds. Nat. Biotechnol. 32, 1213-1222.

Bliss, C. I. (1939). The toxicity of poisons applied jointly. Ann. Appl. Biol. 26, 585-615.

Bouchie, A. (2013). First microRNA mimic enters clinic. Nat. Biotechnol. 31, 577.

Brennan, C. W., Verhaak, R. G. W., McKenna, A., Campos, B., Noushmehr, H., Salama, S. R., Zheng, S., Chakravarty, D., Sanborn, J. Z., Berman, S. H., et al. (2013). The somatic genomic landscape of glioblastoma. Cell 155, 462-477.

Brooks, A. N., Reiss, D. J., Allard, A., Wu, W.-J., Salvanha, D. M., Plaisier, C. L., Chandrasekaran, S., Pan, M., Kaur, A., and Baliga, N. S. (2014). A system-level model for the microbial regulatory genome. Mol. Syst. Biol. 10, 740.

Cai, W., Hu, L., and Foulkes, J. G. (1996). Transcription-modulating drugs: mechanism and selectivity. Curr. Opin. Biotechnol. 7, 608-615.

Carro, M. S., Lim, W. K., Alvarez, M. J., Bollo, R. J., Zhao, X., Snyder, E. Y., Sulman, E. P., Anne, S. L., Doetsch, F., Colman, H., et al. (2010). The transcriptional network for mesenchymal transformation of brain tumours. Nature 463, 318-325.

Chen, J. C., Alvarez, M. J., Talos, F., Dhruv, H., Rieckhof, G. E., Iyer, A., Diefes, K. L., Aldape, K., Berens, M., Shen, M. M., et al. (2014). Identification of causal genetic drivers of human disease through systems-level analysis of regulatory networks. Cell 159, 402-414.

Chen et al., "Vertebrate animal models of glioma: understanding the mechanisms and developing new therapies." *Biochim Biophys Acta*. (2013 August); 1836(1):158-65.

Choi, C. H., Park, Y.-A., Choi, J.-J., Song, T., Song, S. Y., Lee, Y.-Y., Lee, J.-W., Kim, T.-J., Kim, B.-G., and Bae, D.-S. (2012). Angiotensin II type I receptor and miR-155 in endometrial cancers: synergistic antiproliferative effects of anti-miR-155 and losartan on endometrial cancer cells. Gynecol. Oncol. 126, 124-131.

Friedman, R. C., Farh, K. K.-H., Burge, C. B., and Bartel, D. P. (2009). Most mammalian mRNAs are conserved targets of microRNAs. Genome Res. 19, 92-105.

Gonzalez-Perez, A., Perez-Llamas, C., Deu-Pons, J., Tamborero, D., Schroeder, M. P., Jene-Sanz, A., Santos, A., and Lopez-Bigas, N. (2013). IntOGen-mutations identifies cancer drivers across tumor types. Nat. Methods 10, 1081-1082.

Goodarzi, H., Elemento, O., and Tavazoie, S. (2009). Revealing global regulatory perturbations across human cancers. Mol. Cell 36, 900-911.

Gravendeel, L. A. M., Kouwenhoven, M. C. M., Gevaert, O., de Rooi, J. J., Stubbs, A. P., Duijm, J. E., Daemen, A., Bleeker, F. E., Bralten, L. B. C., Kloosterhof, N. K., et al. (2009). Intrinsic gene expression profiles of gliomas are a better predictor of survival than histology. Cancer Res. 69, 9065-9072.

Heneghan, H. M., Miller, N., and Kerin, M. J. (2010). MiRNAs as biomarkers and therapeutic targets in cancer. Curr. Opin. Pharmacol. 10, 543-550.

Iwamoto, F. M., Lamborn, K. R., Kuhn, J. G., Wen, P. Y., Yung, W. K. A., Gilbert, M. R., Chang, S. M., Lieberman, F. S., Prados, M. D., and Fine, H. A. (2011). A phase I/II trial of the histone deacetylase inhibitor romidepsin for adults with recurrent malignant glioma: North American Brain Tumor Consortium Study 03-03. Neuro-Oncol. 13, 509-516.

Jiang, Q., Wang, Y., Hao, Y., Juan, L., Teng, M., Zhang, X., Li, M., Wang, G., and Liu, Y. (2009). miR2Disease: a manually curated database for microRNA deregulation in human disease. Nucleic Acids Res. 37, D98-D104.

Jolma, A., Yan, J., Whitington, T., Toivonen, J., Nitta, K. R., Rastas, P., Morgunova, E., Enge, M., Taipale, M., Wei, G., et al. (2013). DNA-binding specificities of human transcription factors. Cell 152, 327-339.

Jornsten, R., Abenius, T., Kling, T., Schmidt, L., Johansson, E., Nordling, T. E. M., Nordlander, B., Sander, C., Gennemark, P., Funa, K., et al. (2011). Network modeling of the transcriptional effects of copy number aberrations in glioblastoma. Mol. Syst. Biol. 7, 486.

Karkan, D., Pfeifer, C., Vitalis, T. Z., Arthur, G., Ujiie, M., Chen, Q., Tsai, S., Koliatis, G., Gabathuler, R., and Jefferies, W. A. (2008). A unique carrier for delivery of therapeutic compounds beyond the blood-brain barrier. PloS One 3, e2469.

Kertesz, M., Iovino, N., Unnerstall, U., Gaul, U., and Segal, E. (2007). The role of site accessibility in microRNA target recognition. Nat. Genet. 39, 1278-1284.

Lehár, J., Krueger, A. S., Avery, W., Heilbut, A. M., Johansen, L. M., Price, E. R., Rickles, R. J., Short, G. F., Staunton, J. E., Jin, X., et al. (2009). Synergistic drug combinations tend to improve therapeutically relevant selectivity. Nat. Biotechnol. 27, 659-666.

Liu, Q., Zheng, J.-M., Chen, J.-K., Yan, X.-L., Chen, H.-M., Nong, W.-X., and Huang, H.-Q. (2014). Histone deacetylase 5 promotes the proliferation of glioma cells by upregulation of Notch 1. Mol. Med. Rep. 10, 2045-2050.

Lu, M., Zhang, Q., Deng, M., Miao, J., Guo, Y., Gao, W., and Cui, Q. (2008). An analysis of human microRNA and disease associations. PloS One 3, e3420.

Madhavan, S., Zenklusen, J.-C., Kotliarov, Y., Sahni, H., Fine, H. A., and Buetow, K. (2009). Rembrandt: helping personalized medicine become a reality through integrative translational research. Mol. Cancer Res. MCR 7, 157-167.

Mathelier, A., Zhao, X., Zhang, A. W., Parcy, F., Worsley-Hunt, R., Arenillas, D. J., Buchman, S., Chen, C., Chou, A., Ienasescu, H., et al. (2014). JASPAR 2014: an extensively expanded and updated open-access database of transcription factor binding profiles. Nucleic Acids Res. 42, D142-D147.

Matys, V., Kel-Margoulis, O. V., Fricke, E., Liebich, I., Land, S., Barre-Dirrie, A., Reuter, I., Chekmenev, D., Krull, M., Hornischer, K., et al. (2006). TRANSFAC and its module TRANSCompel: transcriptional gene regulation in eukaryotes. Nucleic Acids Res. 34, D108-D110.

Murat, A., Migliavacca, E., Gorlia, T., Lambiv, W. L., Shay, T., Hamou, M.-F., de Tribolet, N., Regli, L., Wick, W., Kouwenhoven, M. C. M., et al. (2008). Stem cell-related "self-renewal" signature and high epidermal growth factor receptor expression associated with resistance to concomitant chemoradiotherapy in glioblastoma. J. Clin. Oncol. Off. J. Am. Soc. Clin. Oncol. 26, 3015-3024.

Neph, S., Vierstra, J., Stergachis, A. B., Reynolds, A. P., Haugen, E., Vernot, B., Thurman, R. E., John, S., Sandstrom, R., Johnson, A. K., et al. (2012). An expansive human regulatory lexicon encoded in transcription factor footprints. Nature 489, 83-90.

Newburger, D. E., and Bulyk, M. L. (2009). UniPROBE: an online database of protein binding microarray data on protein-DNA interactions. Nucleic Acids Res. 37, D77-D82.

Oh et al., "Immunocompetent murine models for the study of glioblastoma immunotherapy." J Transl Med. (2014 Apr. 29); 12:107.

Ohka, F., Natsume, A., and Wakabayashi, T. (2012). Current trends in targeted therapies for glioblastoma multiforme. Neurol. Res. Int. 2012, 878425.

Patil, S. A., Hosni-Ahmed, A., Jones, T. S., Patil, R., Pfeffer, L. M., and Miller, D. D. (2013). Novel approaches to glioma drug design and drug screening. Expert Opin. Drug Discov. 8, 1135-1151.

Piñero, J., Queralt-Rosinach, N., Bravo, A., Deu-Pons, J., Bauer-Mehren, A., Baron, M., Sanz, F., and Furlong, L. I. (2015). DisGeNET: a discovery platform for the dynamical exploration of human diseases and their genes. Database J. Biol. Databases Curation 2015, bav028.

Plaisier, C. L., Pan, M., and Baliga, N. S. (2012). A miRNA-regulatory network explains how dysregulated miRNAs perturb oncogenic processes across diverse cancers. Genome Res.

Reiss, D. J., Plaisier, C. L., Wu, W.-J., and Baliga, N. S. (2015). cMonkey$_2$: Automated, systematic, integrated detection of co-regulated gene modules for any organism. Nucleic Acids Res.

Rutledge, W. C., Kong, J., Gao, J., Gutman, D. A., Cooper, L. A. D., Appin, C., Park, Y., Scarpace, L., Mikkelsen, T., Cohen, M. L., et al. (2013). Tumor-infiltrating lymphocytes in glioblastoma are associated with specific genomic alterations and related to transcriptional class. Clin. Cancer Res. Off. J. Am. Assoc. Cancer Res. 19, 4951-4960.

Sathornsumetee, S., Reardon, D. A., Desjardins, A., Quinn, J. A., Vredenburgh, J. J., and Rich, J. N. (2007). Molecularly targeted therapy for malignant glioma. Cancer 110, 13-24.

Sawa, H., Murakami, H., Kumagai, M., Nakasato, M., Yamauchi, S., Matsuyama, N., Tamura, Y., Satone, A., Ide, W., Hashimoto, I., et al. (2004). Histone deacetylase inhibitor, FK228, induces apoptosis and suppresses cell proliferation of human glioblastoma cells in vitro and in vivo. Acta Neuropathol. (Berl.) 107, 523-531.

Smith, C., Santi, M., Rajan, B., Rushing, E. J., Choi, M. R., Rood, B. R., Cornelison, R., MacDonald, T. J., and Vukmanovic, S. (2009). A novel role of HLA class I in the pathology of medulloblastoma. J. Transl. Med. 7, 59.

Sumazin, P., Yang, X., Chiu, H.-S., Chung, W.-J., Iyer, A., Llobet-Navas, D., Rajbhandari, P., Bansal, M., Guarnieri, P., Silva, J., et al. (2011). An extensive microRNA-mediated network of RNA-RNA interactions regulates established oncogenic pathways in glioblastoma. Cell 147, 370-381.

Sun, P., Xia, S., Lal, B., Eberhart, C. G., Quinones-Hinojosa, A., Maciaczyk, J., Matsui, W., Dimeco, F., Piccirillo, S. M., Vescovi, A. L., et al. (2009). DNER, an epigenetically modulated gene, regulates glioblastoma-derived neurosphere cell differentiation and tumor propagation. Stem Cells Dayt. Ohio 27, 1473-1486.

Toledo, C. M., Ding, Y., Hoellerbauer, P., Davis, R. J., Basom, R., Girard, E. J., Corrin, P., Hart, T., Bolouri, H., Davison, J., et al. (2015). Genome-wide CRISPR-Cas9 screens reveal loss of redundancy between PKMYT1 and WEE1 in Glioblastoma multiforme stemlike cells. Cell Reports.

Van Rooij, Eva, and Sakari Kauppinen. "Development of microRNA Therapeutics Is Coming of Age." *EMBO Molecular Medicine* 6.7 (2014): 851-864. *PMC*. Web. 28 Apr. 2016.

Wang, J., Zhuang, J., Iyer, S., Lin, X., Whitfield, T. W., Greven, M. C., Pierce, B. G., Dong, X., Kundaje, A., Cheng, Y., et al. (2012). Sequence features and chromatin structure around the genomic regions bound by 119 human transcription factors. Genome Res. 22, 1798-1812.

Welker et al., "Standardized orthotopic xenografts in zebrafish reveal glioma cell-line-specific characteristics and tumor cell heterogeneity." *Dis Model Mech.* (2016 Feb. 1); 9(2):199-210.

Wen, P. Y., Kesari, S., and Drappatz, J. (2006). Malignant gliomas: strategies to increase the effectiveness of targeted molecular treatment. Expert Rev. Anticancer Ther. 6, 733-754.

Wingender, E., Schoeps, T., and Donitz, J. (2013). TFClass: an expandable hierarchical classification of human transcription factors. Nucleic Acids Res. 41, D165-D170.

Xie, X., Lu, J., Kulbokas, E. J., Golub, T. R., Mootha, V., Lindblad-Toh, K., Lander, E. S., and Kellis, M. (2005). Systematic discovery of regulatory motifs in human promoters and 3' UTRs by comparison of several mammals. Nature 434, 338-345.

What is claimed is:

1. A method for identifying treatment targets for a condition, the method comprising:

receiving a set of multiomics data, the multiomics data including transcriptomics data including data related to the condition;

filtering the transcriptomics data to determine a set of highly expressed genes related to the condition;

determining from the set of highly expressed genes a set of biclusters, each bicluster representing a conditionally co-regulated module of genes; and determining from the set of biclusters a set of disease-relevant biclusters, wherein determining a set of biclusters comprises executing a biclustering algorithm using as training data one or more received sets of miRNA targets and/or one or more sets of transcription factor targets, wherein the biclustering algorithm uses as training data a set of transcription factor targets, and wherein the set of transcription factor targets is created by:

extracting from a human genome sequence a set of promoter sequences;

searching the set of promoter sequences for instances of DNA recognition motifs to create a set of instances of DNA recognition motifs; and identifying in the set of instances of DNA recognition motifs those instances that intersect with digital genomic footprints to create a transcription factor target gene database.

2. A method for identifying treatment targets for a condition, the method comprising:

receiving a set of multiomics data, the multiomics data including transcriptomics data including data related to the condition;

filtering the transcriptomics data to determine a set of highly expressed genes related to the condition;

determining from the set of highly expressed genes a set of biclusters, each bicluster representing a conditionally co-regulated module of genes; and determining from the set of biclusters a set of disease-relevant biclusters, wherein determining a set of biclusters comprises executing a biclustering algorithm using as training data one or more received sets of miRNA targets and/or one or more sets of transcription factor targets,
wherein determining from the set of biclusters a set of disease-relevant biclusters comprises:
determining from the set of biclusters a first subset of biclusters, each bicluster in the first subset of biclusters having conditional up/down regulation associated with patient survival in a set of validation data;
determining from the set of biclusters a second subset of biclusters, each bicluster in the second subset biclusters having conditional up/down regulation associated with patient survival or a disease hallmark in the set of multiomics data; and
selecting, as the set of disease-relevant biclusters, biclusters that are in both the first subset of biclusters and the second set of biclusters.

3. A method according to claim 2, wherein each of the validation data and the multiomics data comprises a set of survival data and a set of transcriptomics data.

4. A method for identifying treatment targets for a condition, the method comprising:
receiving a set of multiomics data, the multiomics data including transcriptomics data including data related to the condition;
filtering the transcriptomics data to determine a set of highly expressed genes related to the condition;
determining from the set of highly expressed genes a set of biclusters, each bicluster representing a conditionally co-regulated module of genes;
determining from the set of biclusters a set of disease-relevant biclusters, wherein determining a set of biclusters comprises executing a biclustering algorithm using as training data one or more received sets of miRNA targets and/or one or more sets of transcription factor targets;
receiving in the multiomics data a set of genomics data related to the condition;
filtering the set of genomics data to determine a set of somatically mutated genes associated with the condition; and
filtering the set of genomics data to determine a set of pathways aggregating somatically mutated genes.

5. A method according to claim 4, further comprising:
determining a set of bicluster eigengenes from the set of disease-relevant biclusters; and
determining from at least the set of bicluster eigengenes a set of causal transcription factors and a set of causal miRNAs.

6. A method according to claim 5, wherein determining from at least the set of bicluster eigengenes a set of causal transcription factors and a set of causal miRNAs comprises:
inputting into a network edge orienting algorithm:
the set of bicluster eigengenes;
the set of somatically mutated genes associated with the condition;
the set of pathways aggregating the somatically mutated genes;
a set of miRNAs from the multiomics data; and
a set of transcription factors from the multiomics data.

7. A method for identifying treatment targets for a condition, the method comprising:
receiving a set of multiomics data, the multiomics data including transcriptomics data including data related to the condition;
filtering the transcriptomics data to determine a set of highly expressed genes related to the condition;
determining from the set of highly expressed genes a set of biclusters, each bicluster representing a conditionally co-regulated module of genes; and
determining from the set of biclusters a set of disease-relevant biclusters, wherein determining a set of biclusters comprises executing a biclustering algorithm using as training data one or more received sets of miRNA targets and/or one or more sets of transcription factor targets;
expanding the set of mechanistic transcription factors to include other transcription factors in a same family as each of the set of mechanistic transcription factors;
finding a set of correlated transcription factors in the expanded set of mechanistic transcription factors that are correlated with bicluster eigengenes;
determining a first set of transcription factors that have both causal and mechanistic support for regulation of the same bicluster, by taking the intersection of the set of correlated transcription factors and the set of causal transcription factors;
determining a second set of transcription factors that have both causal and mechanistic support for regulation of the same bicluster, by inputting the set of causal transcription factors into an analysis of motif enrichment algorithm; and
taking the union of the first set of transcription factors and the second set of transcription factors to produce a set of treatment targets including causal and mechanistic transcription factors,
wherein determining from the set of highly expressed genes a set of biclusters further comprises:
determining a set of mechanistic transcription factors; and
determining a set of mechanistic miRNAs.

8. A method according to claim 7, further comprising:
evaluating, for treatment targets in the set of treatment targets, whether the treatment target is positively or negatively associated with survival;
determining the regulator function of the treatment target; and
determining whether to decrease expression or activity (knock down) or increase expression or activity of the treatment target to achieve a therapeutic effect for the condition.

9. A method of selecting a combination therapy to inhibit growth of neoplastic cells in a mammalian subject, the method comprising:
identifying two or more treatment targets, wherein the two or more treatment targets are independently selected from the group consisting of transcription factors and miRNAs, and determining whether increased expression/activity or decreased expression/activity of the two or more treatment targets is expected to decrease growth of the neoplastic cells, according to claim 8; and
selecting as a combination therapy two or more agents to modulate the treatment targets in the directions expected to decrease growth of the neoplastic cells.

10. The method according to claim 9, that comprises determining that a decreased expression or activity of two or more targets is expected to decrease growth of the neoplastic cells, and that comprises selecting as the combination therapy two or more interfering RNAs to decrease expression of the two or more targets.

11. A method of treatment of a mammalian subject to inhibit growth of neoplastic cells, the method comprising:
identifying two or more treatment targets, wherein the two or more treatment targets are independently selected from the group consisting of transcription factors and miRNAs, and determining whether increased expression/activity or decreased expression/activity of the two or more treatment targets is expected to decrease growth of the neoplastic cells, according to claim 8; and administering agents to the mammalian subject in amounts effective to modulate the treatment targets in the directions expected to decrease growth of the neoplastic cells.

12. The method according to claim 11 that comprises determining that decreased expression/activity of two or more treatment targets is expected to decrease growth of the neoplastic cells, and the administering step comprises administering interfering RNA molecules selected for the two or more treatment targets, to decrease expression/activity of the two or more targets.

13. A method for identifying treatment targets for a condition, the method comprising:
  receiving a set of multiomics data, the multiomics data including transcriptomics data including data related to the condition;
  filtering the transcriptomics data to determine a set of highly expressed genes related to the condition;
  determining from the set of highly expressed genes a set of biclusters, each bicluster representing a conditionally co-regulated module of genes; and
  determining from the set of biclusters a set of disease-relevant biclusters, wherein determining a set of biclusters comprises executing a biclustering algorithm using as training data one or more received sets of miRNA targets and/or one or more sets of transcription factor targets;
  determining restricted set of mechanistic miRNAs by restricting the set of mechanistic miRNAs to include only miRNAs that exhibit anti-correlated expression with bicluster eigengenes; and
  taking the union of the restricted set of mechanistic miRNAs and the set of causal miRNAs to produce a set of treatment targets including causal and mechnanistic miRNAs, wherein determining from the set of highly expressed genes a set of biclusters further comprises:
  determining a set of mechanistic transcription factors; and
  determining a set of mechanistic miRNAs.

* * * * *